(12) United States Patent
Doi et al.

(10) Patent No.: US 8,200,042 B2
(45) Date of Patent: *Jun. 12, 2012

(54) ENDOSCOPE APPARATUS AND PROGRAM

(75) Inventors: Takahiro Doi, Tokyo (JP); Fumio Hori, Tokyo (JP)

(73) Assignee: Olympus Corporation, Tokyo (JP)

( * ) Notice: Subject to any disclaimer, the term of this patent is extended or adjusted under 35 U.S.C. 154(b) by 1132 days.

This patent is subject to a terminal disclaimer.

(21) Appl. No.: 12/011,741

(22) Filed: Jan. 29, 2008

(65) Prior Publication Data

US 2009/0092278 A1 Apr. 9, 2009

(30) Foreign Application Priority Data

Jan. 31, 2007 (JP) ............... P2007-020906
May 29, 2007 (JP) ............... P2007-141685
Jul. 3, 2007 (JP) ............... P2007-175159

(51) Int. Cl.
*G06K 9/22* (2006.01)

(52) U.S. Cl. ........ 382/286; 382/173; 382/181; 382/276; 702/128; 702/155; 702/168; 702/189

(58) Field of Classification Search ................ 382/128, 382/129, 130, 131, 132, 173, 181, 276, 278; 702/128, 155, 168, 189
See application file for complete search history.

(56) References Cited

U.S. PATENT DOCUMENTS

| 5,140,265 | A | 8/1992 | Sakiyama et al. | |
|---|---|---|---|---|
| 6,215,914 | B1* | 4/2001 | Nakamura et al. | 382/284 |
| 6,640,002 | B1* | 10/2003 | Kawada | 382/141 |
| 2004/0247171 | A1* | 12/2004 | Hashimoto et al. | 382/141 |
| 2006/0042104 | A1 | 3/2006 | Donaldson et al. | |
| 2006/0193533 | A1 | 8/2006 | Araki et al. | |

(Continued)

FOREIGN PATENT DOCUMENTS

JP 04-198741 A 7/1992

(Continued)

OTHER PUBLICATIONS

U.S. Appl. No. 12/011,740, filed Jan. 29, 2008; Inventor: Fumio Hori; Title: Instrumentation Endoscope Apparatus.

(Continued)

*Primary Examiner* — David A Vanore
*Assistant Examiner* — Nicole Ippolito
(74) *Attorney, Agent, or Firm* — Holtz, Holtz, Goodman & Chick, PC

(57) ABSTRACT

An endoscope apparatus includes an electronic endoscope that picks up a measurement object and produces a picked-up-image signal; an image-processing unit that produces a image signal based on the picked-up-image signal; and an measurement processing unit that undertakes measurement processing to the measurement object based on the image signal. The measurement processing unit includes: a reference point-designating unit that designates two reference points on the measurement object; an approximate-outline—calculating unit that calculates an approximate outline by approximating the outline of the measurement object based on the reference points; and a loss-composing points-calculating unit that calculates loss-composing points that constitute a loss outline formed on the measurement object based on the reference points and the approximate outline. This enables loss size measurement upon designating two reference points, thereby reducing complex operations and improving operability.

35 Claims, 55 Drawing Sheets

U.S. PATENT DOCUMENTS

| | | | |
|---|---|---|---|
| 2007/0067131 A1* | 3/2007 | Teshima et al. | 702/118 |
| 2007/0147676 A1* | 6/2007 | Sasai | 382/149 |
| 2008/0240491 A1 | 10/2008 | Hori | |
| 2008/0292055 A1* | 11/2008 | Boone | 378/97 |

FOREIGN PATENT DOCUMENTS

| | | |
|---|---|---|
| JP | 09-281055 A | 10/1997 |
| JP | 2004-049638 A | 2/2004 |
| JP | 2005-204724 A | 8/2005 |

OTHER PUBLICATIONS

Office Action dated Sep. 30, 2011 issued in U.S. Appl. No. 12/011,740.

Japanese Office Action dated Feb. 28, 2012 and English translation thereof in counterpart Japanese Application No. 2007-175159.

Notice of Allowance mailed Feb. 6, 2012 in related U.S. Appl. No. 12/011,740.

\* cited by examiner

FIG. 49A
FIG. 49B
FIG. 49C
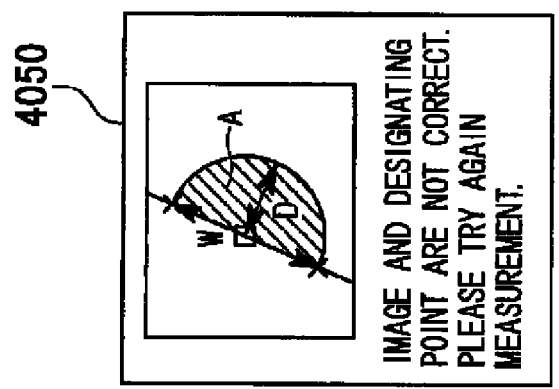
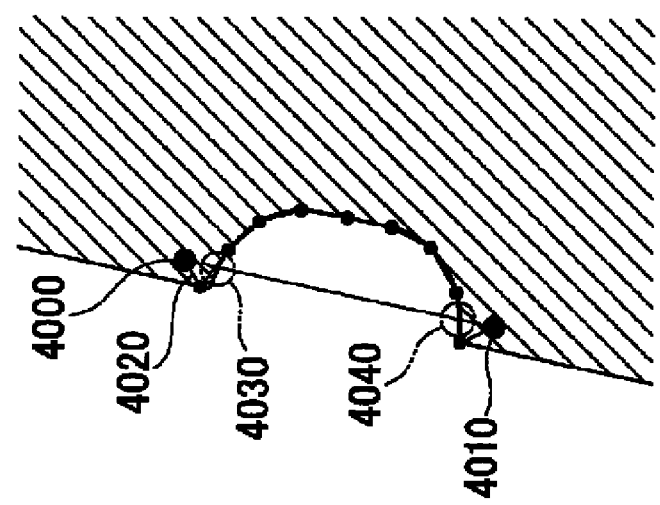
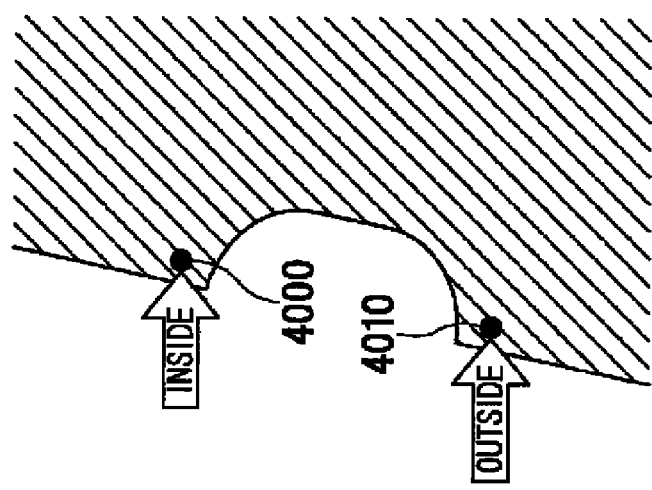

FIG. 50A
FIG. 50B
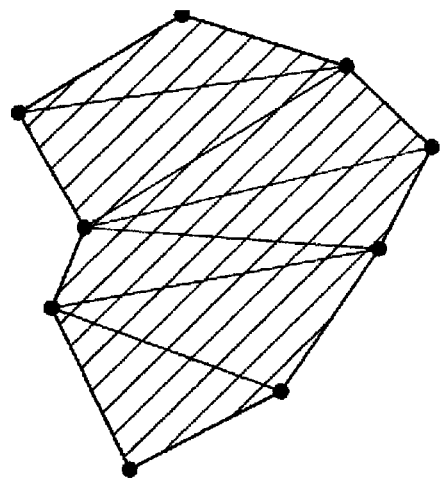
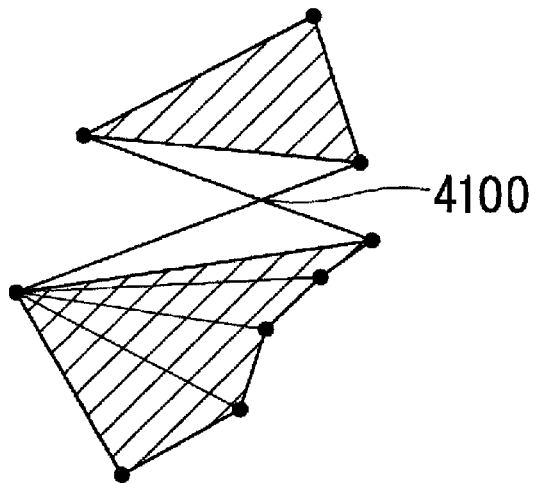
4100
LOSS AREA IS INDICATED BY SUM
OF AREAS OF TRIANGLES.

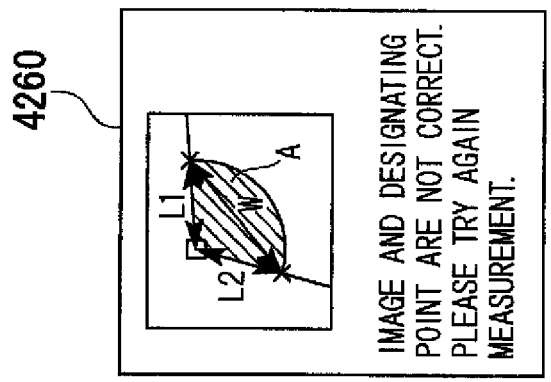
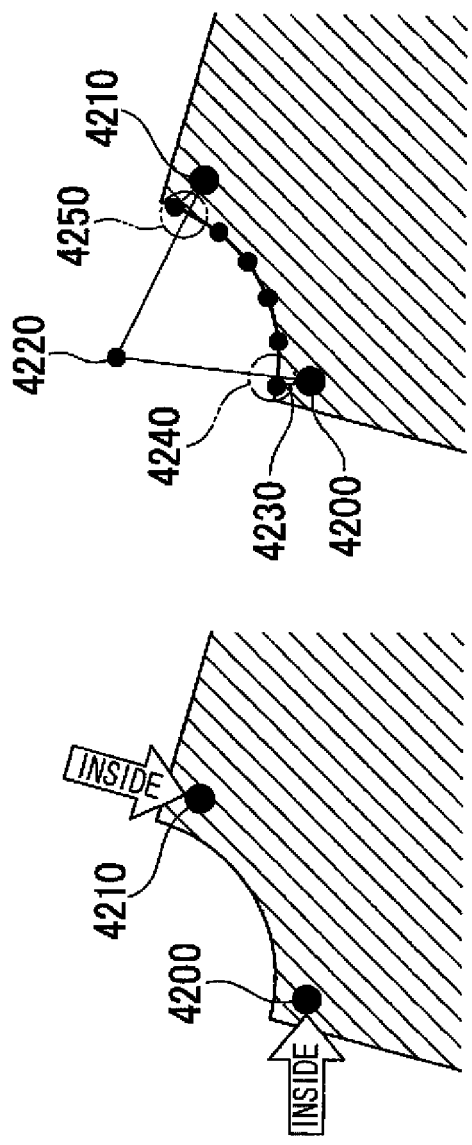
FIG. 51A  FIG. 51B  FIG. 51C

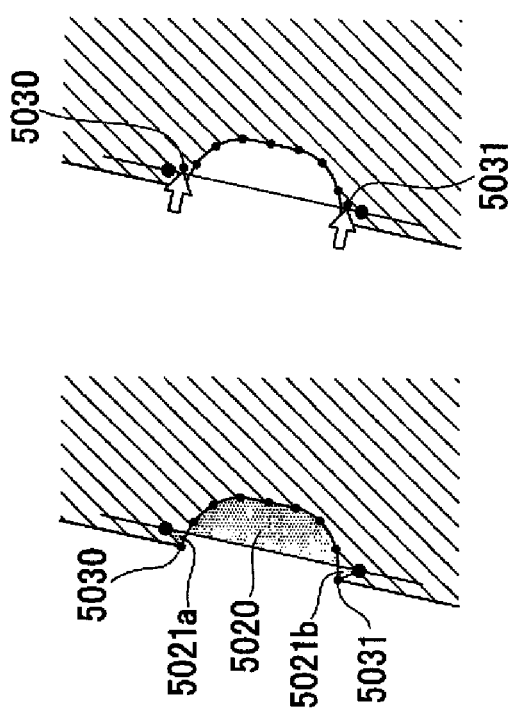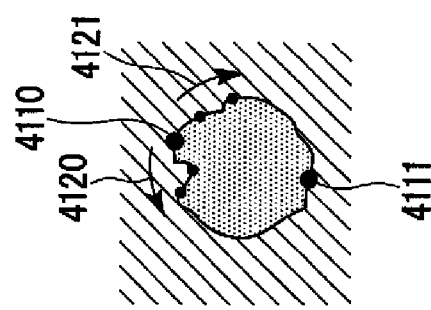

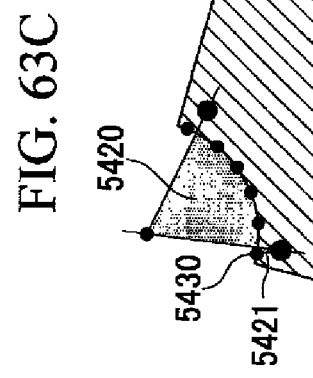
FIG. 63A
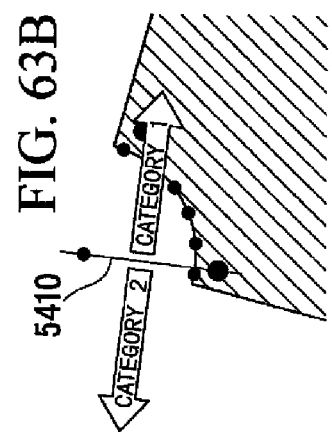
FIG. 63B
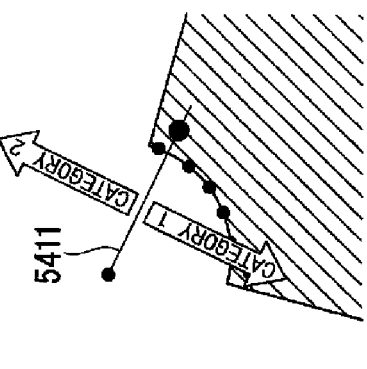
FIG. 63C
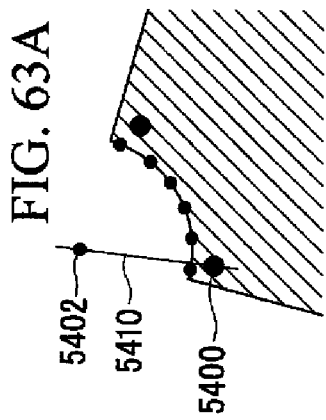
FIG. 63D
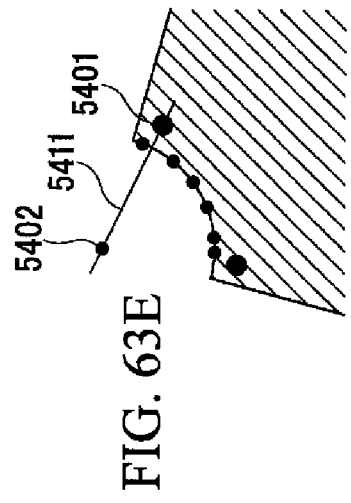
FIG. 63E
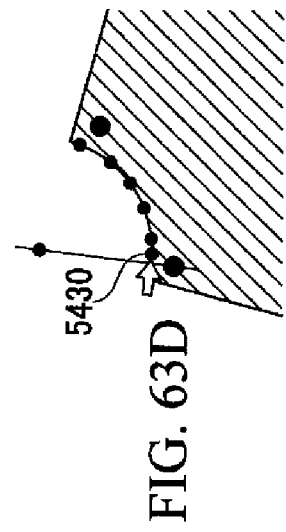
FIG. 63F
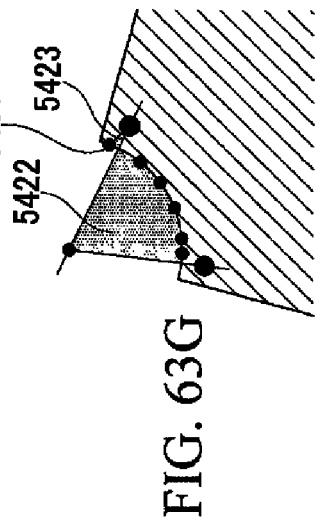
FIG. 63G
FIG. 63H

FIG. 65A

LABEL LIST (INITIAL STATE)

| LABEL NUMBER | COORDINATE | ADJACENT LABEL NUMBER 1 | ADJACENT LABEL NUMBER 2 |
|---|---|---|---|
| 1 | (X1,Y1) | 11 | 2 |
| 2 | (X2,Y2) | 1 | 3 |
| 3 | (X3,Y3) | 2 | 4 |
| 4 | (X4,Y4) | 3 | 5 |
| 5 | (X5,Y5) | 4 | 6 |
| 6 | (X6,Y6) | 5 | 7 |
| 7 | (X7,Y7) | 6 | 8 |
| 8 | (X8,Y8) | 7 | 9 |
| 9 | (X9,Y9) | 8 | 10 |
| 10 | (X10,Y10) | 9 | 11 |
| 11 | (X11,Y11) | 10 | 1 |

FIG. 65B

LABEL LIST (GROUP A)

| LABEL NUMBER | COORDINATE | ADJACENT LABEL NUMBER 1 | ADJACENT LABEL NUMBER 2 |
|---|---|---|---|
| 1 | (X1,Y1) | 11 | 2 |
| 2 | (X2,Y2) | 1 | 3 |
| 3 | (X3,Y3) | 2 | 4 |
| 4 | (X4,Y4) | 3 | 8 |
| 5 | (X5,Y5) | 7 | 6 |
| 6 | (X6,Y6) | 5 | 7 |
| 7 | (X7,Y7) | 6 | 5 |
| 8 | (X8,Y8) | 4 | 9 |
| 9 | (X9,Y9) | 8 | 10 |
| 10 | (X10,Y10) | 9 | 11 |
| 11 | (X11,Y11) | 10 | 1 |

FIG. 65C

LABEL LIST (GROUP B)

| LABEL NUMBER | COORDINATE | ADJACENT LABEL NUMBER 1 | ADJACENT LABEL NUMBER 2 |
|---|---|---|---|
| 1 | (X1,Y1) | 11 | 2 |
| 2 | (X2,Y2) | 1 | 3 |
| 3 | (X3,Y3) | 2 | 4 |
| 4 | (X4,Y4) | 3 | 7 |
| 5 | (X5,Y5) | 8 | 6 |
| 6 | (X6,Y6) | 5 | 7 |
| 7 | (X7,Y7) | 6 | 4 |
| 8 | (X8,Y8) | 5 | 9 |
| 9 | (X9,Y9) | 8 | 10 |
| 10 | (X10,Y10) | 9 | 11 |
| 11 | (X11,Y11) | 10 | 1 |

FIG. 65D

LABEL LIST (POST CORRECTED)

| LABEL NUMBER | COORDINATE | ADJACENT LABEL NUMBER 1 | ADJACENT LABEL NUMBER 2 |
|---|---|---|---|
| 1 | (X1,Y1) | 11 | 2 |
| 2 | (X2,Y2) | 1 | 3 |
| 3 | (X3,Y3) | 2 | 4 |
| 4 | (X4,Y4) | 3 | 5 |
| 5 | (X7,Y7) | 4 | 6 |
| 6 | (X6,Y6) | 5 | 7 |
| 7 | (X5,Y5) | 6 | 8 |
| 8 | (X8,Y8) | 7 | 9 |
| 9 | (X9,Y9) | 8 | 10 |
| 10 | (X10,Y10) | 9 | 11 |
| 11 | (X11,Y11) | 10 | 1 |

W1=3.45mm
W2=3.61mm
L=10.99mm
A=9.62mm²

ENDOSCOPE APPARATUS AND PROGRAM

BACKGROUND OF THE INVENTION

1. Field of the Invention

The present invention relates to an endoscope apparatus that conducts measurement processing on a measurement object based on images picked up by an electronic endoscope.

The present application is based on patent application Nos. 2007-020906 filed Jan. 31, 2007, 2007-141685 filed May 29, 2007, and 2007-175159 filed Jul. 3, 2007, in Japan, the contents of which are incorporated herein by reference.

2. Description of Related Art

Sometimes, turbine blade edges or compressor blade edges of gas turbines mainly used in aircraft are subject to losses due to foreign bodies. The size of loss is a factor of blade replacement, so its inspection is very important. Under this circumstance, conventional instrumental endoscopes approximated loss edges of turbine blades or compressor blades by virtual curves and virtual points and measured loss sizes based on the approximated virtual curves and points (see, cf. Patent Document 1).

Patent Document 1: Japanese Patent Application Laid-open No. 2005-204724

BRIEF SUMMARY OF THE INVENTION

The present invention is a loss measurement method using an endoscope apparatus that includes an electronic endoscope that picks up a measurement object and produces a picked-up-image signal, an image-processing unit that produces an image signal based on the picked-up-image signal, and a measurement processing unit that carries out a procedure of measuring the measurement object based on the image signal. The method includes processes of: designating two reference points on the measurement object; calculating an outline approximation line by approximating the outline of the measurement object; and calculating loss-composing points constituting the outline of a loss formed to the measurement object based on the reference points and the outline approximation line.

Also, the present invention is an endoscope apparatus that includes: an electronic endoscope that picks up a measurement object and produces a picked-up-image signal; an image-processing unit that produces an image signal based on the picked-up-image signal; and a measurement processing unit that undertakes measurement processing on the measurement object based on the image signal.

The measurement processing unit includes: a reference point-designating unit that designates two reference points on the measurement object; an outline-approximation-line-calculating unit that calculates an outline approximation line by approximating the outline of the measurement object based on the reference points; and a loss-composing points-calculating unit that calculates loss-composing points that constitute a loss outline formed on the measurement object based on the reference points and the outline approximation line.

BRIEF DESCRIPTION OF DRAWINGS

FIGS. 49A to 49C explain a problem in a second embodiment of the present invention for reference.

FIGS. 50A to 50B explain the problem in the second embodiment of the present invention for reference.

FIGS. 51A to 51C explain the problem in the second embodiment of the present invention for reference.

FIGS. 59A to 59E explain for reference the procedure of the twisted-shape detection process in the second embodiment (first operational example) of the present invention.

FIGS. 63A to 63H explain for reference the procedure of the twisted-shape detection process in the second embodiment (second operational example) of the present invention.

FIGS. 65A to 65D explain for reference details of a label list for use in the procedure of the twisted-shape detection process in the second embodiment (third operational example) of the present invention.

PREFERRED EMBODIMENTS

Figure 1:
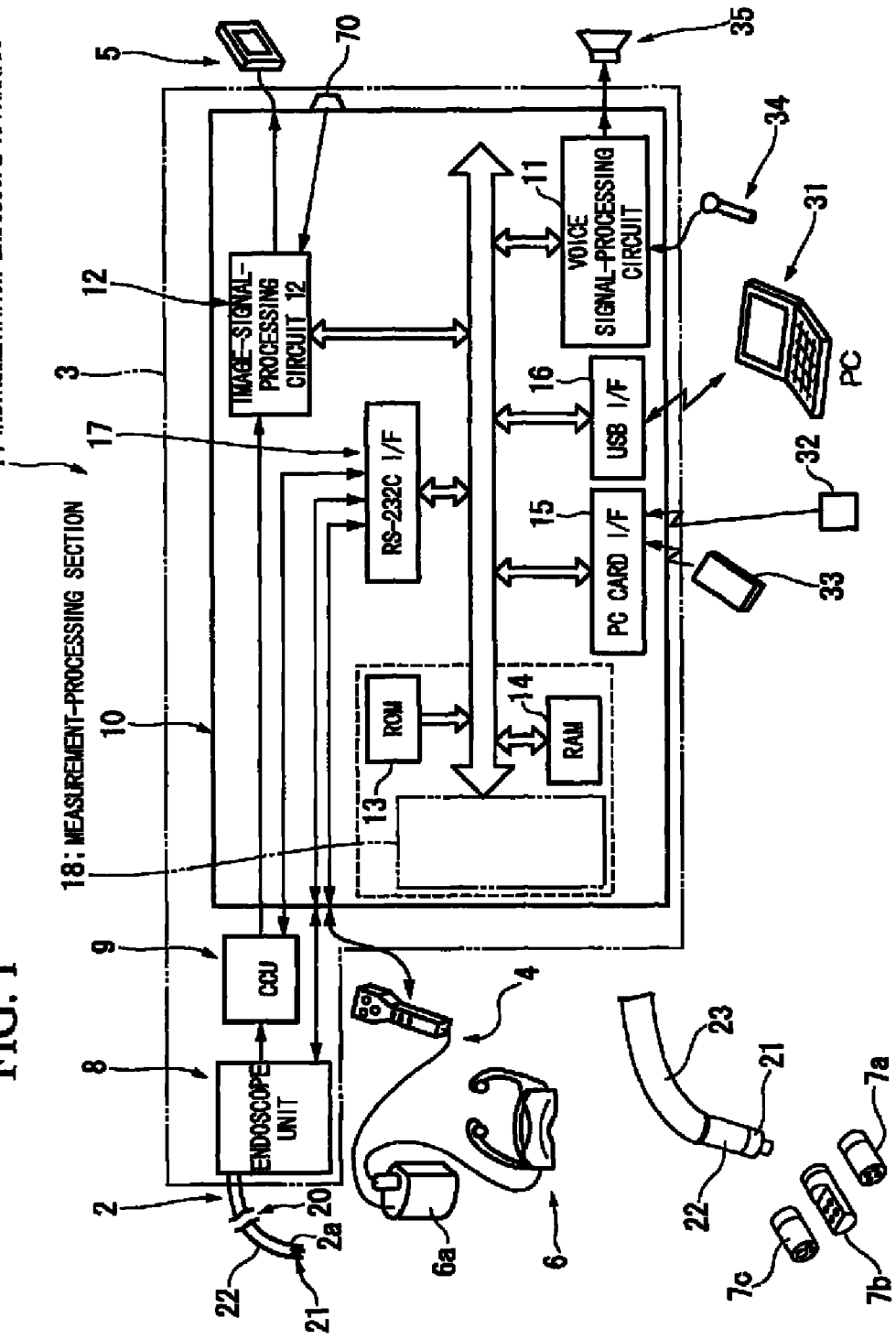
FIG. 1 is a block diagram showing a configuration of an endoscope apparatus according to a first embodiment of the present invention.

Embodiments of the present invention are explained in detail with reference to drawings as follows. FIG. 1 shows the configuration of an endoscope apparatus 1 according to an embodiment of the present invention. The endoscope apparatus 1 according to the present embodiment as shown in FIG. 1 includes: an endoscope 2; a control unit 3; a LCD monitor 5; a face mount display (FMD) 6; an FMD adapter 6a; optical adapters 7a, 7b, and 7c; an endoscope unit 8; a camera-control unit 9; and a control unit 10.

The endoscope 2 (electronic endoscope) for picking up a measurement object and generating an image signal has an elongate insertion tube 20. Formed consecutively to the insertion tube 20 in order from the distal end are: a hard distal end section 21; a bending section 22 that is capable of freely bending in, e.g., horizontal and vertical directions; and a flexible tube section 23 having flexibility. The proximal end of the insertion tube 20 is connected to the endoscope unit 8. The distal end section 21 is configured to allow various optical adapters to screw therewith detachably, e.g., the stereo optical adapters 7a and 7b having two observational perspectives, or the ordinary observation optical adapter 7c having an observational perspective.

Provided in the control unit 3 are the endoscope unit 8; an image-processing unit, i.e., the camera-control unit (hereinafter called the CCU) 9; and a control unit, i.e., the control unit 10. The endoscope unit 8 is provided with a light source apparatus that supplies illumination light necessary for observation; and a bending apparatus that bends the bending section 22 constituting the insertion tube 20. An image signal output from a solid image-pickup device 2a built in a distal end section 21 of the insertion tube 20 and input to the CCU 9 is converted into an image signal, e.g., an NTSC signal and supplied to the control unit 10.

The control unit 10 is constituted by a voice signal-processing circuit 1; an image-signal-processing circuit 12: a ROM 13; a RAM 14; a PC card interface (hereinafter called a PC card I/F) 15; a USB interface (hereinafter called a USB I/F) 16; an RS-232C interface (hereinafter called an RS-232C I/F) 17; and a measurement-processing section 18.

Supplied to the voice signal-processing circuit 11 is a voice signal collected by a microphone 34; a voice signal obtained by re-playing data stored in a storage medium, e.g., a memory card; or a voice signal generated by the measurement-processing section 18. The image-signal-processing circuit 12 carries out a process of synthesizing the image signal supplied from the CCU 9 with a display signal for use in an operation menu generated by operating the measurement-processing section 18 in order to display synthesized image including an endoscopically obtained image supplied from the CCU 9 and the graphic operation menu. In addition, the image-signal-processing circuit 12 upon providing predetermined processes to the synthesized image signal supplies the processed signal to the LCD monitor 5 in order to display an image on the screen of the LCD monitor 5.

The PC card I/F 15 provides free installation and removal of memory cards (storage medium) thereto, e.g., a PCMCIA memory card 32 or a flash memory card 33. Attaching the memory card thereto and controlling the measurement-processing section 18 enable capturing of control-processing information or image information stored in the memory card and storing of the control-processing information or the image information in the memory card.

The USB I/F 16 is an interface that provides electrical connection between the control unit 3 and a personal computer 31. Electrical connection between the control unit 3 and the personal computer 31 via the USB I/F 16 allows the personal computer 31 to supply various commands regarding display of an endoscopically obtained image and regarding control including image-processing during measurement. In addition, this enables input and output of various processing information and data between the control unit 3 and the personal computer 31.

Connected to the RS-232C I/F 17 are the CCU 9; the endoscope unit 8; and a remote controller 4 that provides commands to control the CCU 9 and to move the endoscope unit 8, etc. The remote controller 4, upon carrying out a user's command, commences communication required to control operations of the CCU 9 and the endoscope unit 8 based on the details of the operation.

Figure 2:
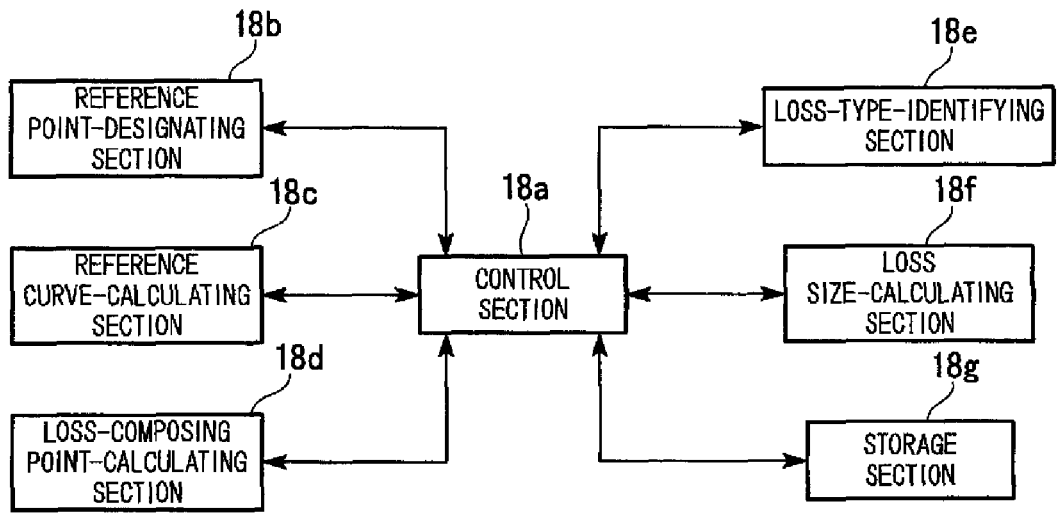
FIG. 2 is a block diagram showing a configuration of a measurement-processing section provided in the endoscope apparatus according to the first embodiment of the present invention.
Figure 2A:
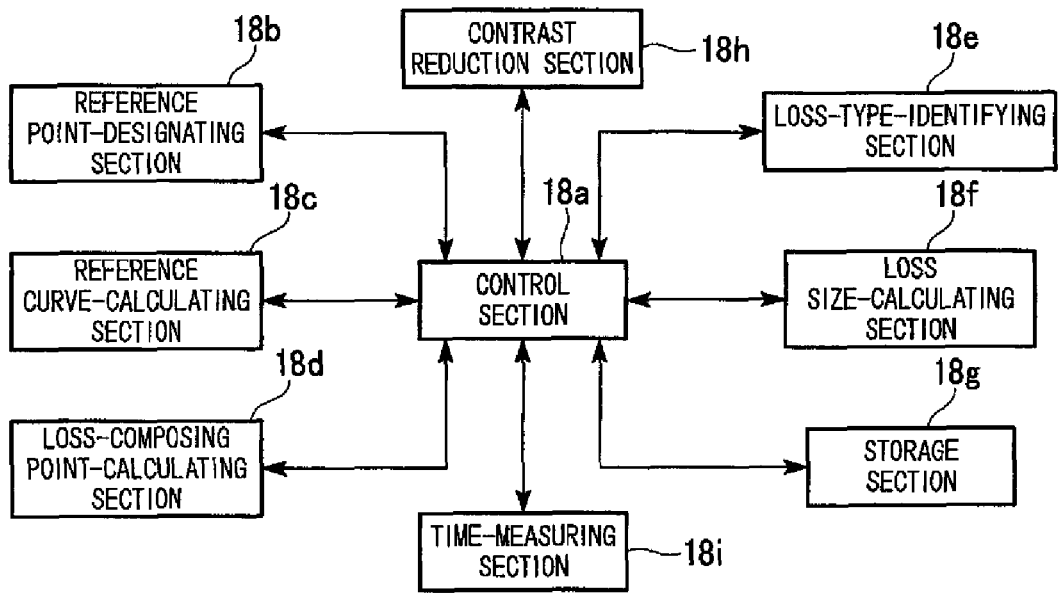

FIG. 2 illustrates the configuration of the measurement-processing section 18. As illustrated in FIG. 2, the measurement-processing section 18 is constituted by: a control section 18a; a reference point-designating section 18b; a reference curve-calculating section 18c; a loss-composing point-calculating section 18d; a loss-type-identifying section 18e; a loss size-calculating section 18f; and a storage section 18g.

The control section 18a (control means) controls components in the measurement-processing section 18. In addition, the control section 18a has a function of generating a display signal that causes the LCD monitor 5 or the face-mount display 6 (display means) to display a measurement result or an operation menu and outputting the generated signal to the image-signal-processing circuit 12.

The reference point-designating section 18b (a reference point-designating means) designates a reference point (details thereof are explained later) on a measurement object based on a signal input from the remote controller 4 or the PC 31. The reference point-designating section 18b calculates the coordinates of two any reference points input by the user who is observing the image of the measurement object displayed on the LCD monitor 5 or the face-mount display 6.

The reference curve-calculating section 18c (an outline-approximation-line-calculating means) calculates a reference curve (details of the reference curve will be explained later) that corresponds to an outline approximation line that approximates the outline of the measurement object based on the reference point designated by the reference point-designating section 18b. The loss-composing point-calculating section 18d (loss-composing points-calculating means) calculates loss-composing points (details of the loss-composing points will be explained later) that constitute a loss outline (edge) formed on the measurement object based on the reference point and the reference curve.

The loss-type-identifying section 18e (loss-type-identifying means) calculates an angle defined by two reference curves that correspond to the two reference points designated by the reference point-designating section 18b; and identifies the loss type based on the calculated angle. The loss size-calculating section 18f (loss-measurement means) measures loss size based on the loss-composing points. The storage section 18g stores various type of information that will undergo processes conducted by the measurement-processing section 18. The information stored in the storage section 18g is read out by the control section 18a and is output to appropriate components.

The contrast reduction section 18h (contrast reduction means) implements an image-contrast-reducing process based on an image signal. To be more specific, the contrast reduction section 18h extracts brightness data from the image; generates e.g., a grayscale image having 256 brightnesses; and converts the grayscale image into an image having two, four, or eight brightnesses. In the following explanations, the contrast reduction section 18h binarizes the signal level of a picked up image and converts the image into a binary image (a black-and-white image). A time-measuring section 18i (time-measuring means) implements time measurement based on the instruction supplied from the control section 18a.

Figure 3:
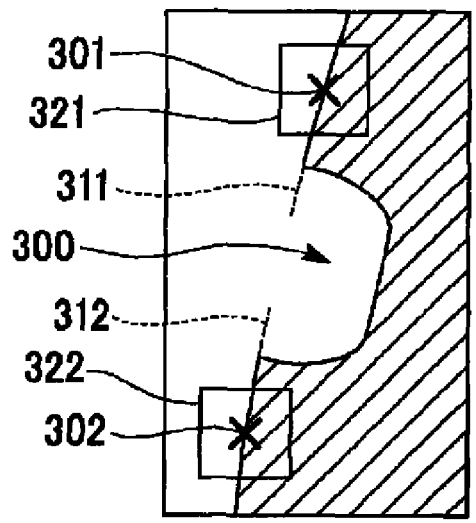
FIG. 3 shows for reference a reference point, a reference curve, and a reference point area in the first embodiment of the present invention.

Terms used in the present embodiment will be explained as follows. To start with, a reference point, a reference curve, and a reference point area will be explained with reference to FIG. 3. Reference points 301 and 302 on the displayed screen are actually designated by the user. As illustrated in FIG. 3, these points, disposed on both sides of a loss 300, are on edges that are free from losses.

Reference curves 311 and 312 approximating the outline of the measurement object (edge) are calculated based on the two reference points 301 and 302. In particular, a reference curve calculated in the present embodiment is a distortion-corrected curve obtained by compensating distortion of an image-pickup optical system provided to the distal end of the endoscope 2 (in the distal end section 21 and distortion of an image-pickup optical system (optical adapters 7a, 7b, and 7c) separately provided to the distal end of the endoscope 2.

Reference point areas 321 and 322 indicate image areas that extract an edge around the reference point in order to obtain the reference curves 311 and 312. The distortion-corrected curve may be calculated based on appropriately established size of reference point areas 321 and 322.

Subsequently, loss type, loss-starting point, loss-ending point, loss apex, and loss-composing points will be explained with reference to FIGS. 4 and 5. Two types of loss, i.e., a side loss and an apex loss undergo the measurement according to the present embodiment.

Figure 4:
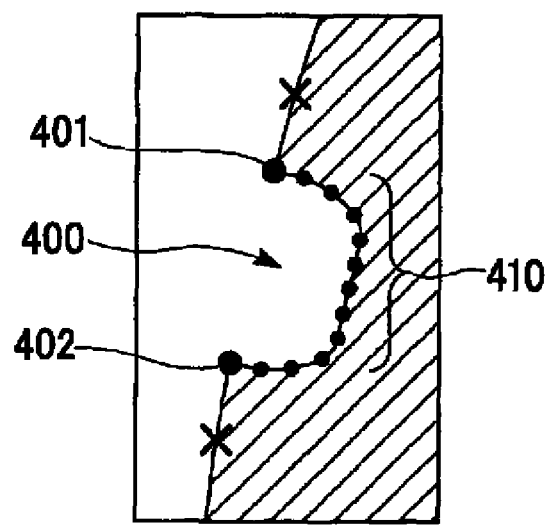
FIG. 4 shows for reference a side loss-starting point, a side-loss-ending point, and a side-loss-composing point with respect to the first embodiment of the present embodiment.
Figure 5:
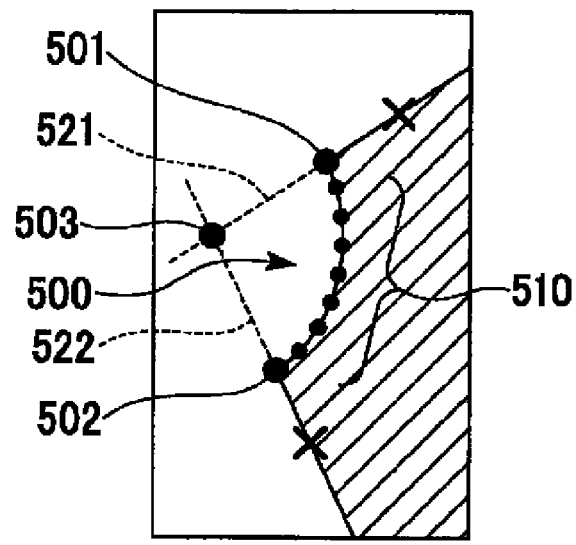
FIG. 5 shows for reference an apex-loss-starting point, an apex-loss-ending point, an apex, and an apex-loss-composing point with respect to the first embodiment of the present embodiment.

FIG. 4 illustrates a loss 400 formed on an edge side measurement object and FIG. 5 illustrates an apex loss 500 formed on an apex defined by edge lines of a measurement object.

Loss-starting points 401 and 501 displayed on a measurement screen undergo a loss calculation which will be explained later and are recognized first as constituting a loss. Loss-ending points 402 and 502 are recognized last as forming the loss. A loss apex 503 is recognized as a cross-point of reference curves 521 and 522 forming a part of the apex loss 500. Loss-composing points 410 and 510 each including the loss-starting point, loss-ending point, and loss apex constitute a loss edge formed on the measurement object.

Loss size will be explained next with reference to FIGS. 6 and 7. Loss size is a parameter that represents a detected loss size. Size of a side loss undergoing calculation of the present embodiment includes width, depth, and area, and size of an apex loss includes width, depth, and area. To be more specific, a width of the loss is a spatial distance between a loss-starting point and a loss-ending point. A depth of the loss is a spatial distance between a predetermined loss-composing point and a line joining the loss-starting point to the loss-ending point. A spatial distance between the loss apex and the loss-starting point, and a spatial distance between the loss apex and the loss-ending point indicate a loss side. The loss area indicates an area of a space surrounded by all of the loss-composing points.

Figure 6:
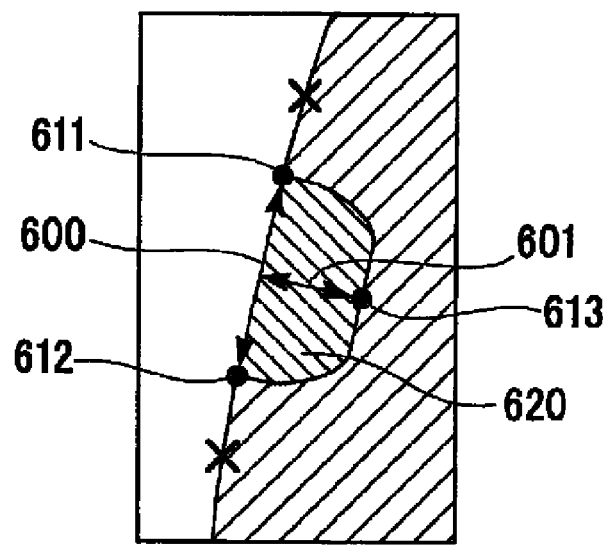
FIG. 6 shows for reference a side-loss width, a side-loss depth, and a side-loss area with respect to the first embodiment of the present embodiment.

FIG. 6 describes loss size with respect to a side. A loss width 600, obtained by a loss calculation which will be explained later, indicates a spatial distance between a loss-starting point 611 and a loss-ending point 612. A loss depth 601 indicates a spatial distance between a predetermined loss-composing point 613 and a line between the loss-starting point 611 and the loss-ending point 612. The loss area indicates the spatial area 620 surrounded by all the loss-composing points including non-illustrated loss-composing points.

Figure 7:
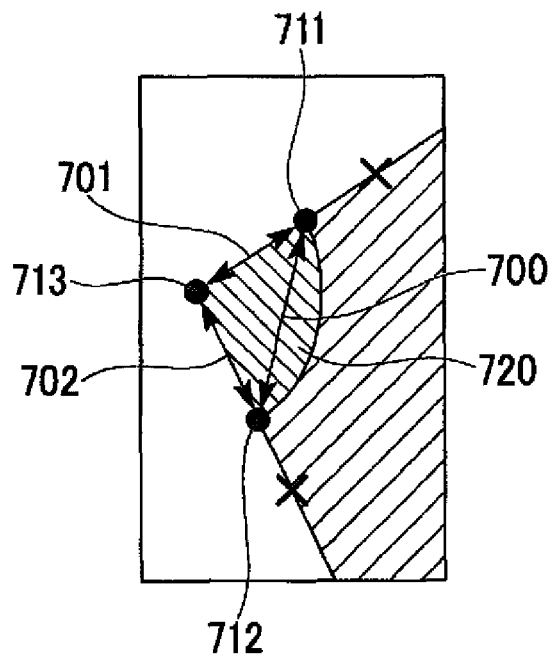
FIG. 7 shows for reference the apex-loss width, the length of the side, and a loss area with respect to the first embodiment of the present embodiment.

FIG. 7 describes loss size with respect to an apex. A loss width 700, obtained by a loss calculation which will be explained later, is a spatial distance between a loss-starting point 711 and a loss-ending point 712. A loss side 701 indicates a spatial distance obtained between a loss apex 713 and the loss-starting point 711. A loss side 702 indicates a spatial distance obtained between the loss apex 713 and the loss-ending point 712. The loss area indicates a spatial area 720 surrounded by all the loss-composing points including non-illustrated loss-composing points.

Figure 8:
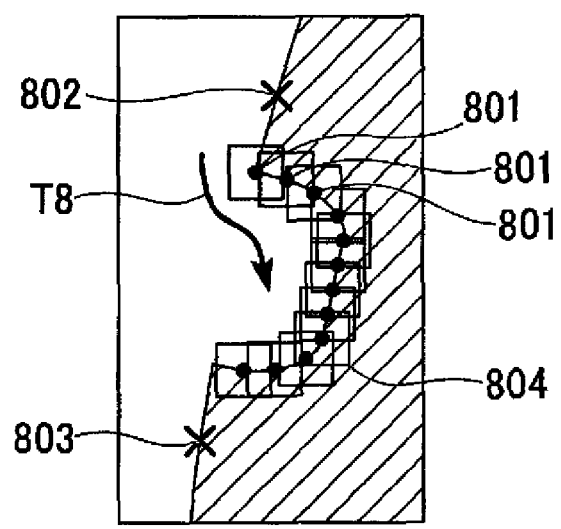
FIG. 8 shows a measurement point and a measurement area in the first embodiment of the present invention.

A measurement point and a measurement point area will be explained next with reference to FIG. 8. Measurement points 801 on the edge of a measurement object on a displayed measurement screen undertake sequential search (exploration) in a direction from a first reference point 802 to a second reference point 803 in a loss calculation which will be explained later. In addition, some of the searched measurement points are recognized as loss-composing points.

A measurement point area 804 indicates an image area for use in searching of the measurement point 801 and extracting of the edge around the measurement point. The edge may be extracted based on an appropriately established size of the measurement point area 804.

Figure 9:
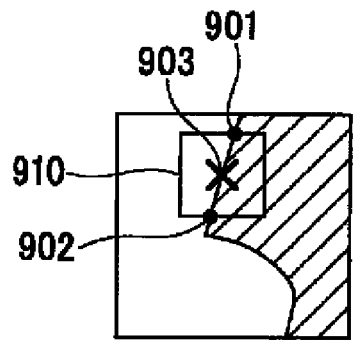
FIG. 9 shows a characteristic point in the first embodiment of the present invention.
Figure 10:
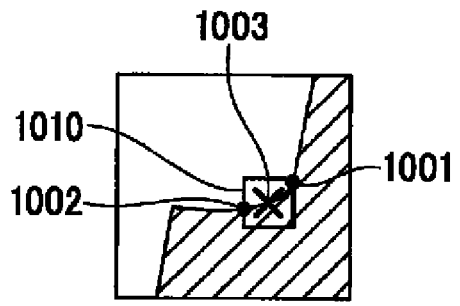
FIG. 10 shows the characteristic point in the first embodiment of the present invention.

Characteristic points will be explained next with reference to FIGS. 9 and 10. Characteristic points 901 and 902 on an edge are extracted within a reference point area 910 including a reference point 903. Also, characteristic points 1001 and 1002 on an edge are extracted within a measurement point area 1010 including a measurement point 1003. The characteristic points 901 and 902 extracted within the reference point area 910 are used for calculating a reference curve in a loss calculation which will be explained later. Some of the characteristic points extracted within. e.g., the measurement point area 1010 are selected as measurement points in the loss calculation.

Figure 11:
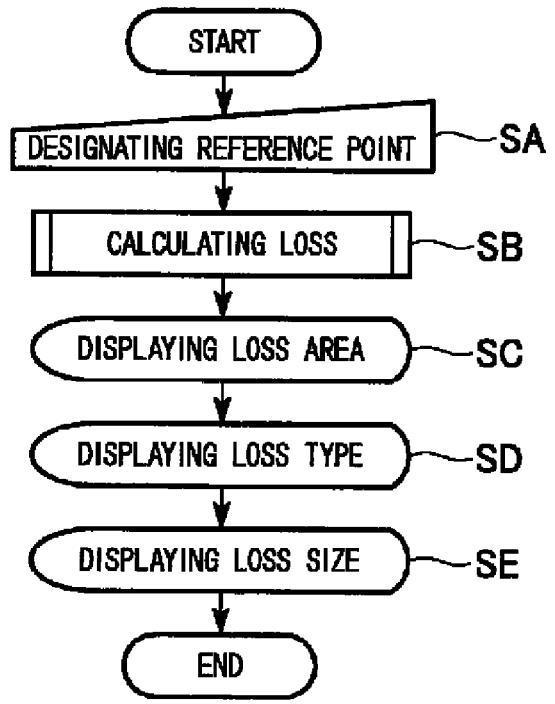
FIG. 11 is a flowchart showing a loss measurement process in the first embodiment of the present invention.
Figure 12:
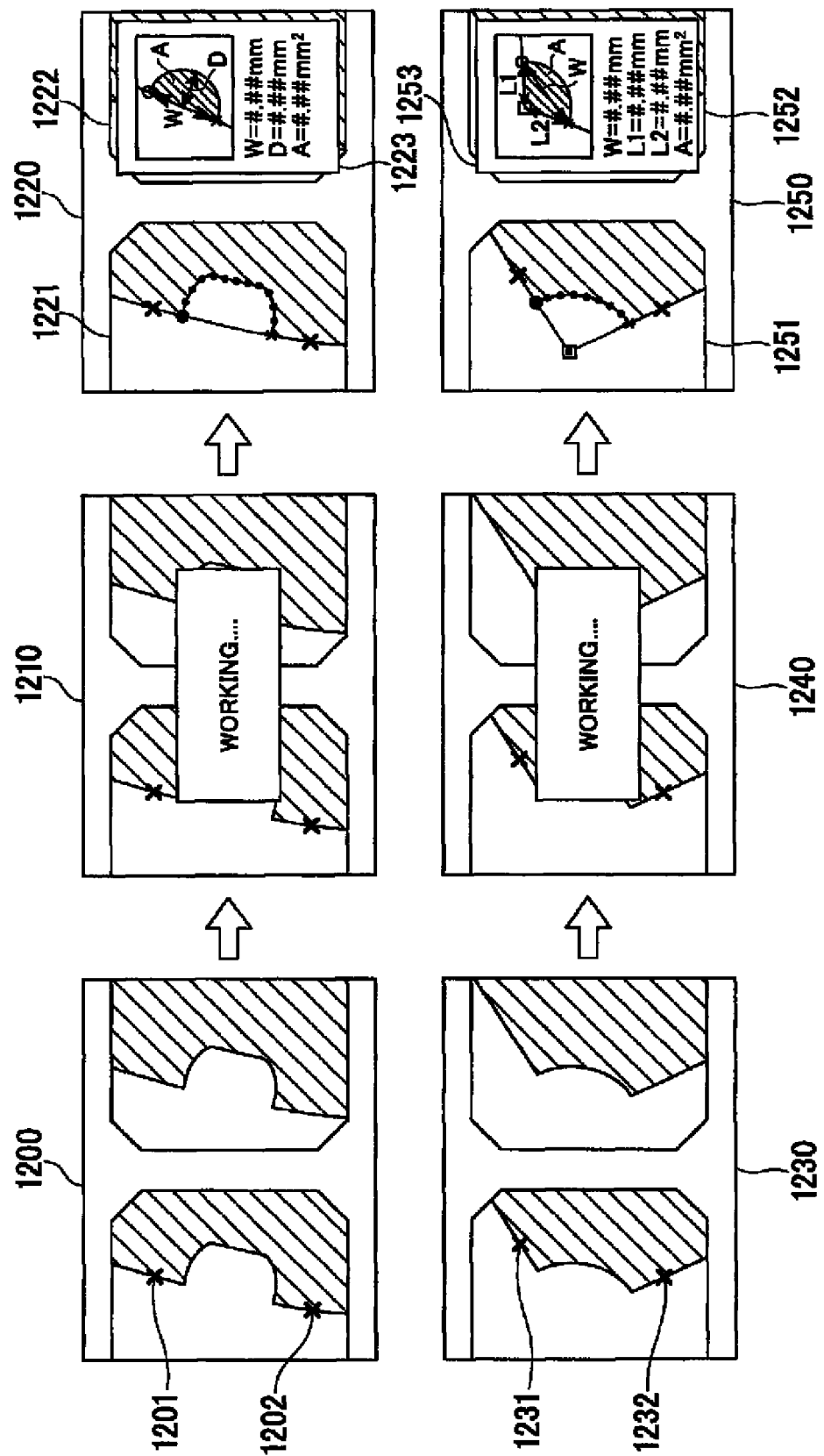
FIG. 12 shows for reference a measurement screen displayed during a loss measurement in the first embodiment of the present invention.

A procedure of loss measurement according to the present embodiment will be explained next. Loss measurement and a measurement screen will be explained as follows with reference to FIGS. 11 and 12. FIG. 11 describes a procedure of the loss measurement. FIG. 12 shows a measurement screen. Measurement screens, shown in e.g., FIG. 12, may omit an operation menu. As illustrated in FIG. 12, measurement images 1200, 1210, and 1220 indicate that a measurement object is a side loss, and measurement images 1230, 1240, and 1250 indicate that a measurement object is an apex loss.

The present embodiment implements stereoscopic loss measurement. A measurement object picked up by a stereoscopic optical adapter attached to the distal end section 21 of the endoscope 2 based on the stereoscopic measurement is viewed as a pair of images generated on a measurement screen.

The loss measurement first inputs details of two reference points, displayed on a measurement screen of the LCD monitor 5 or the face-mount display 6 and designated by a user who operates the remote controller 4 or the PC 31, to the measurement-processing section 18 (step SA). Preferably, reference points selected by the user may be disposed across a loss on the edge free from the loss. Reference points 1201 and 1202, and reference points 1231 and 1232 that are found in left images in FIG. 12 are designated.

Subsequently, the measurement-processing section 18 implements a loss calculation based on the coordinates of the designated reference points (step SB). The loss calculation carries out a calculation with respect to coordinates of the loss-composing points and loss size; and identification of loss type. The measurement images 1210 and 1240 indicate measurement screens during calculation. Details of the loss calculation will be explained later.

The detected loss area upon ending the loss calculation is displayed on the measurement screen based on an instruction by the measurement-processing section 18 (step SC), and simultaneously the loss type and the loss size are displayed (steps SD to SE). As illustrated in FIG. 12, the loss area is displayed on a left image 1221 of the measurement image 1220 and on a left image 1251 of the measurement image 1250. To be more specific, the calculated loss-composing points in the displayed image are joined by lines. In addition, cursors "○", "*", and "☐" indicate a loss-starting point, a loss-ending point, and an apex of the loss-composing points, respectively.

In addition, images of the detected loss type are displayed in upper sections of result windows 1223 and 1253 of right images 1222 and 1252 in the measurement images 1220 and 1250. In addition, letters indicating the detected loss size are displayed in lower sections of the result windows 1223 and 1253 of the right images 1222 and 1252 in the measurement images 1220 and 1250.

Figure 13:
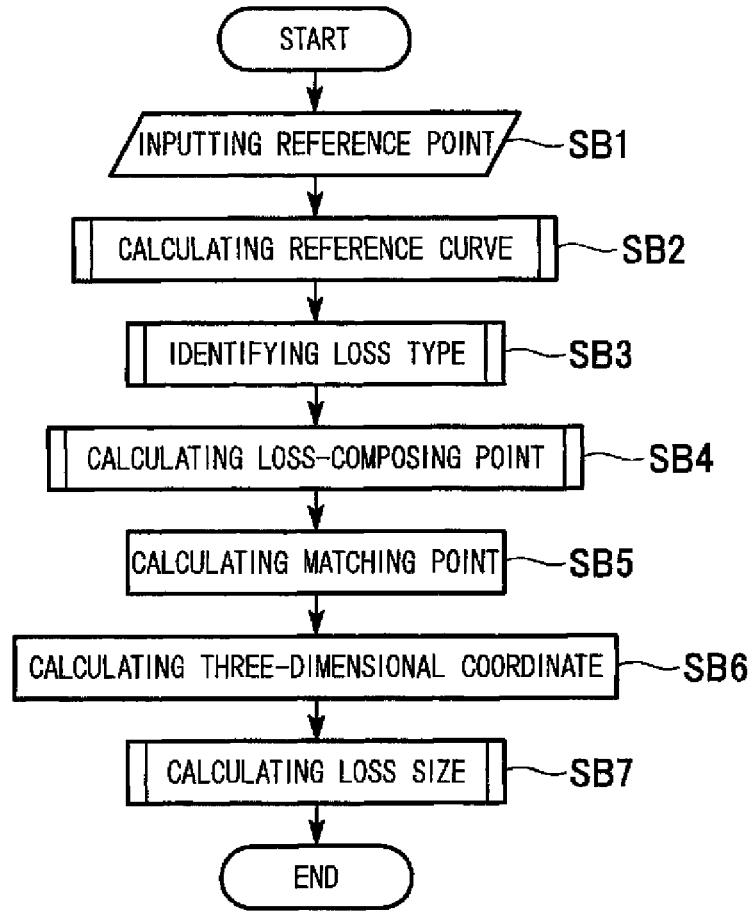
FIG. 13 is a flowchart showing a loss calculation in the first embodiment of the present invention.

A procedure of loss calculation in step SB described in FIG. 11 will be explained next with reference to FIG. 13. When details with respect to positions of the two reference points designated by the user in the left image are input into the measurement-processing section 18, the reference point-designating section 18b calculates image coordinates of the two reference points (two-dimensional coordinates on an image displayed on the LCD monitor 5 or the face-mount display 6) (step SB1).

Subsequently, the reference curve-calculating section 18c calculates two reference curves based on the image coordinates of the two reference points (step SB2).

Subsequently, the loss-type-identifying section 18e calculates the angle defined by the two reference curves and identifies the loss type corresponding to the calculated angle (step SB3). Subsequently, the loss-composing point-calculating section 18d calculates the image coordinates of the loss-composing points based on the image coordinates of the two reference points (and using reference curves in the case of an apex loss) (step SB4).

Subsequently, the loss-composing point-calculating section 18d calculates the image coordinates of matching points in the right image corresponding to the calculated loss-composing points in the left images and further calculates the spatial coordinates of the loss-composing points (real-space three-dimensional coordinates) based on the calculated loss-composing points and the image coordinates of the matching points of the calculated loss-composing points (step SB6).

A method for calculating spatial coordinates is the same as that disclosed in Japanese Unexamined Patent Application, First Publication No. 2004-49638. The loss size-calculating section 18f finally calculates the loss size corresponding to the loss type based on the spatial coordinates of the calculated loss-composing points (step SB7).

Figure 14:
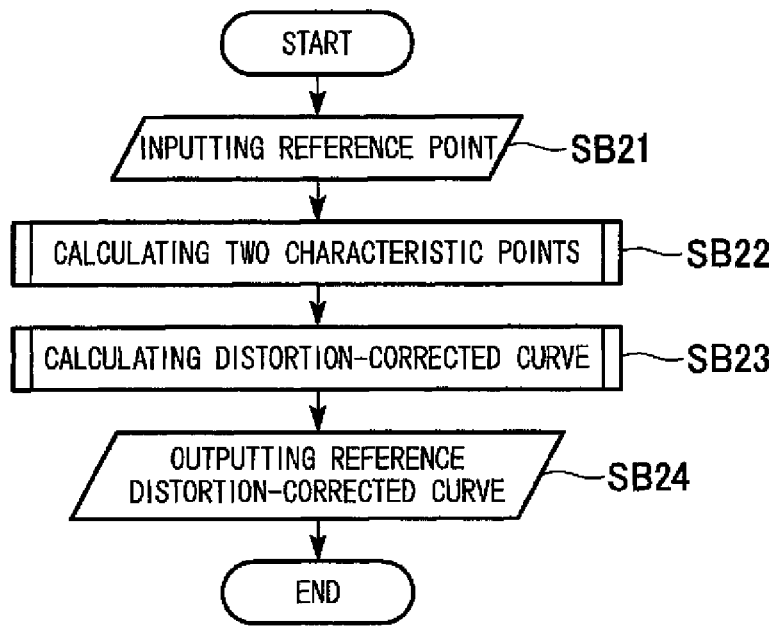
FIG. 14 is a flowchart showing a calculation of a reference curve in the first embodiment of the present invention.

A procedure of calculating a reference curve in the step SB2 of FIG. 12 will be explained next with reference to FIG. 14. The reference curve-calculating section 18c, upon carrying out input of the image coordinates of the two reference points calculated by the reference point-designating section 18b (step SB21), calculates two characteristic points to each reference point based on the image coordinate of the input reference point (step SB22).

Subsequently, the reference curve-calculating section 18c calculates a distortion-corrected curve, which has undergone distortion compensation with respect to the image-pickup optical system, based on the two characteristic points (step SB23). Accordingly, two distortion-corrected curves are calculated corresponding to the two reference points. The reference curve-calculating section 18c finally outputs the details of the reference curves, i.e., details of the distortion-corrected curve (indicated by the image coordinates of points that form the curve, or a formula of the curve), to the control section 18a (step SB24).

Figure 15:
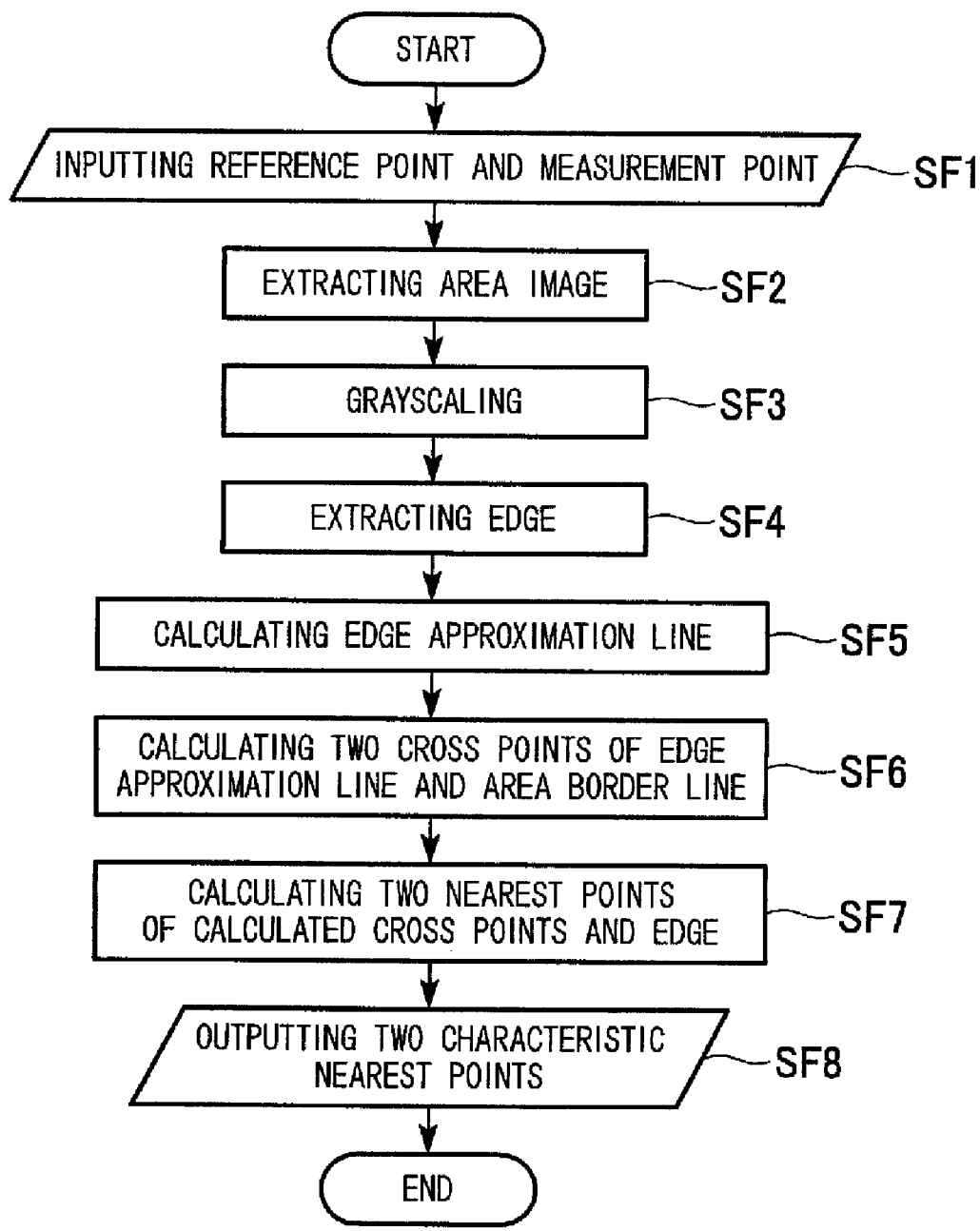
FIG. 15 is a flowchart showing a calculation of the characteristic point in the first embodiment of the present invention.

A procedure of calculating characteristic points in the step SB22 will be explained with reference to FIG. 15 as follows. The calculation of characteristic points is carried out not only when a reference curve is calculated but also when loss-composing points are calculated. The calculation of characteristic points will be explained in summary here while the calculation of the loss-composing points will be explained later.

Figure 16:
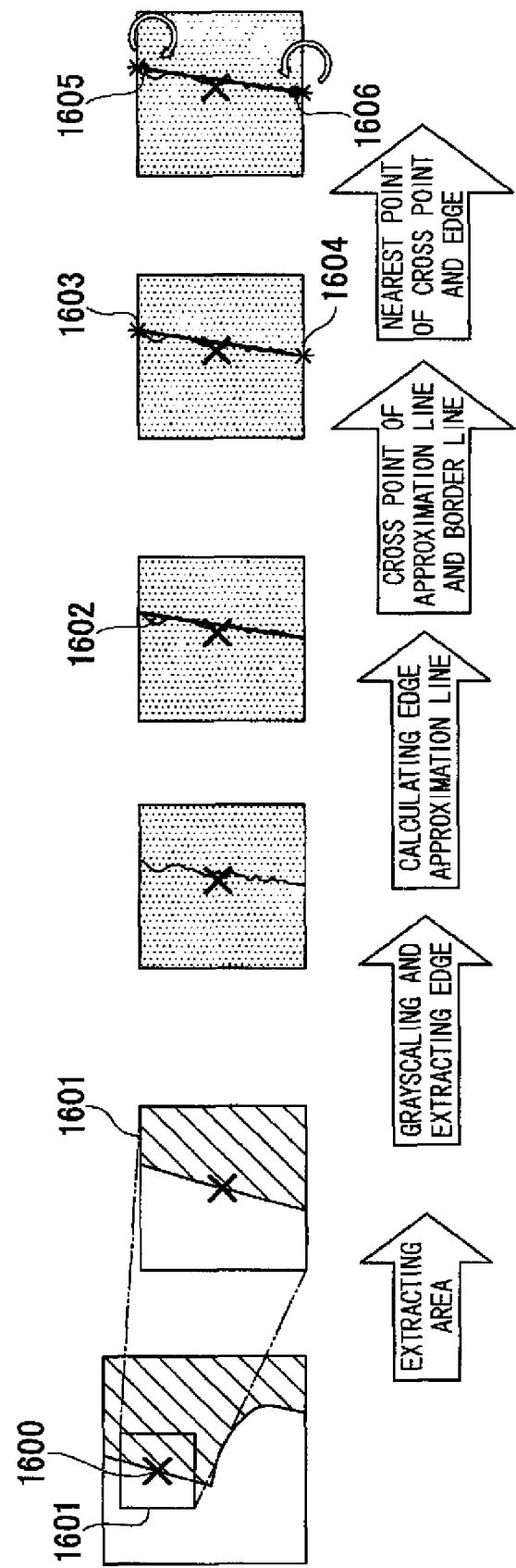
FIG. 16 shows for reference a calculation of the characteristic point in the first embodiment of the present invention.
Figure 17:
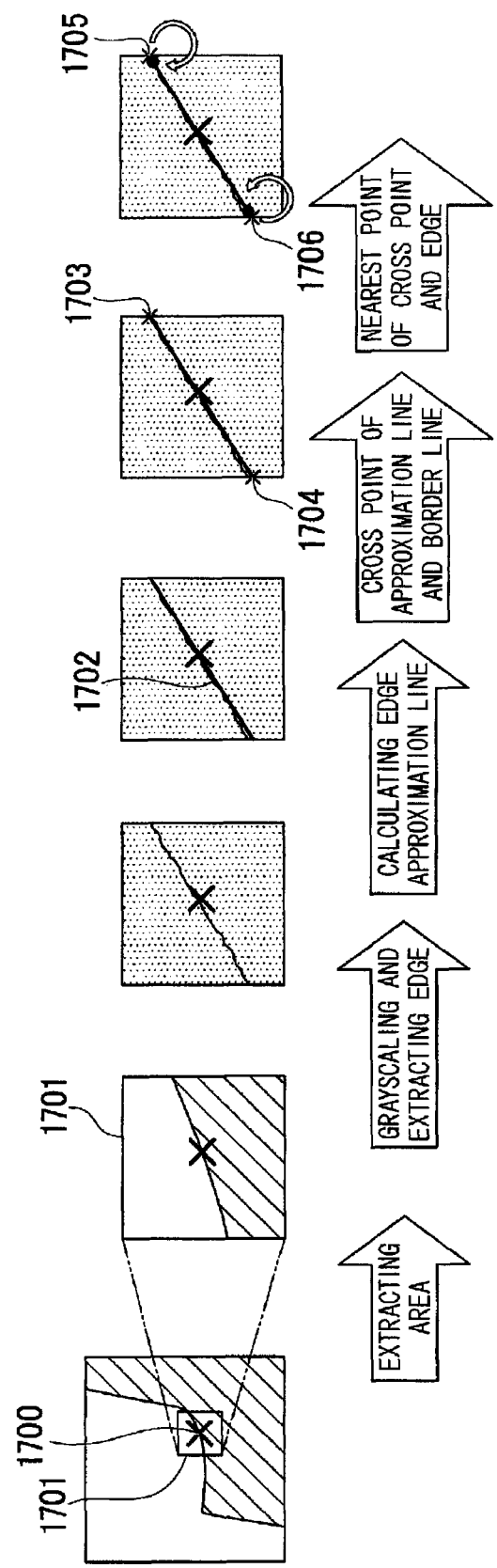
FIG. 17 shows for reference the calculation of the characteristic point in the first embodiment of the present invention.

FIGS. 16 and 17 illustrating the calculation of characteristic points schematically are also referred to if necessary. FIG. 16 illustrates a procedure of calculating characteristic points around a reference point, and FIG. 17 illustrates a procedure of calculating characteristic points around a measurement point.

Upon receiving the image coordinate of the reference point or the image coordinate of the measurement point (step SF1), an area image within a reference point area or the measurement point area is extracted based on the input image coordinate of the reference point or the image coordinate of the measurement point (step SF2). Accordingly, an area image 1601 within the reference point area including a reference point 1600, or an area image 1701 within the measurement point area including a measurement point 1700 is extracted.

Subsequently, the extracted area image is converted to gray scale (step SF3), and edge extraction is conducted to the grayscale image (step SF4). Subsequently, an approximation line of the extracted edge is calculated (step SF5), and then two cross-points of the approximated line with the calculated edge approximation line and the area border line are calculated (step SF6). Accordingly, an edge approximation line 1602 or an edge approximation line 1702 is obtained. Cross-points 1603 and 1604 formed by the edge approximation line 1602 and the area border line, or cross-points 1703 and 1704 formed by the edge approximation line 1702 and the area border line are calculated.

Finally, two nearest points, calculated with respect to the calculated cross-points and the extracted edge (step SF7), are characteristic points that are output to the control section 18a (step SF8). Accordingly, the characteristic point, i.e., nearest points 1605 and 1606 corresponding to the cross-points 1603 and 1604, or the nearest points 1705 and 1706 corresponding to the cross-points 1703 and 1704 are output.

Preferably, edge extraction should adapt a method that can minimize noise in an extracted image since an edge approximation line is calculated after the edge extraction of the step SF4. A usable first-derivative filter may be e.g., a Sobel filter, a Prewitt filter, or a gradient filter, and a usable second-derivative filter may be e.g. a Laplacian filter.

Alternatively, edge extraction may be conducted by combining filters corresponding to processes, e.g., dilation, erosion, subtraction, and noise-reduction. A method that is necessary to binarize this grayscale image state may use a fixed threshold value. Also, a method for changing a threshold based on brightness of the grayscale image may be a P-tile method, mode method, or discriminant analysis method.

Also, the edge approximation line is calculated in the step SF5 by using, e.g., a simple least squares method that is based on details of the edge extracted in the step SF4. It should be noted that curve approximation using quadratic function may be conducted in contrast to linear approximation conducted with respect to edge shape as explained above. Curve approximation may provide more accurate calculation of characteristic points if the edge shape is curved rather than straightened.

A procedure of calculating distortion-corrected curves in step SB23 of FIG. 14 will be explained next. The endoscope 2 adapted to the endoscope apparatus 1 according to the present embodiment measures optical data of the objective optical system that is unique to each endoscope 2. The measured optical data is stored in, e.g., the flash memory card 33. The use of optical data allows a measurement image to be converted into a distortion-corrected image with respect to the image-pickup optical system.

Figure 18:
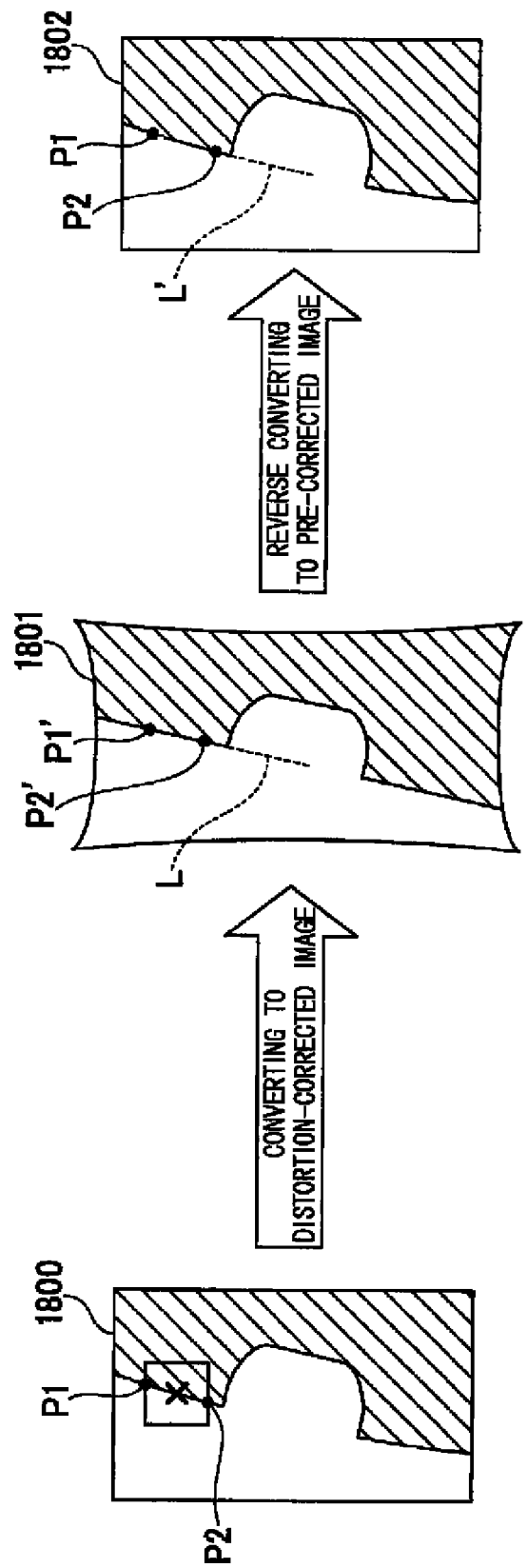
FIG. 18 shows for reference a method for calculating a distortion-corrected curve in the first embodiment of the present invention.

A method for calculating a distortion-corrected curve will be explained as follows with reference to FIG. 18. An original image 1800 is the image of a measurement object. Points P1 and P2 are two characteristic points calculated in step SB22 of FIG. 14. Converting the original image 1800 by using the optical data obtains a distortion-corrected image 1801. Points P1' and P2' are post-conversion points of P1 and P2, respectively.

Reverse conversion conducted with respect to each pixel point on a line L causes the line L to be converted to a curve L' on the original image 1802 where the line L indicates a line obtained by connecting the point P1' to P2' on the distortion-corrected image 1801. Details of the curve L', i.e., distorted line passing through the points P1 and P2 is output to the control section 18a. Details of optical data, the method of producing thereof, and a distortion-correcting Method are the same as those disclosed in Japanese Unexamined Patent Application, First Publication No. 2004-49638.

Figure 19:
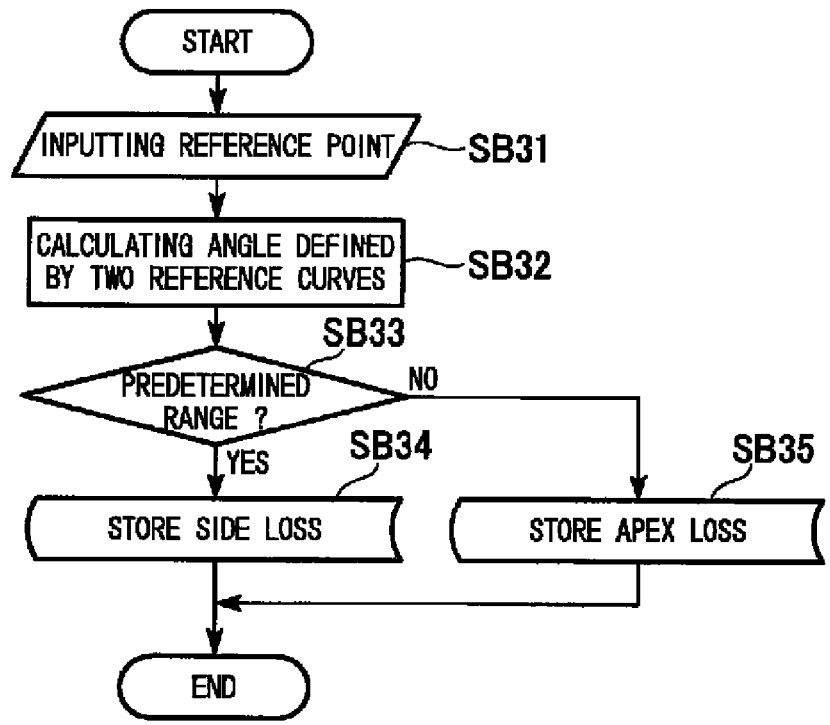
FIG. 19 is a flowchart showing a procedure of loss type identification in the first embodiment of the present invention.

A procedure of loss type identification in the step SB3 of FIG. 13 will be explained next with reference to FIG. 19. The loss-type-identifying section 18e upon undertaking the input of details of the two reference curves from the control section 18a (step SB31) causes the loss-type-identifying section 18e to calculate the angle defined by the two reference curves (step SB32).

Subsequently, the loss-type-identifying section 18e determines as to whether or not the angle defined by the two reference curves is in a predetermined range (step SB33).

In a case where the angle defined by the two reference curves is in the predetermined range (e.g., the angle is close to 180°), the loss-type-identifying section 18e upon determining that a loss is of edge-type outputs the loss identification result to the control section 18a. The control section 18a stores the loss identification result in the storage section 18g (step SB34). In a case where the angle defined by the two reference curves is not in the predetermined range (e.g., the angle is close to 90°), the loss-type-identifying section 18e upon determining that a loss is of apex-type outputs the loss identification result to the control section 18a. The control section 18a stores the loss identification result in the storage section 18g (step SB35).

Figure 20:
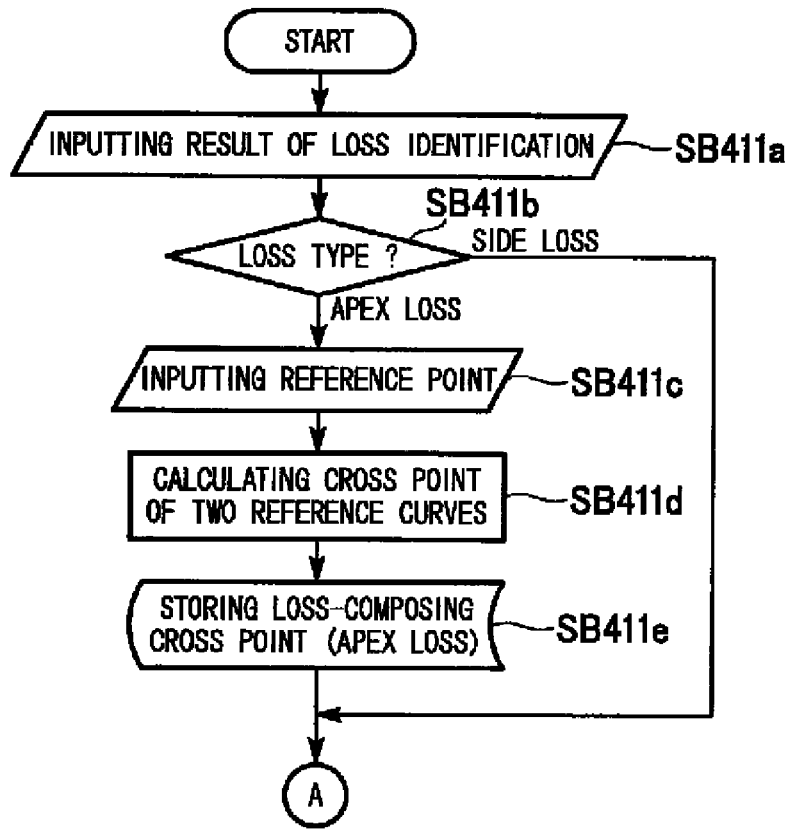
FIG. 20 is a flowchart showing a procedure of processing a loss apex calculation in the first embodiment of the present invention.

A procedure of calculating loss-composing points in step SB24 of FIG. 13 will be explained next. Calculation of the loss-composing points includes processes of loss-apex-calculation, loss-starting-point calculation, two-types-of-measurement-points-calculation, and loss-ending-point-calculation. The loss-apex-calculation will be explained first with reference to FIG. 20.

The loss-composing point-calculating section 18d upon undertaking the input of the loss identification result from the control section 18a (step SB411a) identifies the loss type based on the identification result (step SB411b). If the loss is of apex type, the details of the two reference curves are input by the control section 18a (step SB411c).

The loss-composing point-calculating section 18d calculates the cross-point of the two reference curves based on the input details (step SB411d) and outputs the image coordinate of the calculated cross-point. The control section 18a stores the image coordinate of the cross-point of the two reference curves, i.e., the image coordinate of the loss-composing points (loss apex) in the storage section 18g (step SB411e). Subsequently, the procedure moves to a first-measurement-point-calculation described in FIG. 21. Also, if the loss is of edge-type, the procedure subsequent to the step SB411b moves to the first-measurement-point-calculation described in FIG. 21.

Figure 21:
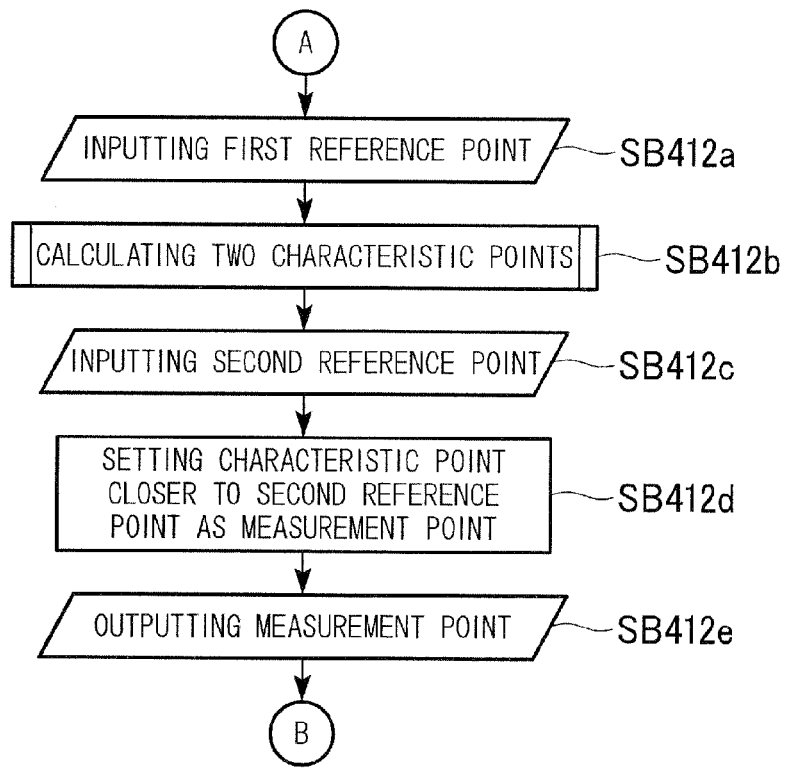
FIG. 21 is a flowchart showing a procedure of a first-measurement-point-calculation in the first embodiment of the present invention.
Figure 22:
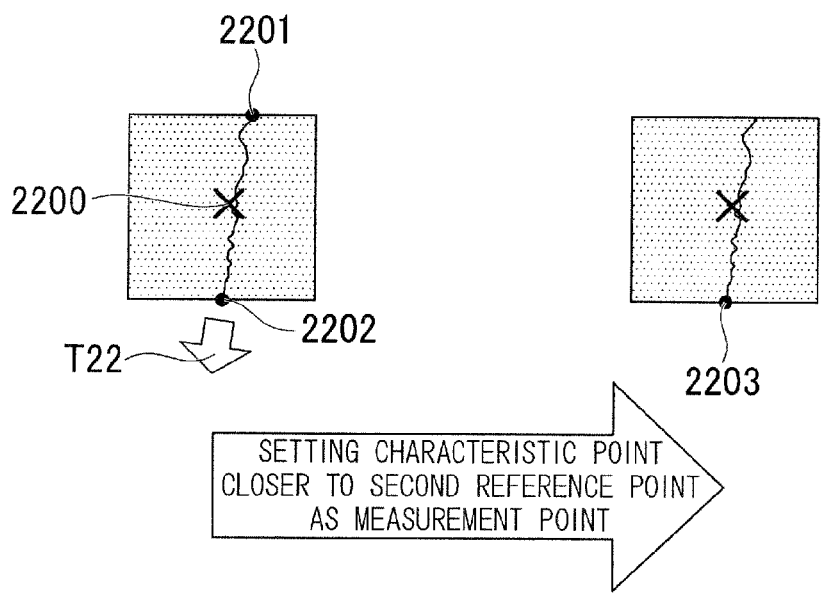
FIG. 22 shows for reference the first-measurement-point-calculation in the first embodiment of the present invention.

A procedure of the first-measurement-point-calculation will be explained next with reference to FIG. 21. FIG. 22 schematically showing a procedure of the first-measurement-point-calculation will be referred to if necessary. The loss-composing point-calculating section 18d upon carrying out the input of an image coordinate of a first one of two reference points that have been designated first (step SB412a) by the user executes the calculation of the characteristic point as shown in FIG. 15 and calculates the two characteristic points (step SB412b). This results in calculating two characteristic points 2201 and 2202 corresponding to a first reference point 2200.

Subsequently, the image coordinates of a second reference point are input by the control section 18a (step SB412c). The loss-composing point-calculating section 18d calculates a two-dimensional distance between the two characteristic points and the second reference point. The characteristic point closer to the second reference point are a next measurement point (step SB412d).

In a case where a direction of the second reference point is a direction 122 in FIG. 22, one of the two characteristic points 2201 and 2202, i.e., the characteristic point 2202 is a next measurement point 2203.

Subsequently, the loss-composing point-calculating section 18d outputs the image coordinate of the calculated measurement point to the control section 18a. The control section 18a stores the image coordinate of the measurement point in the storage section 18g (step SB412e). Subsequently, the procedure moves to a loss-starting-point-calculation described in FIG. 23.

Figure 23:
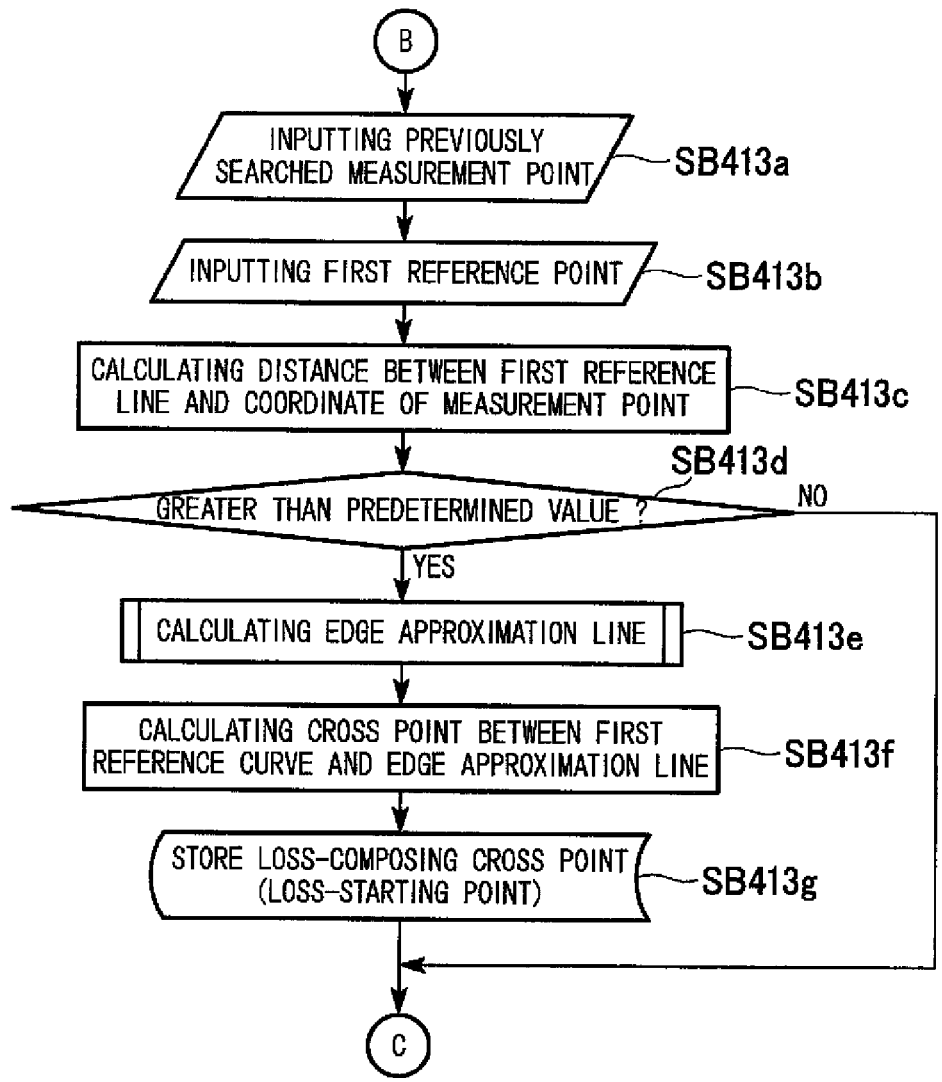
FIG. 23 is a flowchart showing a loss-starting-point-calculation in the first embodiment of the present invention.
Figure 24:
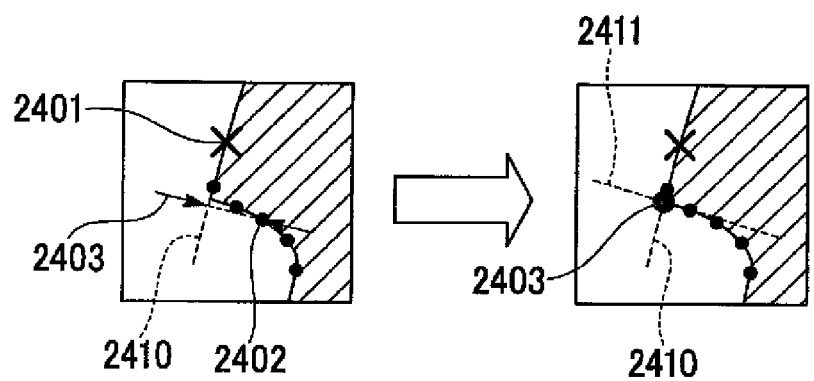
FIG. 24 shows for reference a procedure of the loss-starting-point-calculation in the first embodiment of the present invention.

The loss-starting-point-calculation will be explained next with reference to FIG. 23. FIG. 24 schematically showing a procedure of the loss-starting-point-calculation will be referred if necessary. To start with, the image coordinate of the previously obtained measurement point is input by the control section 18a (step SB413a). Details of the first reference curve calculated based on the first reference point are input by the control section 18a (step SB413b).

Subsequently, the loss-composing point-calculating section 18d upon calculating the two-dimensional distance between the first reference curve and the measurement point (step SB413c) determines as to whether or not the calculated two-dimensional distance is a predetermined value or greater (step SB413d). In a case where the calculated two-dimensional distance is greater than the predetermined value, the loss-composing point-calculating section 18d calculates an edge approximation line that is obtained by approximating the edge of the measurement object (step SB413e). An edge approximation line 2411 is calculated in a case of, e.g., FIG. 24 where the two-dimensional distance D24 between a first reference curve 2410 and a measurement point 2402 calculated based on the first reference point 2401 is the predetermined value or greater.

Subsequently; the loss-composing point-calculating section 18d calculates the cross-point of the first reference curve and the edge approximation line (step SB413f). Accordingly, the cross-point 2403 of the first reference curve 2410 and the edge approximation line 2411 is calculated.

Figure 25:
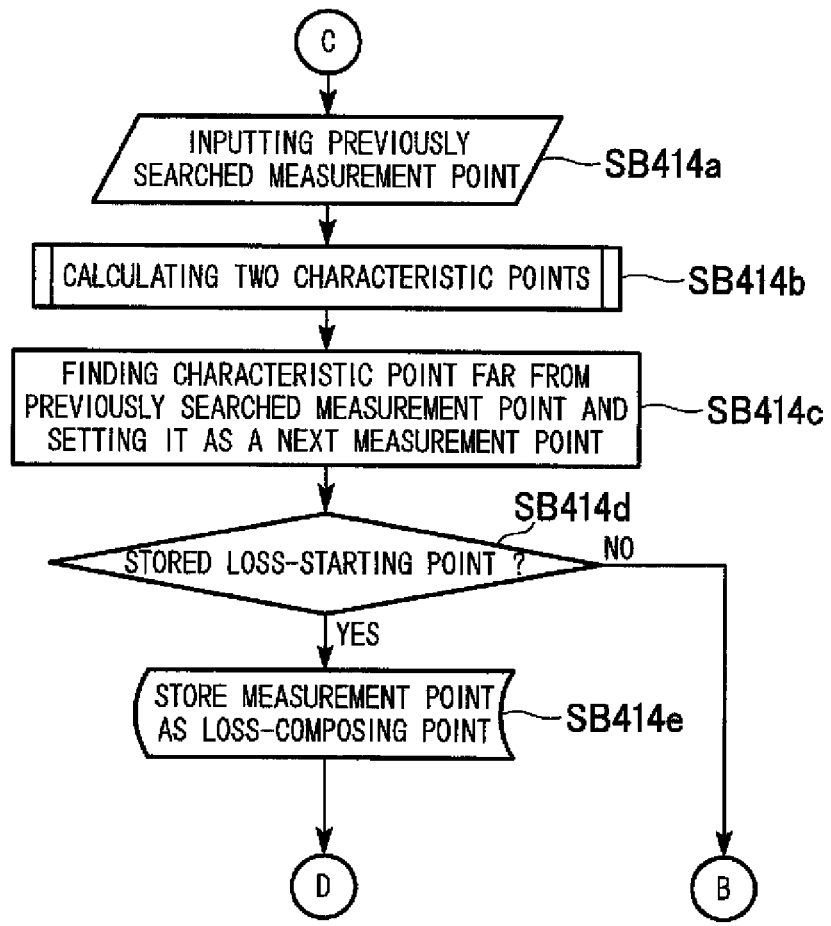
FIG. 25 is a flowchart showing a procedure of a second-measurement-point-calculation in the first embodiment of the present invention.

Subsequently, the loss-composing point-calculating section 18d outputs the image coordinate of the calculated cross-point to the control section 18a. The control section 18a stores the image coordinate of the cross-point, i.e., the image coordinate of the loss-composing points (loss-starting point) in the storage section 18g (step SB413g). Subsequently, the procedure moves to a second-measurement-point-calculation described in FIG. 25. Also, the procedure subsequent to the step SB413d moves to the second-measurement-point-calculation as shown in FIG. 25 in a case where the two-dimensional distance calculated in the step SB413c is smaller than the predetermined value.

Figure 26:
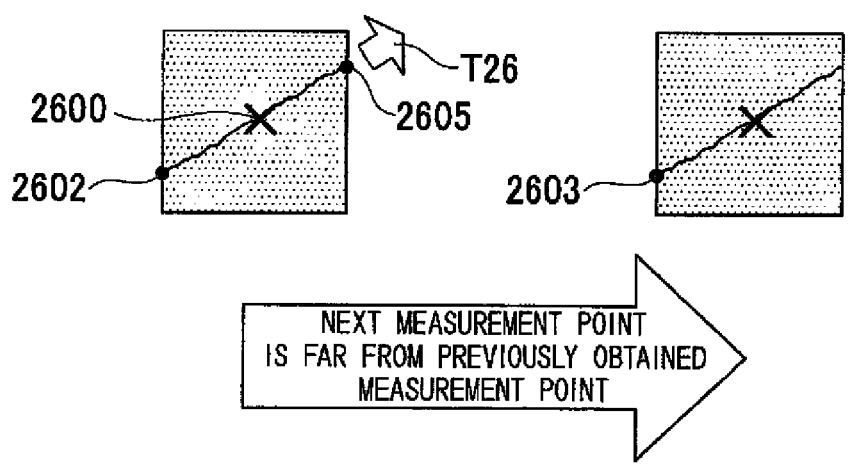
FIG. 26 shows for reference the procedure of the second-measurement-point-calculation in the first embodiment of the present invention.

A procedure of the second-measurement-point-calculation will be explained next with reference to FIG. 25. In addition, FIG. 26 schematically showing a procedure of the second-measurement-point-calculation will be referred to if necessary. The loss-composing point-calculating section 18d, upon carrying out the input of the image coordinate of the previously obtained measurement point by the control section 18a (step SB414a), executes a calculation of the characteristic point as shown in FIG. 15 and calculates two characteristic points (step SB414b). Accordingly, two characteristic points 2601 and 2602 corresponding to the measurement point 2600 are calculated.

Subsequently, the loss-composing point-calculating section 18d calculates two-dimensional distances between the characteristic point and the two previously obtained measurement points. The characteristic point that is farther from the previously obtained measurement is a next measurement point (step SB414c). The characteristic point 2602 of the characteristic points 2601 and 2602 is a next measurement point 2603 in a case where the direction indicating the previously obtained measurement point is a direction T22 of FIG. 26.

Subsequently, the loss-composing point-calculating section 18d determines as to whether or not the image coordinate of the loss-starting point is previously stored in the storage section 18g (step SB414d). The loss-composing point-calculating section 18d outputs the image coordinate of the calculated measurement point to the control section 18a in a case where the image coordinate of the loss-starting point has been previously stored in the storage section 18g. The control section 18a stores the image coordinate of the measurement point, i.e., the image coordinate of the loss-composing points in the storage section 18g (step SB414e). Subsequently, the procedure moves to a loss-ending-point-calculation described in FIG. 27. The procedure moves again to the loss-starting-point-calculation as shown in FIG. 23 in a case where the image coordinate of the loss-starting point has not been stored in the storage section 18g yet.

Figure 27:
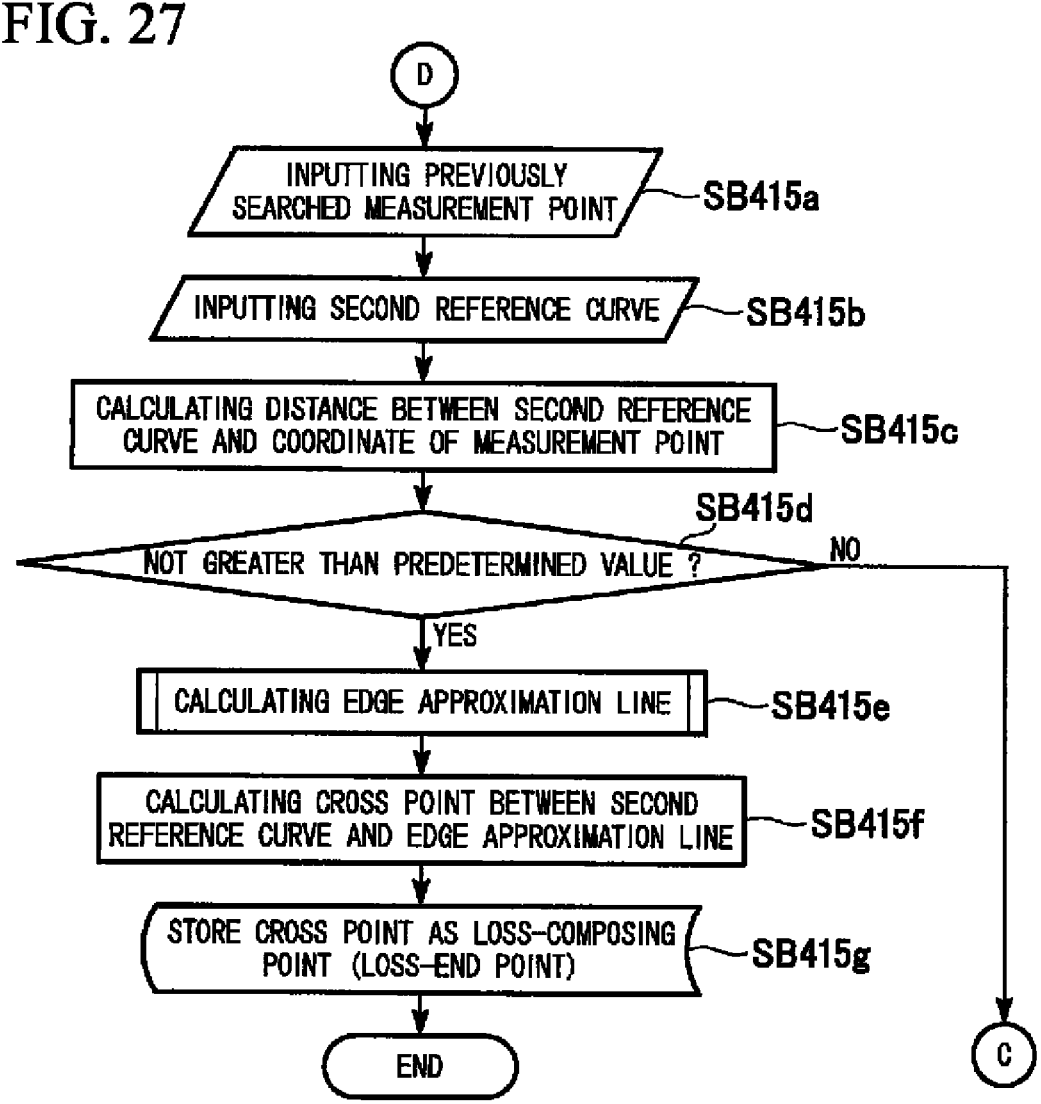
FIG. 27 is a flowchart showing a procedure of a loss-ending-point-calculation in the first embodiment of the present invention.
Figure 28:
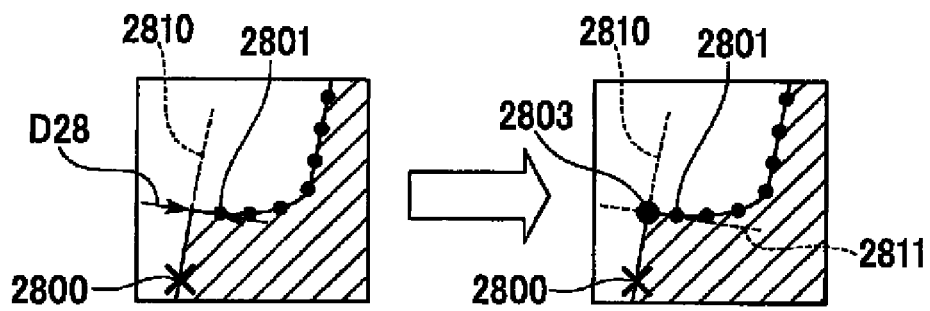
FIG. 28 shows for reference the procedure of the loss-ending-point-calculation in the first embodiment of the present invention.

The procedure of the loss-ending-point-calculation will be explained with reference to FIG. 27. Also, FIG. 28 schematically showing the procedure of the loss-ending-point-calculation will be referred to if necessary. To start with, the image coordinate of the previously obtained measurement point is input by the control section 18a (step SB415a). Details of the second reference curve calculated based on the second reference point are input by the control section 18a (step SB415b).

Subsequently, the loss-composing point-calculating section 18d upon calculating the two-dimensional distance between the second reference curve and the measurement point (step SB415c) determines as to whether or not the calculated two-dimensional distance is a predetermined value or smaller (step SB415d). In a case where the calculated two-dimensional distance is the predetermined value or smaller, the loss-composing point-calculating section 18d calculates an edge approximation line that is obtained by approximating the edge of the measurement object (step SB415e). An edge approximation line 2811 is calculated in a case of, e.g., FIG. 28 where a two-dimensional distance D28 between a second reference curve 2800 and the calculated second measurement point 2810 calculated based on the second reference point 2800 is the predetermined value or smaller.

Subsequently, the loss-composing point-calculating section 18d calculates the cross-point of the second reference curve and the edge approximation line (step SB415f). Accordingly, a cross-point 2803 of the second reference curve 2810 and the edge approximation line 2811 is calculated.

Subsequently, the loss-composing point-calculating section 18d outputs the image coordinate of the calculated cross-point to the control section 18a. The control section 18a stores the image coordinate of the cross-point, i.e., the image coordinate of the loss-composing points (loss-ending point) in the storage section 18g (step SB415g). This process finishes the whole procedure of calculating the aforementioned loss-composing points. Also, the procedure moves to the second-measurement-point-calculation again as shown in FIG. 25 in a case where the two-dimensional distance calculated in the step SB415c exceeds the predetermined value.

Figure 29:
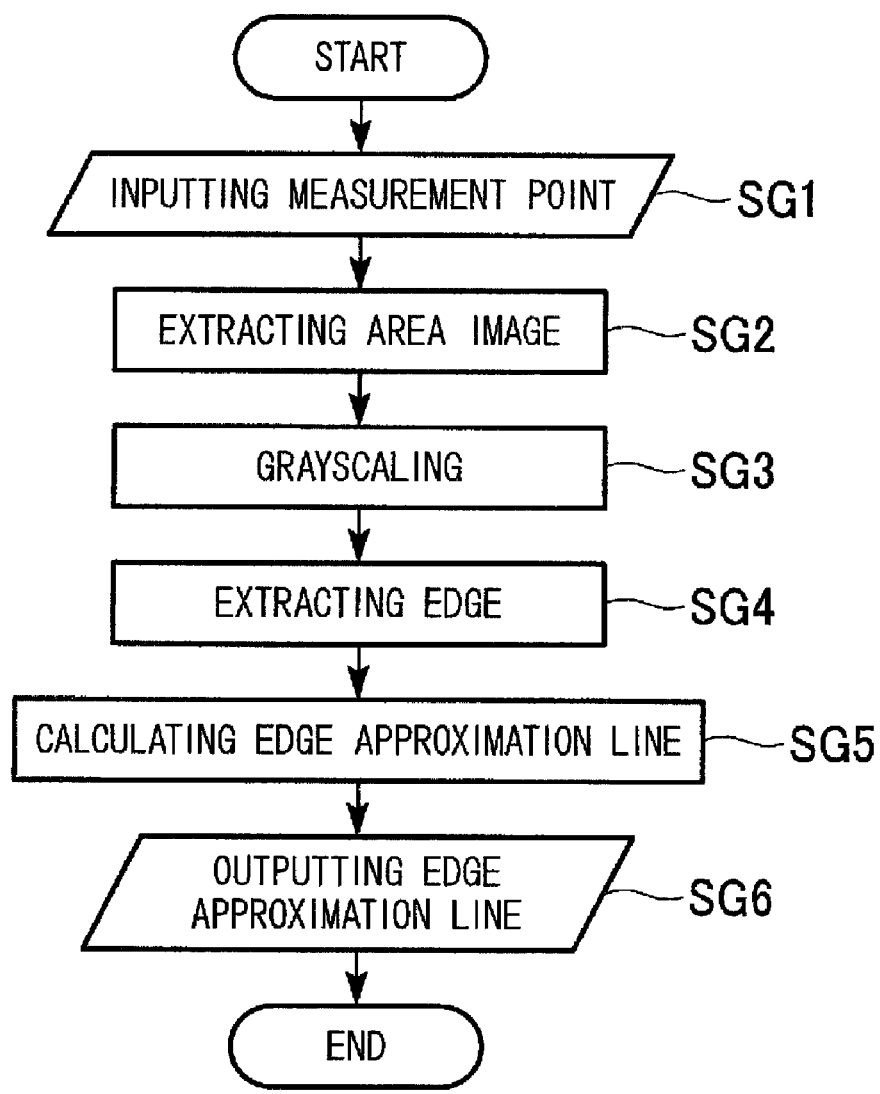
FIG. 29 is a flowchart showing an edge approximation line-calculation in the first embodiment of the present invention.

A procedure of calculating the edge approximation line in the step SB413e of FIG. 23 and in the step SB415e of FIG. 27 will be explained with reference to FIG. 29. The loss-composing point-calculating section 18d, upon carrying out an input of the image coordinate of a measurement point (step SG1), extracts an area image in a measurement point area based on the image coordinate of the input measurement point (step SG2).

Subsequently, the loss-composing point-calculating section 18d convert the extracted region image to grayscale (step SG3) and implements edge extraction to the grayscale image (step SG4). Subsequently, the loss-composing point-calculating section 18d calculates the approximation line of the extracted edge (step SG5) and outputs details of the calculated edge approximation line to the control section 18a (step SG6). The processes of the aforementioned steps SG1 to SG5 are the same as those of the steps SF1 to SF5 of FIG. 15.

A method for calculating a matching point in the step SB5 of FIG. 13 will be explained next. The loss-composing point-calculating section 18d executes a process of pattern-matching based on the loss-composing points calculated by the aforementioned loss calculation and calculates the matching point that corresponds to the left and right images. The pattern-matching method is the same as that is disclosed in Japanese Unexamined Patent Application, First Publication No. 2004-49638.

However, sometimes the pattern-matching process does not work and a matching point cannot be calculated in a case where the loss is of apex-type, since the loss apex positioned in the background of the measurement object does not have a characteristic pattern, e.g., the edge on the image. To address this difficulty, the present embodiment implements the calculation of the matching point of the loss apex as follows in a case where the loss is of apex-type.

Figure 30A:
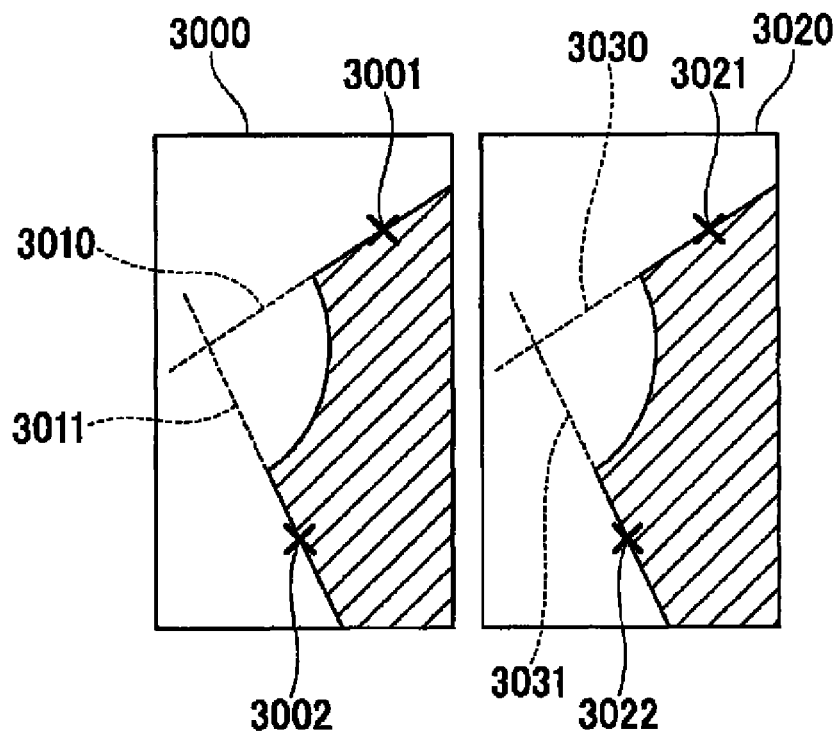
FIG. 30 shows for reference a method for calculating a matching point in the first embodiment of the present invention.

As shown in FIG. 30A, first calculated are matching points 3021 and 3022 in a right image 3020 that correspond to reference points 3001 and 3002 in a left image 3000. Subsequently, calculated are reference curves 3010 and 3011 passing through the reference points 3001 and 3002 respectively and reference curves 3030 and 3031 passing through the matching points 3021 and 3022 respectively.

Figure 30B:
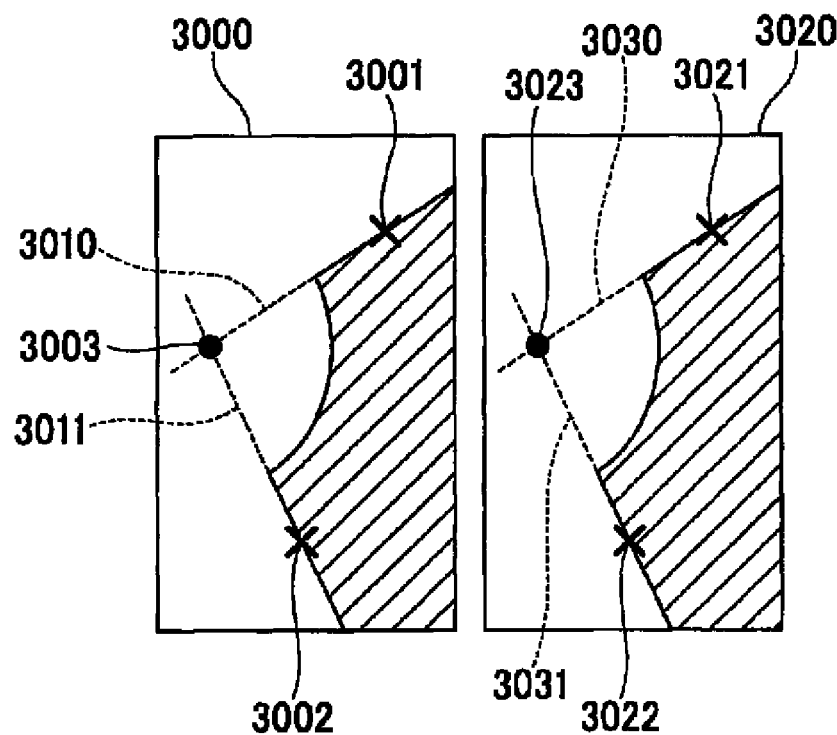

Subsequently calculated as a loss apex as shown in FIG. 30B is a cross-point 3003 of the reference curves 3010 and 3011 in the left image 3000. A cross-point 3023 of the reference curves 3030 and 3031 in the right image 3020 is calculated and assumed as the matching point of the loss apex.

Figure 31:
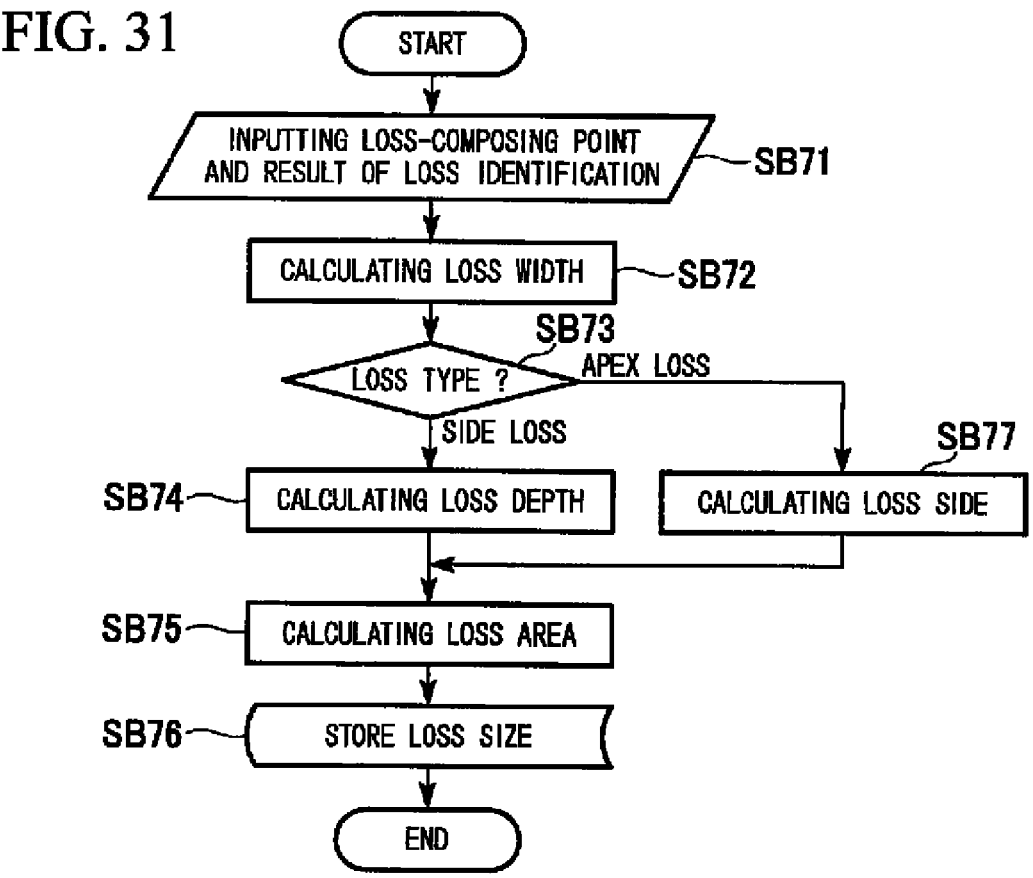
FIG. 31 is a flowchart showing a procedure of loss size-calculation in the first embodiment of the present invention.

A procedure of calculating loss size in the step SB7 of FIG. 13 will be explained next with reference to FIG. 31. The loss size-calculating section 18f, upon carrying out the input of spatial coordinates (three-dimensional coordinates) of the loss-composing points and a loss-identification result by the control section 18a (step SB71), calculates a loss width (the spatial distance between the loss-starting point and the loss-ending point) (step SB72).

Subsequently, the loss size-calculating section 18f identifies the loss type based on the loss identification result (step SB73). The loss size-calculating section 18f calculates a loss depth, i.e., a spatial distance between a predetermined loss-composing points and a line connecting the loss-starting point to the loss-ending point (step SB74) in a case where the loss is of side type. The loss size-calculating section 18f furthermore calculates a loss area, i.e., a spatial area of an area surrounded by all of the loss-composing points (step SB75).

Subsequently, the loss size-calculating section 18f outputs the calculated loss size to the control section 18a.

The control section 18a stores the loss size in the storage section 18g (step SB76). Alternatively, the loss size-calculating section 18f calculates a loss side, i.e., a spatial distance between the loss apex and the loss-starting point and a spatial distance between the loss apex and the loss-ending point (step SB77) in a case where the loss is of apex type. Subsequently, the procedure moves to step SB75.

Figure 32:
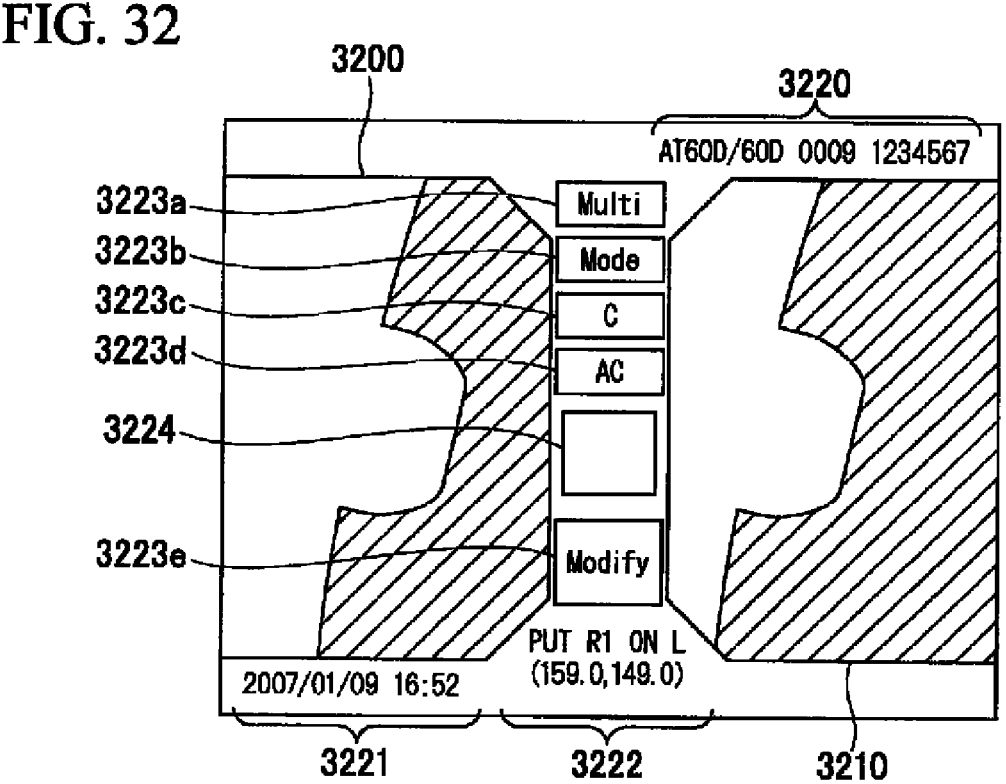
FIG. 32 shows for reference a measurement screen (prior to starting of loss measurement) in the first embodiment of the present invention.

A method of displaying a measurement result according to the present embodiment will be explained in next. FIG. 32 illustrates a measurement screen prior to starting of a loss measurement. Details of measurement are a left image of the measurement object displayed in a left image 3200 and a right image of the measurement object is displayed in a right image 3210. Other details, i.e., except the left image 3200 and the right image 3210, of measurement displayed in an upper section of the measurement screen are an optical adapter name information 3220; a date and time information 3221; icons 3223a, 3223b, 3223c, 3223d, and 3223e; and a zoom window 3224.

Both the optical adapter name information 3220 and the time information 3221 indicate measurement conditions.

The optical adapter name information 3220 literally indicates a name of an optical adapter for current use. The time information 3221 indicates current date and time literally. The message information 3222 includes literal information that indicates operational instructions to the user; and literal information that indicates the coordinate of a measurement condition, i.e., reference point.

Icons 3223a to 3223e constitute an operation menu that allows the user to input operational instructions, e.g., switching of measurement modes, or clearing measurement results. Signals are input into the measurement-processing section 18 that correspond to operations e.g., clicking a cursor, not shown in the drawings, moved on to any one of the icons 3223a to 3223e conducted by the user who maneuvers the remote controller 4 or the PC 31. The control section 18a recognizes the operational instructions input by the user based on the signals and controls the measurement processing. Also, an enlarged image of the measurement object is displayed on the zoom window 3224.

Figure 33:
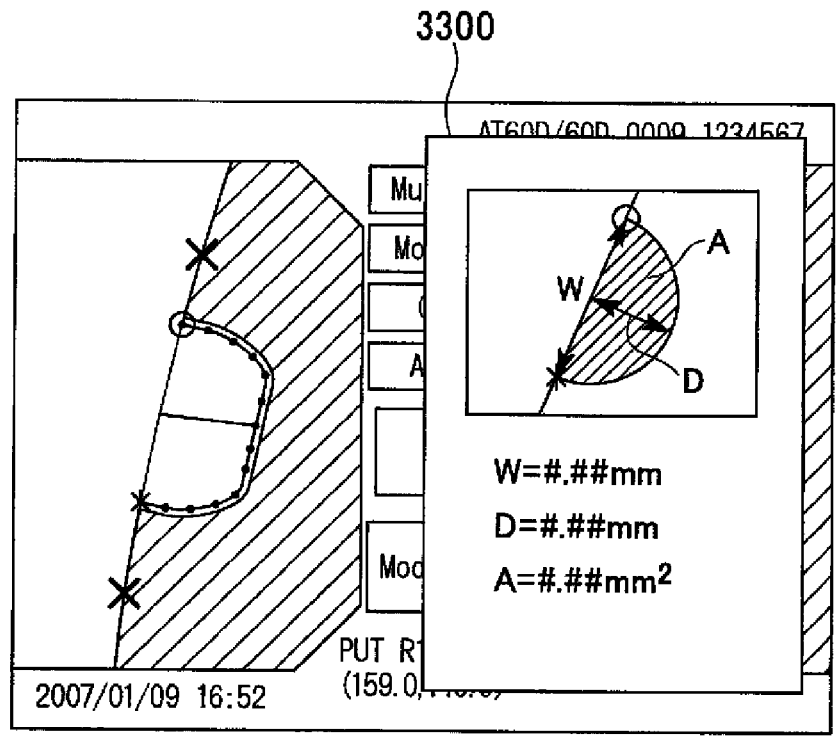
FIG. 33 shows for reference a measurement screen (while displaying the result of the loss measurement) in the first embodiment of the present invention.

FIG. 33 illustrates a measurement screen at a time of displaying the loss measurement result. Picked up image and literal information, etc. in the right image are hidden behind an result window 3300 since the result window 3300 that carries out displaying of measurement result overlaps on the picked up image and various information with respect to the measurement object as illustrated in FIG. 32. This state (first displaying state) is suitable for obtaining a space necessary to display measurement result and to improve visibility of the measurement result.

Figure 34:
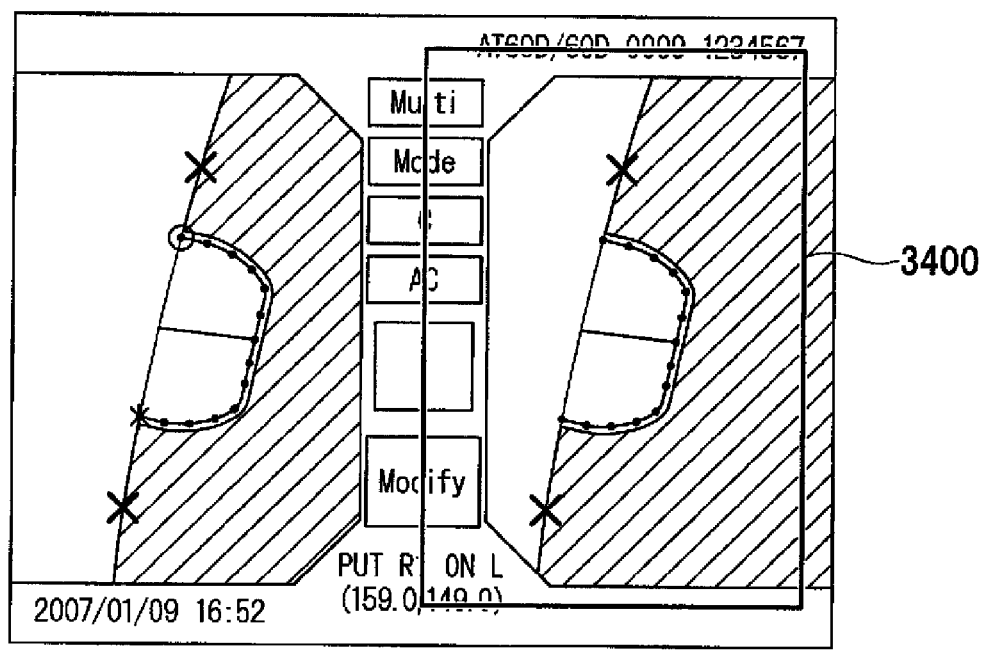
FIG. 34 shows for reference the measurement screen (while displaying the result of loss measurement) in the first embodiment of the present invention.

Operations e.g., clicking of a cursor, not shown in the drawings, and moving the cursor onto the result window 3300 conducted by the user who maneuvers the remote controller 4 or the PC 31 cause the control section 18a to control the measurement screen to change to a measurement screen as illustrated in FIG. 34. Transparent state of the result window 3400 and a hidden state of the measurement result visualize the picked up image and literal information in the right image that is hidden by the result window 3300 shown in FIG. 33. Only a frame of the result window 3400 is displayed.

This state (second displaying state) is suitable for obtaining a space necessary to display measurement result, e.g., a picked-up image and to improve visibility of the measurement result. This allows observing of matching state of the loss-composing points in, e.g, the left and the right images. Operations e.g., clicks conducted by the user who maneuvers the remote controller 4 or the PC 31 as illustrated in FIG. 34 cause the control section 18a to control the measurement screen to change to a measurement screen as shown in FIG. 33.

Figure 35:
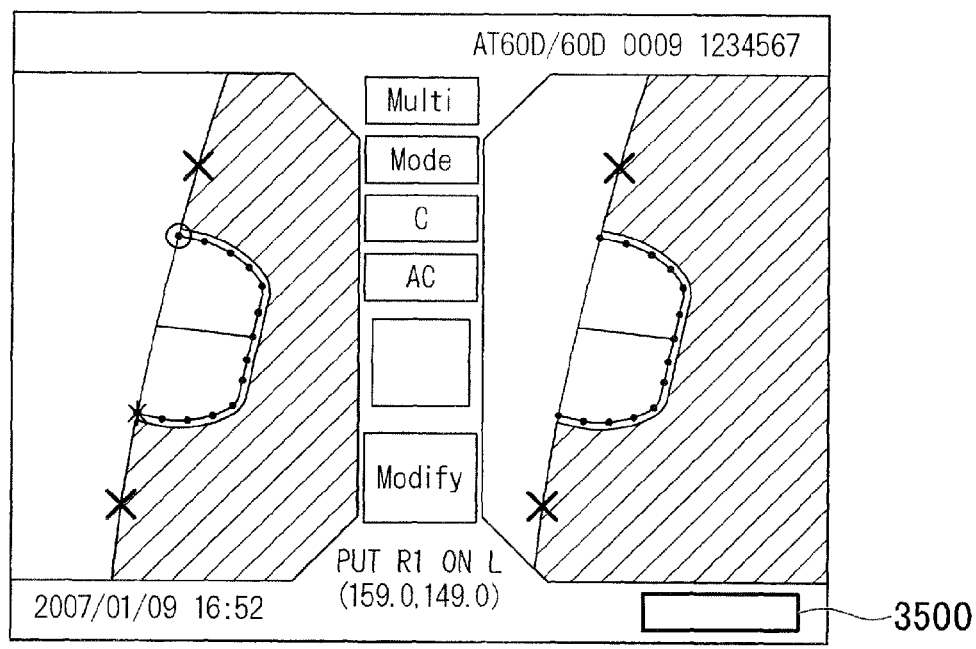
FIG. 35 shows for reference the measurement screen (while displaying the result of loss measurement) in the first embodiment of the present invention.

The measurement screen may be changed to the measurement screen as illustrated in FIG. 35 in a case where the user instructs to switch a displayed state of measurement screen as illustrated in FIG. 33. An result window 3500 as illustrated in FIG. 35 is obtained by minimizing an result window and moving a displayed position thereof so as not to prevent from displaying of other information. FIG. 35 shows a suitable state of a displayed image having a space necessary to display a measurement result, e.g., a picked-up image with improved visibility of the measurement result. Only one of the result window size and the display position may be changed, i.e., both of them may not have to be changed together unless for preventing from displaying of other information.

The present embodiment that enables measurement of loss size upon designating two reference points can reduce complex operations and improve operability more significantly than in a conventional case where three or more than four reference points are designated. Measurement accuracy in loss size can be improved by calculating a reference curve that is assumed to be a distortion-corrected curve that underwent distortion compensation of an image-pickup optical system provided to the distal end of an electronic endoscope.

Determining of loss type based on an angle defined by two reference curves that correspond to two reference points enables automatic measurement according to the determined loss type, thereby reducing complex operations and improving operability. Parameter calculation that indicates loss size based on automatic selection of parameters corresponding to loss type allows the user who is unaware of loss type to conduct optimal automatic measurement, thereby reducing complex operations and improving operability.

In addition, a conventional endoscope apparatus may be subject to lower measurement accuracy in loss size since an edge of an apex loss formed at an apex of a measurement object including an apex of an angle is approximated by a virtual curve and virtual points formed on the curve; and since selecting of the above virtual points that correspond to apices of the apex losses are conducted manually. In contrast, the present embodiment can improve measurement accuracy in loss size since a calculated cross-point of two reference curves that correspond to two reference points is assumed to be a loss-composing point (loss apex).

Also, measurement accuracy in loss size can be improved by calculating a reference curve that is assumed to be a distortion-corrected curve that underwent distortion compensation of an image-pickup optical system provided to the distal end of the electronic endoscope.

Loss size can be obtained in detail by calculating at least two types of parameters that indicate loss size.

In addition, calculating of at least two characteristic points on an edge of the measurement object and calculating a reference curve based on the calculated characteristic point can improve not only calculation accuracy in reference curve but also measurement accuracy in loss size.

In addition, the present embodiment can obtain the following effect. Conventional endoscopes had limits in size with respect to display apparatuses and monitors of the display apparatuses since movement of the apparatus must be facilitated in a site which undergoes measurement. Therefore, conventional endoscope apparatuses may be subject to lower visibility since a significant space cannot be obtained to display a picked-up image and measurement result of a measurement object.

In contrast, the present embodiment can obtain a necessary space in view of measurement information and measurement result by switching display states, between the first display state and the second display state, where the first display state displays a measurement result that overlaps on at least a part of measurement information including a picked-up image of a measurement object; the second display state visualizes the measurement information that is overlapped by the measurement result in the first display state. This can improve visibility of the measurement information and the measurement result. In addition to improved visibility, the screen of the display apparatus has a space to display not only a picked-up image of the measurement object but also literal information that indicates measurement conditions, literal information that indicates operational instructions for the user, and an operation menu for use in inputting details of operations.

FIRST MODIFIED EXAMPLE

Modified examples of the present embodiment will be explained next. To start with, a first modified example will be explained. A method for calculating a reference curve based on three characteristic points will be explained as follows in contrast to calculating of a reference curve based on two characteristic points as explained above.

Figure 36:
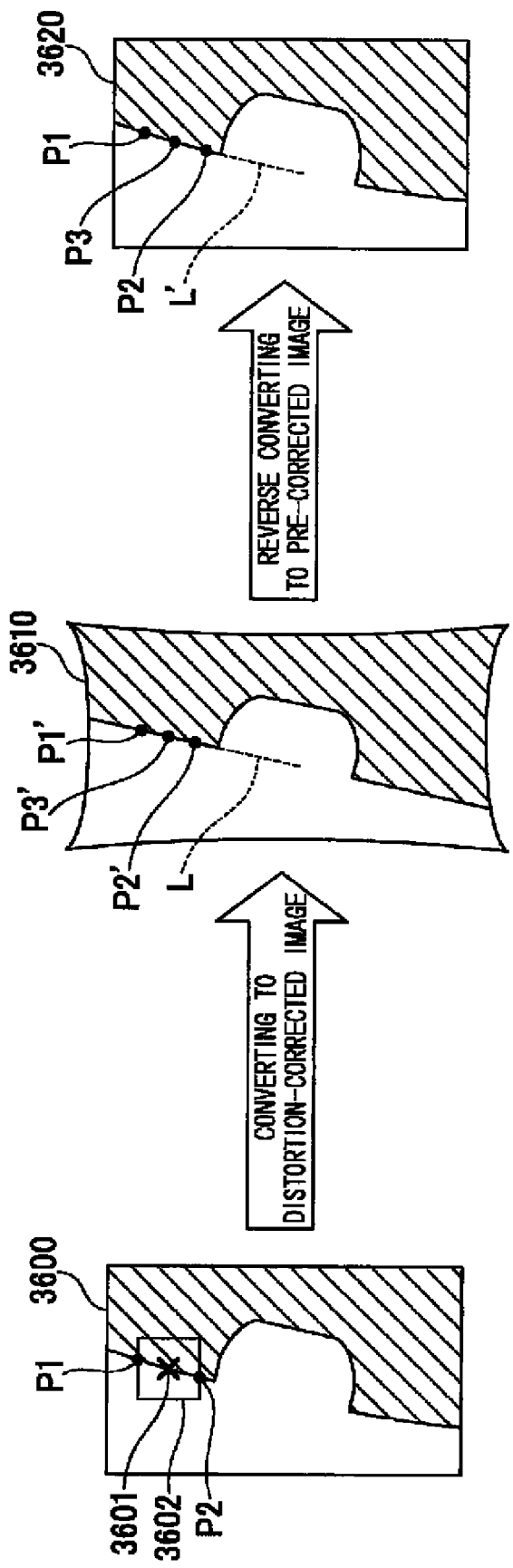
FIG. 36 shows for reference another method for calculating a distortion-corrected curve in the first embodiment of the present invention.

As illustrated in FIG. 36, two characteristic points P1 and P2 in an original image 3600 are calculated based on positions of a reference point 3601 and a reference point area 3602. Furthermore, a third characteristic point P3 is obtained by calculating the nearest point with respect to the reference point 3601 and the edge of the measurement object. It should be noted that the characteristic point P3 in the original image 3600 is omitted in the drawings.

Converting the original image 3600 by using the optical data obtains a distortion-corrected image 3610. Points P1'P2' and P3' are post-conversion points of P1, P2, and P3 respectively. Obtaining an approximation line L by calculating a line based on e.g., a least squares method based on the points P1', P2', and P3' and reverse conversion of pixel points on the approximation line L based on optical data causes the approximation line L to be converted into a curve L' on an original image 3620. The curve L' indicates a distortion-corrected curve that passes through the points P1, P2, and P3.

Calculating a reference curve based on three characteristic points as explained above can improve calculation accuracy in the reference curve. Calculation of a reference curve may be conducted by calculating four or more characteristic points in place of the above case using three characteristic points.

It should be noted that curve approximation using quadratic function may be conducted in contrast to linear approximation conducted with respect to a distortion-corrected characteristic point as explained above. Curve approximation may provide more accurate calculation of characteristic points if the distortion-corrected edge shape is curved rather than straightened.

SECOND MODIFIED EXAMPLE

Next, a second modified example will be explained. As previously explained with reference to FIG. 30, a matching point of two reference points is obtained on a right image when a spatial coordinate of a loss apex (three-dimensional coordinate) is calculated; the two reference curves on the right image are calculated based on the matching point; their cross-points are assumed to be matching points of loss apices; and then, a spatial coordinate of the loss apex is calculated based on the image coordinate of the matching point. Explained as follows is a method for calculating two three-dimensional lines based on characteristic points calculated based on two reference points, and obtaining a spatial coordinate of the loss apex by calculating the cross-point of the two three-dimensional lines.

Figure 37:
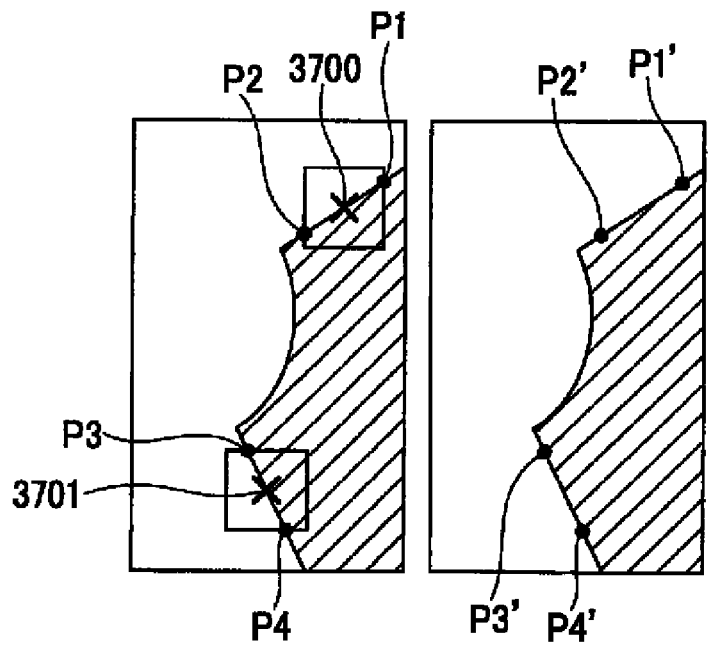
FIG. 37 shows for reference another method for calculating a loss apex in the first embodiment of the present invention.

Characteristic points are first calculated based on two reference points that are designated by the user with respect to an apex loss as illustrated in FIG. 37. The characteristic points P1 and P2 are calculated based on a reference point 3700; and the points P3 and P4 are calculated based on a reference point 3701. Subsequently, matching points P1 to P4' of the points P1 to P4 are obtained, and then, spatial coordinates of the characteristic points P1 to P4 and the characteristic points P1' to P4' are calculated. In the following, a formula (1) obtains a three-dimensional line L that passes through the characteristic points P1 and P2 where (Plx, Ply) and (Clx, Cly) indicate spatial coordinates of the characteristic points P1 and P2. Similarly, a formula (2) obtains a three-dimensional line R that passes through the characteristic points P3 and P4 where (Prx, Pry) and (Crx, Cry) indicate spatial coordinates of the characteristic points P3 and P4.

$$\frac{X - Clx}{Plx - Clx} = \frac{Y - Cly}{Ply - Cly} = \frac{Z - Clz}{Plz - Clz} \quad (1)$$

$$\frac{X - Crx}{Prx - Crx} = \frac{Y - Cry}{Pry - Cry} = \frac{Z - Crz}{Prz - Crz} \quad (2)$$

Figure 38:
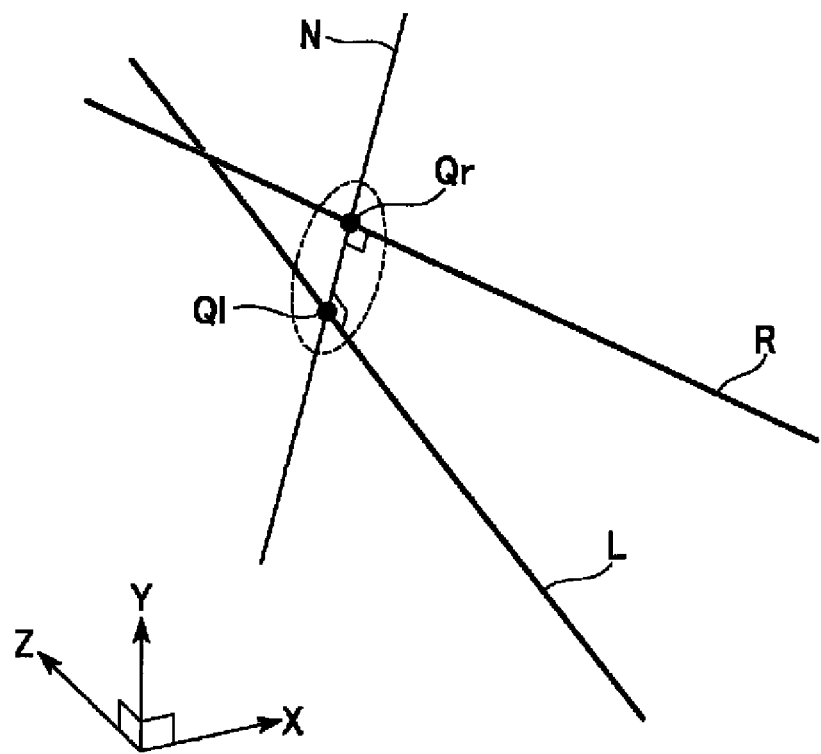
FIG. 38 shows for reference another method for calculating a loss apex in the first embodiment of the present invention.

Subsequently, the cross-point of the two three-dimensional lines L and R is calculated. The present modified example assumes that a most approaching position of the two lines is the cross-point of the two lines since the three-dimensional lines L and R seldom cross each other in fact. Searching of the most approaching point of the two lines is the same as searching of a position where normals of the two lines coincide. That is, a line N that connects a most approaching point Ql on the line L to a most approaching point Qr on the line R is orthogonal to the lines L and R as illustrated in FIG. 38. Therefore, an inner product obtained based on the directional vectors of the lines L and R and the directional vector of the line N is zero. The following formulae (3) and (4) indicate these vectors.

$$(Plx-Clx, Ply-Cly, Plz-Clz) \cdot (Qlx-Qrx, Qly-Qry, Qlz-Qrz) = 0 \quad (3)$$

$$(Prx-Crx, Pry-Cry, Prz-Crz) \cdot (Qlx-Qrx, Qly-Qry, Qlz-Qrz) = 0 \quad (4)$$

The following formulae (5) and (6) using the formula (1), the formula (2), and constants s and t, stand effective since the most approaching points Ql and Qr are on the lines L and R respectively.

$$\frac{Qlx - Clx}{Plx - Clx} = \frac{Qly - Cly}{Ply - Cly} = \frac{Qlz - Clz}{Plz - Clz} = s \quad (5)$$

$$\frac{Qrx - Crx}{Prx - Crx} = \frac{Qry - Cry}{Pry - Cry} = \frac{Qrz - Crz}{Prz - Crz} = t \quad (6)$$

Subsequently, the spatial coordinates of the most approaching points Ql and Qr are obtained by using the above formulae (1) to (6). To start with, the formulae (7) and (8) define constants tmp1, tmp2, tmp3, tmp4, tmp5, and tmp6 as follows.

$$tmp1 = Plx - Clx, \ tmp2 = Ply - Cly, \ tmp3 = Plz - Clz, \quad (7)$$

$$tmp4 = Prx - Crx, \ tmp5 = Pry - Cry, \ tmp6 = Prz - Crz, \quad (8)$$

Converting the formulae (3) and (4) by using the constants tmp1 to tmp6 obtains formula (3a) and formula (4a) as follows.

$$(tmp1, tmp2, tmp3) \cdot (Qlx-Qrx, Qly-Qry, Qlz-Qrz) \times 0 \quad (3a)$$

$$(tmp4, tmp5, tmp6) \cdot (Qlx-Qrx, Qly-Qry, Qlz-Qrz) = 0 \quad (4a)$$

Converting the formulae (5) and (6) by using the constants tmp1 to tmp6 obtains formula (5a) and formula (6a) as follows.

$$Qlx = tmp1*s + Clx, \ Qly = tmp2*s + Cly, \ Qlz = tmp3*s + Clz, \quad (5a)$$

$$Qrx = tmp4*t + Crx, \ Qry = tmp5*t + Cry, \ Qrz = tmp6*t + Crz, \quad (6a)$$

Subsequently, converting the formula (3a) and (4a) by using the formulae (5a) and (6a) obtains formula (3b) and (4b) as follows.

$$(tmp1, tmp2, tmp3) \cdot (tmp1*s - tmp4*t + Clx - Crx, tmp2*s - tmp5*t + Cly - Cry, tmp3*s - tmp6*t + Clz - Crz) = 0 \quad (3b)$$

$$(tmp4, tmp5, tmp6) \cdot (tmp1*s - tmp4*t + Clx - Crx, tmp2*s - tmp5*t + Cly - Cry, tmp3*s - tmp6*t + Clz - Crz) = 0 \quad (4b)$$

Furthermore, formulae (3c) and (4c) are obtained by rearranging the formulae (3b) and (4b) as follows.

$$(tmp1^2 + tmp2^2 + tmp3^2)*s - (tmp1*tmp4 + tmp2*tmp5 + tmp3*tmp6)*t + (Clx - Crx)*tmp1 + (Cly - Cry)*tmp2 + (Clz - Crz)*tmp3 = 0 \quad (3c)$$

$$(tmp1*tmp4 + tmp2*tmp5 + tmp3*tmp6)*s - (tmp4^2 + tmp5^2 + tmp6^2)*t + (Clx - Crx)*tmp4 + (Cly - Cry)*tmp5(Clz - Crz)*tmp6 = 0 \quad (4c)$$

The following formulae (9) to (14) define constants al, bl, cl, ar, br, and cr.

$$al = tmp1^2 + tmp2^2 + tmp3^2 \quad (9)$$

$$bl = tmp1*tmp4 + tmp2*tmp5 + tmp3*tmp6 \quad (10)$$

$$cl = (Clx - Crx)*tmp1 + (Cly - Cry)*tmp2 + (Clz - Crz)*tmp3 \quad (11)$$

$$ar = bl = tmp1*tmp4 + tmp2*tmp5 + tmp3*tmp6 \quad (12)$$

$$br = tmp4^2 + tmp5^2 + tmp6^2 \quad (13)$$

$$cr = (Clx - Crx)*tmp4 + (Cly - Cry)*tmp5 + (Clz - Crz)*tmp6 \quad (14)$$

Organizing the formulae (3c) and (4c) by using the formulae (9) to (14) obtans the following formulae (3d) and (4d).

$$al*s - bl*t + cl = 0 \quad (3d)$$

$$ar*s - br*t + cr = 0 \quad (4d)$$

The following formulae (15) and (16) stand effective based on the formulae (3d) and (4d).

$$\therefore s = \frac{-br*cl + bl*cr}{al*br - ar*bl} \quad (15)$$

$$\therefore t = \frac{-ar*cl + al*cr}{al*br - ar*bl} \quad (16)$$

On the other hand, coordinates of the most approaching points Ql and Qr are indicated by using the formulae (5) to (8) with the following formulae (17) and (18). Substituting the formulae (7) to (18) into the formulae (17) and (18) obtains the coordinates of the most approaching points Ql and Qr.

$$Qlx = tmp1*s + Clx, \ Qly = tmp2*s + Cly, \ Qlz = tmp1*s + Clz, \quad (17)$$

$$Qrx = tmp4*t + Crx, \ Qry = tmp5*t + Cry, \ Qrz = tmp6*t + Crz, \quad (18)$$

Finally, the following formula (19) indicates the spatial coordinate of the loss apex by assuming that the midpoint between the most approaching points Ql and Qr is the crosspoint between the lines L and R. Similarly to the above method, the spatial coordinate of the loss apex in the right image can be obtained based on the spatial coordinates of the characteristic points P1' to P4'.

$$\left( \frac{Qlx + Qrx}{2}, \frac{Qly + Qry}{2}, \frac{Qlz + Qrz}{2} \right) \quad (19)$$

THIRD MODIFIED EXAMPLE

A third modified example will be explained next. The previous explanations are based on assumption that the selected reference points free of a loss are positioned across a loss. However, sometimes the points on the edge free from a loss are difficult to be selected as reference points in a case where the loss is disposed near an end of the picked up image. A method for implementing loss measurement based on a loss end point as a reference point will be explained as follows.

Figure 39:
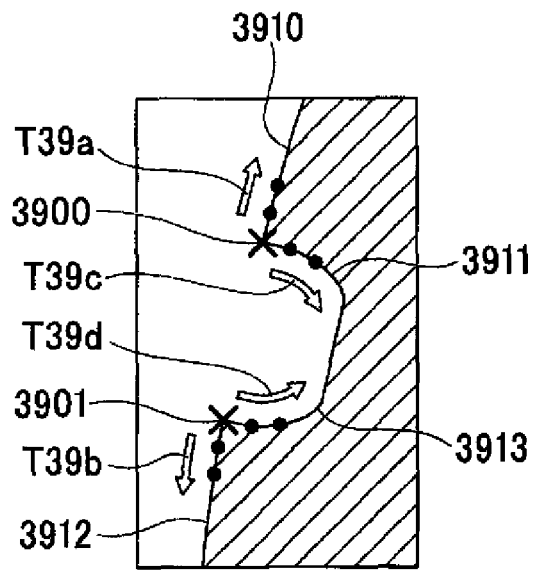
FIG. 39 shows for reference another method for designating reference points in the first embodiment of the present invention.

As illustrated in FIG. 39, reference points 3900 and 3901 designated by the user are two end points of the loss. The reference point 3900 is located at the cross-point of an edge 3910 of the measurement object in the vicinity of the loss and an edge 3911 of the loss. Also, the reference point 3901 is located at the cross-point of an edge 3912 of the measurement object in the vicinity of the loss and an edge 3913 of the loss.

The characteristic points for use in calculating the reference curves in the loss calculation are searched from the reference point 3900 in a direction T39a and from the reference point 3901 in a direction T39a. The characteristic points for use in calculating the loss-composing points are searched from the reference point 3900 in a direction T39c and from the reference point 3901 in a direction T39d. The directions T39a, T39b, T39c, and T39d can be distinguished based on correlation of the reference points 3900 and 3901 with characteristic points or measurement points.

Calculation of the characteristic points finishes when the necessary number of characteristic points are calculated. In addition, as far as calculation of the measurement points is concerned, the calculation of the measurement points finishes when the two-dimensional distance between a measurement point searched from the reference point 3900 and a measurement point searched from the reference point 3901 is a predetermined value or smaller after starting search of measurement points from the reference point 3900 and the reference point 3901.

As previously explained, loss measurement can be conducted regardless of the position of a loss in a picked up image as long as the full image of the loss is picked up since the end point of the loss can be designated as a reference point. In addition, complex operations can be reduced and operability can be improved since it is not necessary to change an image-pickup position to pick up another image to designate a reference point.

Details of other processes in the present embodiment will be explained next. Sometimes, bright portions due to reflections existing in the background of an image may become noise that will be recognized as a part of the object erroneously; thus, measurement accuracy may be deteriorated since the previously explained calculation of a reference curve (step SB2 of FIG. 12) and the previously explained calculation of loss-composing points (step SB4 of FIG. 12) include a process of conducting grayscale conversion to an image.

Figure 40A:
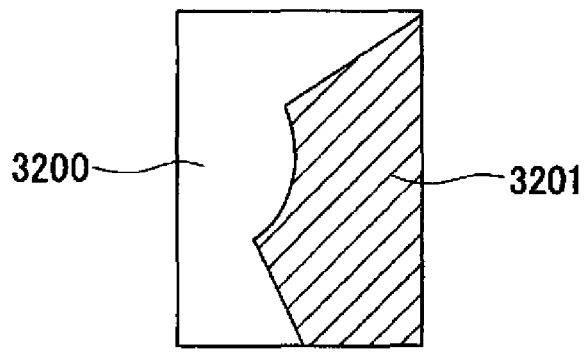
FIGS. 40A to 40B explain measurement accuracy in the first embodiment of the present invention for reference.
Figure 40B:
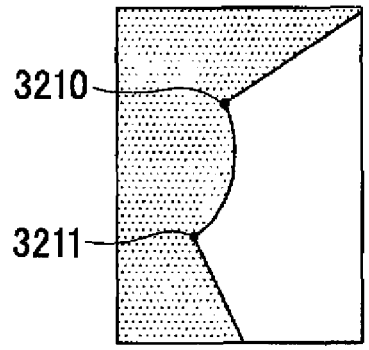

A binary image as shown in FIG. 40B is not subject to generation of noise in a case where contrast between the background 3200 and the object 3201 is clear in a picked up image as shown in FIG. 40A. This case of highly accurate perception of the original loss-starting point 3210 and the loss-ending point 3211 provides high measurement accuracy.

Figure 41A:
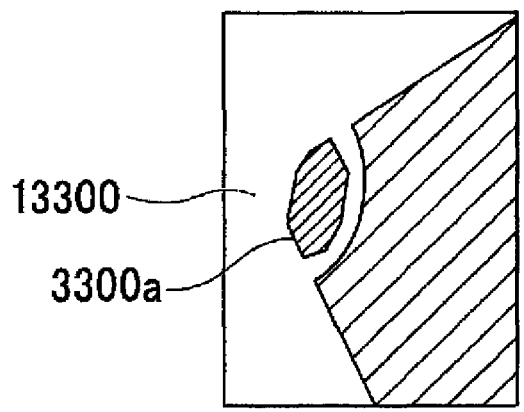
FIGS. 41A to 41C explain the measurement accuracy in the first embodiment of the present invention for reference.
Figure 41B:
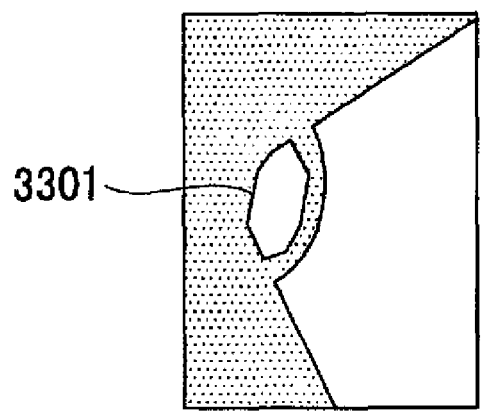
Figure 41C:
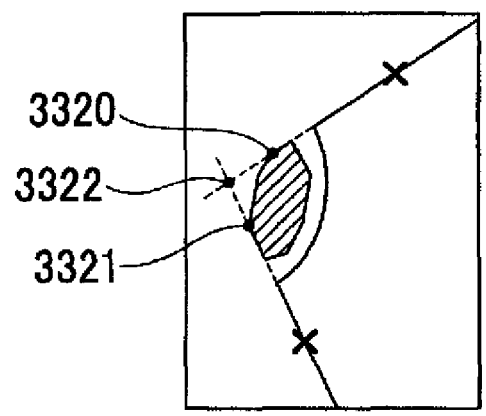

The area 3301 will have noise that appears to correspond to the high brightness area 3300*a* in the binary image as shown in FIG. 41B in a case where a high brightness area 3300*a* due to reflection exists in the background 13300 of the picked up image as shown in FIG. 41A. Executing loss measurement by using the binary image causes a point 3320 to become a loss-starting point, a point 3321 to become a loss-ending point, and a point 3322 to become a loss apex respectively as illustrated in FIG. 41C, thereby providing erroneous acknowledgement of a loss section and declining measurement accuracy.

Figure 42A:
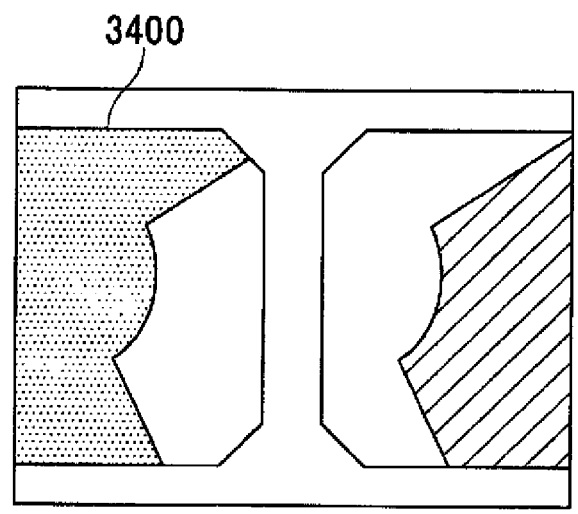
FIGS. 42A and 42B show for reference the measurement screen (while displaying a binarized image) in the first embodiment of the present invention.
Figure 42B:
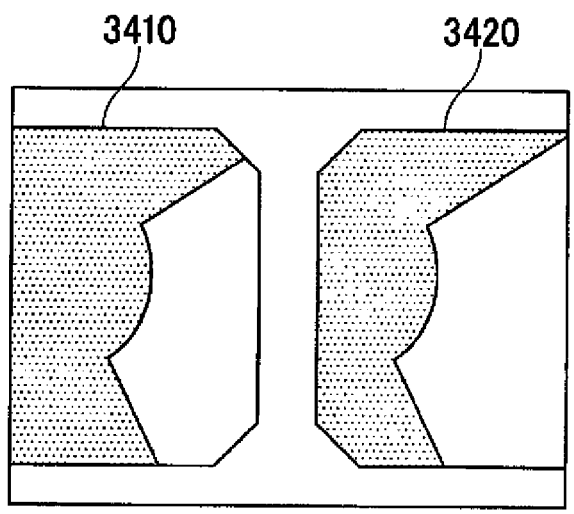
Figure 43:
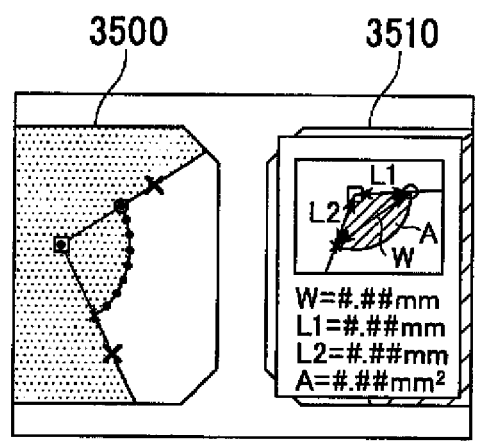
FIG. 43 shows for reference the measurement screen (while displaying the binary image) in the first embodiment of the present invention.

To address this, the present embodiment enabling displaying of a binary image on the LCD monitor 5 or the face-mount display 6 allows the user to perceive existence of noise that tends to be subject to recognition error as a part of the object. FIGS. 42A, 42B, and 43 illustrate examples of a binary image.

FIGS. 42A and 42B illustrate examples of display prior to designating reference points, i.e., measurement screens displayed prior to the measurement image 1230 as shown in FIG. 12. A binary image displayed prior to designation of a reference point allows the user to estimate measurement accuracy prior to starting of loss measurement. FIG. 42A shows a binary image of the left image 3400, and FIG. 42B shows binary images of a left-hand image 3410 and a right image 3420.

FIG. 43 shows an example of an image displayed at a time of measurement result, i.e., a measurement screen displayed subsequent to the measurement image 1250 as shown in FIG. 12. Both the left image 3500 and the right image 3510 may be converted into binary images in place of FIG. 43 showing the left image 3500 alone converted into a binary image. A binary image displayed at a time of outputting a measurement result can provide post-loss-measurement acknowledgement to the user regarding whether or not a measurement free from noise-based misapprehension has been implemented successfully.

Figure 44:
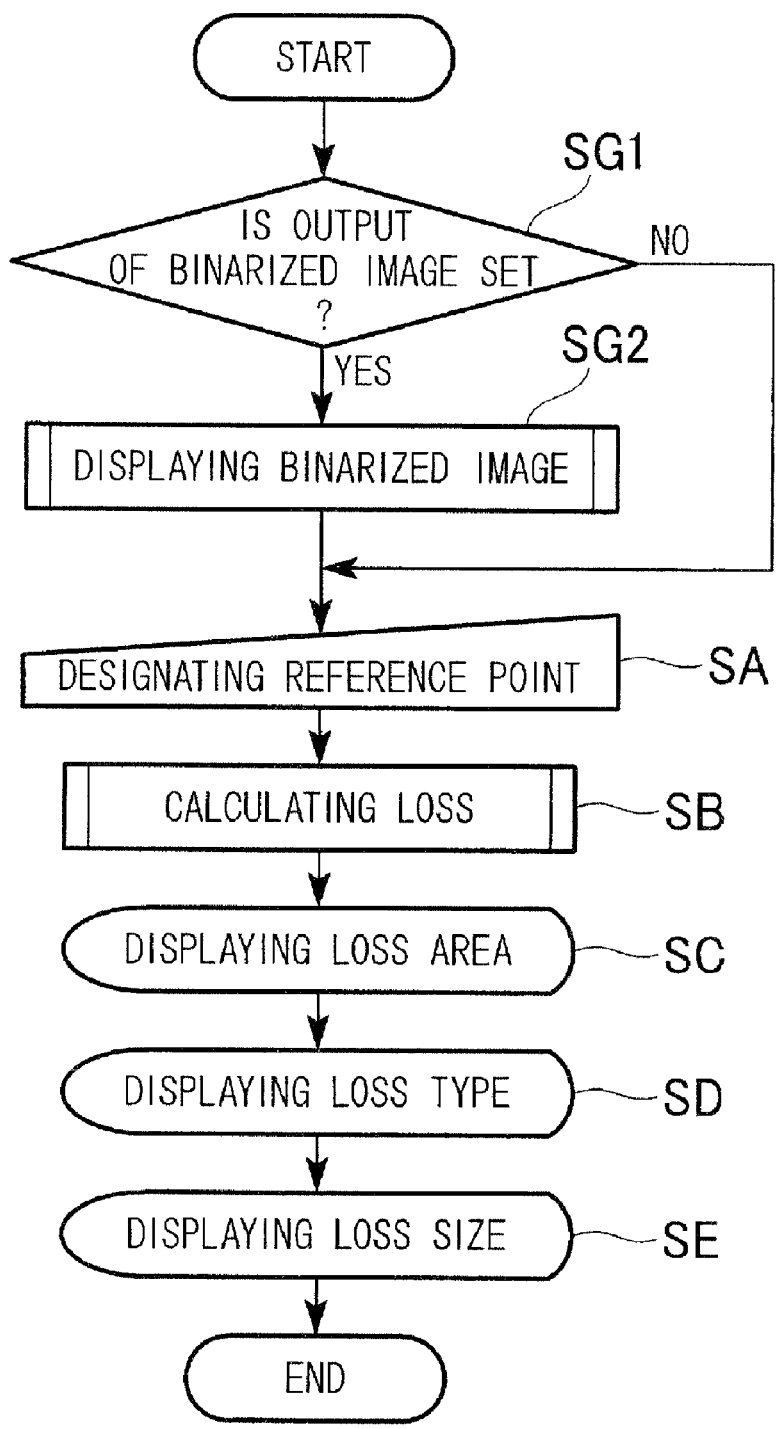
FIG. 44 is a flowchart showing the procedure of the loss measurement in the first embodiment of the present invention.

A procedure of displaying a binary image will be explained next. Explanation will be omitted pertaining to details of procedures shown in FIGS. 44 to 47 in duplicate with those of FIG. 11 since they have been previously explained. FIG. 44 shows a procedure of displaying a binary image prior to designation of reference points. To start with, the control section 18*a* monitoring operations undertaken by the remote controller 4 or the personal computer 31 determines as to whether or not an image used for verifying measurement accuracy, i.e., an output of a binary image, is established (step SG1).

The procedure progresses to the step SA in the absence of an output established for a binary image. Alternatively, a binary image is displayed (step SG2) based on an output established for a binary image. Subsequently, the procedure upon progressing to the step SA, executes the previously explained steps SA to SE in this order.

Figure 48:
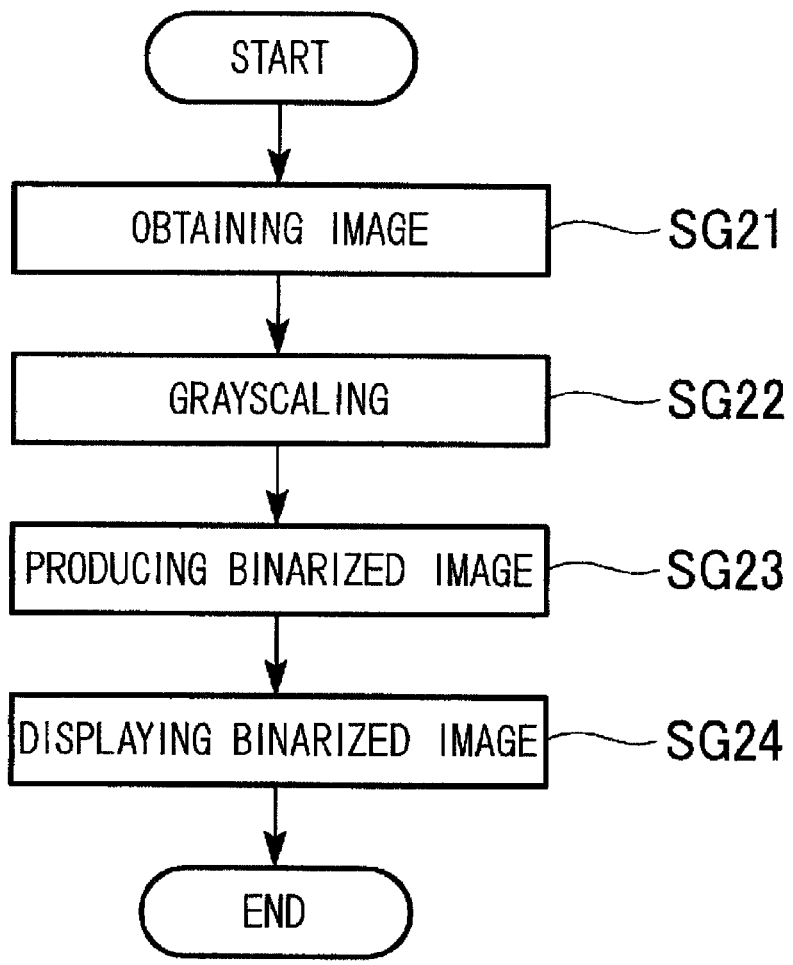
FIG. 48 is a flowchart showing a procedure of displaying a binary image in the first embodiment of the present invention.

FIG. 48 shows a procedure of the step SG2. To start with, the control section 18*a* obtains an image data constituting an image signal from the image-signal-processing circuit 12, and then outputs to the contrast reduction section 18*h* (step SG21). The contrast reduction section 18*h* produces a binary image (step SG23) by extracting a brightness data (signal level) from the image data, providing grayscale conversion to the image (step SG22), and binarizing the brightness data based on a threshold using a predetermined brightness. The threshold, e.g., 128 used in the step SG23, converts the brightness into a value of 0 (zero) or 255 in a case where brightness in each pixel is indicated by one of 0 (zero) to 255.

Subsequently, the control section 18*a* obtains the binary image from the contrast reduction section 18*h* and outputs to the image-signal-processing circuit 12. The LCD monitor 5 or the face-mount display 6 displays the binary image (step SG24) subsequent to a process, executed by the image-signal-processing circuit 12, of synthesizing the binary image and an operation menu. The binary image displayed accordingly may be based on the left image alone as shown in FIG. 42A, or on both the left-hand and the right images as shown in FIG. 42B.

Figure 45:
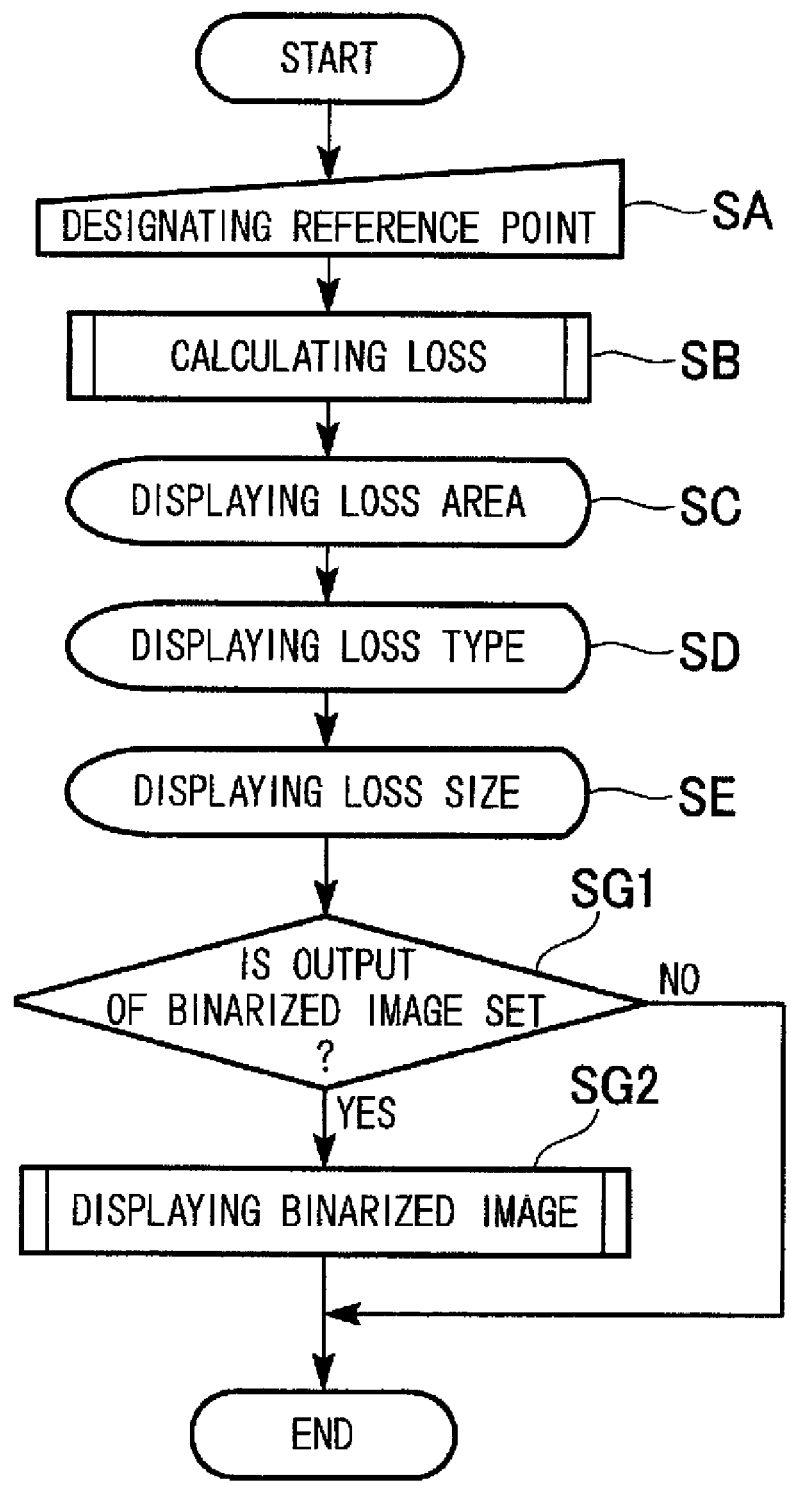
FIG. 45 is a flowchart showing the procedure of the loss measurement in the first embodiment of the present invention.

FIG. 45 shows a procedure of displaying a binary image at a time of outputting a measurement result. To start with, the steps SA to SE are executed in this order. Subsequently, the steps SG1 and SG 2 as shown in FIG. 44 are executed in this order, and a binary image is displayed based on an output established regarding the binary image.

Figure 46:
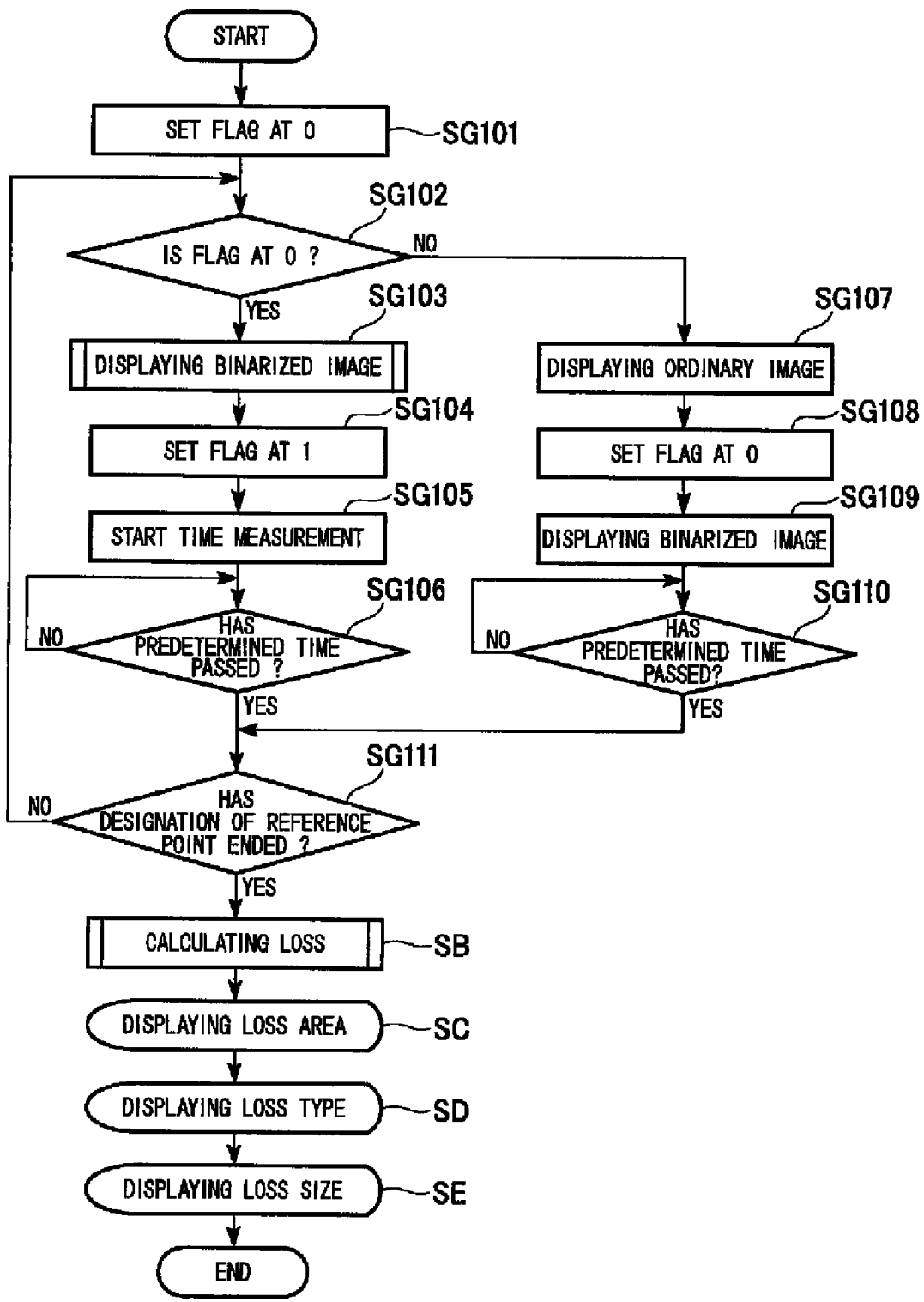
FIG. 46 is a flowchart showing the procedure of the loss measurement in the first embodiment of the present invention.

FIG. 46 shows a procedure of displaying the binary image and an ordinary image alternately prior to designation of reference points. To start with, the control section 18*a* establishes 0 (zero) corresponding to a flag for use in determining a display format of an image (step SG101). Subsequently, the control section 18*a* evaluates the value of a flag (step SG102). Processes afterward depend on the result of the evaluation. Also, in concurrence with the evaluation, the control section 18*a* obtains an image data that constitutes the image signal from the image-signal-processing circuit 12.

In case of the flag value 0 (zero), the image data supplied by the control section 18*a* causes the contrast reduction section 18*h* to execute a contrast-reduction, and simultaneously execute a process for displaying a binary image (step SG103). The process executed in the step SG103 is the same as the process shown in FIG. 48.

The control section 18*a*, upon finishing the process of step SG103, establishes a flag 1 (one), and furthermore instructs the time-measuring section 18*i* to start time measurement (step SG105). The control section 18*a* monitors the measured time and determines as to whether or not a predetermined time has passed (step SG106). The process goes back to the step SG106 to continue monitoring of time measurement in a case where the predetermined time has not passed. The procedure progresses to step SG111 in a case where the predetermined time has passed. This case of the time-measuring section 18*i* finishes the time measurement based on the instruction of the control section 18*a*.

On the other hand., the flag value of 1 (one) in the step SG102 causes the control section 18*a* to execute a process for displaying an ordinary image (step SG107). This state of LCD monitor 5 or face-mount display 6 displays an ordinary image in place of a binary image. The control section 18*a*, upon finishing the process of step SG108, establishes a flag 0 (zero), and furthermore instructs the time-measuring section 18*i* to start time measurement (step SG109). The control section 18*a* monitors the measured time and determines as to whether or not a predetermined time has passed (step SG110). The process goes back to the step SG110 to continue monitoring of time measurement in a case where the predetermined time has not passed. The procedure progresses to step SG111 in a case where the predetermined time has passed. This case of the time-measuring section 18*i* finishes the time measurement based on the instruction of the control section 18*a*.

A process, not shown in the drawings, associated with designation of reference points is executed in concurrence with the processes of the aforementioned steps SG101 to SG110. The control section 18*a* determines in the step SG111 as to whether or not the designation of reference points has been finished (step SG111). The procedure goes back to the step SG102 if the designation of reference points has not been finished. The aforementioned steps SB to SE are executed in this order if the designation of reference points has been finished.

Figure 47:
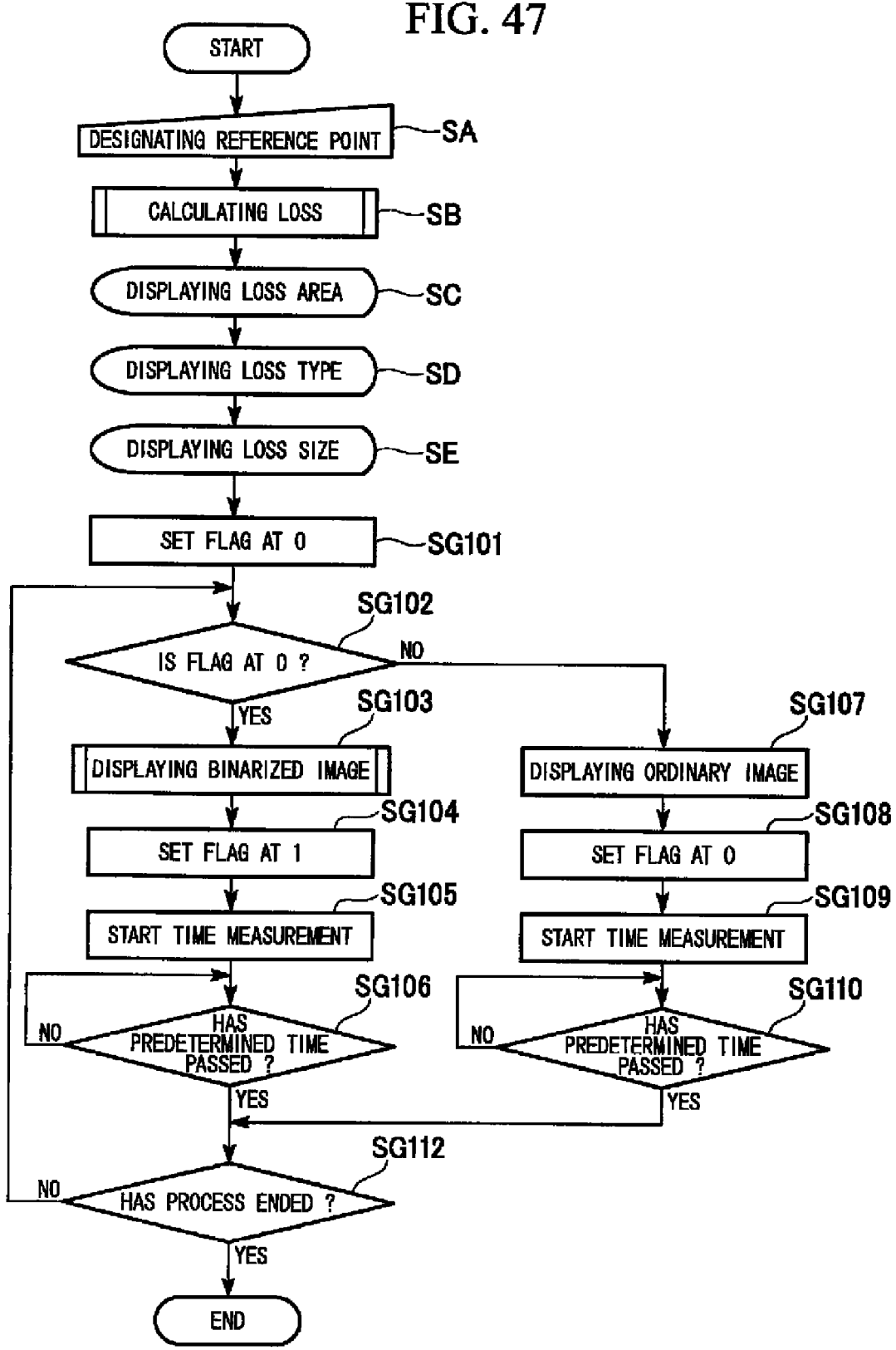
FIG. 47 is a flowchart showing the procedure of the loss measurement in the first embodiment of the present invention.

FIG. 47 shows a procedure of displaying the binary image and the ordinary image alternately at a time of outputting the measurement result. To start with, the steps SA to SE are executed in this order. Subsequently, a process associated with displaying the binary image or the ordinary image is executed (steps SG101 to SG110). Details will be omitted pertaining to the processes conducted in the steps SG101 to SG110 since they are previously explained. In step SG112, the control section 18*a* monitors operations conducted by the remote controller 4 or the personal computer 31 and determines as to whether or not the remote controller 4 or the personal computer 31 has received an instruction of finishing the process (step SG112). The procedure goes back to the step SG102 if an instruction of finishing the process has not been received. The process finishes upon receiving an instruction to finish the process.

The procedures shown in FIGS. 47 and 48 switch between two states at a predetermined time interval automatically, i.e., displaying of the binary image and displaying of the ordinary image. In another configuration, the control section 18*a* may display the binary image and the ordinary image alternately at an any timing interval by monitoring the operations conducted by the remote controller 4 or the personal computer 31 and switching the displaying state based on the monitored operations.

The present embodiment that enables measurement of loss size upon designating two reference points can reduce complex operations and improve operability more significantly than in a conventional case where three reference points, or four or more reference points are designated. Also, displaying the contrast-reduced binary image allows the user to perceive existence of noise that may be erroneously recognized as a part of the object, and to acknowledge whether or not a measurement is conducted as intended.

The measurement result, displayed in the result windows 1223 and 1253 of the measurement images 1220 and 1250 as shown in FIG. 12, enabling measurement accuracy perception does not always provide intuitive perception of measurement accuracy to the user since displayed data is unnecessary for the measurement accuracy perception sometimes, or space is limited for displaying information necessary for the measurement accuracy perception. In contrast, displaying the contrast-reduced image provides the user intuitive perception of measurement accuracy.

The image displayed for use in perceiving the measurement accuracy may be not only a binary image but also a quaternary image, or an octal image. From a viewpoint of real-time display, a binary image is preferable since it can be produced with lesser workload.

Capability of switching a displaying state between a binary image and an ordinary image allows the user to make a comparison between a measurement image and an object image and to observe details of the measurement accuracy, thereby providing more efficient measurement operation. In addition, switching between the aforementioned two kinds of displaying states at a user's designating timing that has been input to the remote controller 4 or the personal computer 31 provides capability of recognizing measurement accuracy at an any timing. Additionally changing a once-changed displaying state subsequent to a predetermined duration can reduce operational workload of the user.

[Second Embodiment]

Next, a second embodiment of the present invention will be explained. The endoscope apparatus according to the first embodiment has the following possibilities. Reference points, associated with a loss of side type illustrated in FIG. 49A, designated by the user are not points on the edge of a loss or the cross-points of edges, but points 4000, and 4010, etc. innermore relative to the edge (innermore of the measurement object) allows loss-composing points (including the reference points 4000 and 4010 and measurement points) as illustrated in FIG. 49B to be recognized.

This case of loss outline 4020 (including a line segment joining the reference point 4000 to the reference point 4010) is formed by twisted line segments obtained by joining the loss-composing points in an extracted order from the reference point 4000 to the reference point 4010. The twisted shape in this case indicates that the line segments constituting the loss outline are partly crossing. The loss outline 4020 has a twisted shape since the line segments constituting the loss outline 4020 are crossing in areas 4030 and 4040. The measurement screen of an result window 4050 displays a measurement result error as illustrated in FIG. 49B based on a twisted shape of the loss outline.

The following is the reason the area of loss that has a twisted-shaped loss outline cannot be calculated. The endoscope apparatus according to the first embodiment and the present embodiment calculates a loss area by the following method. The loss area illustrated in FIG. 50A is obtained by surrounding a loss area by loss-composing points; dividing the loss area into a plurality of triangles each having an apex, i.e., the loss-composing point, and obtaining a sum of three-dimensional areas. Not a single closed area but a plurality of closed regions constitute the area surrounded by the twisted-shaped loss outline as illustrated in FIG. 41B. This case of loss area cannot be calculated since the absence of a loss-composing point at a position 4100 where the loss outlines crosses with each other provides no definition with respect to a triangle.

Apex loss is likely to encounter the same possibility. Reference points illustrated in FIG. 51 designated by the user are not points on the edge of a loss or the cross-points of edges, but the points 4200, and 4210, etc. innermore relative to the edge (innermore of the measurement object) cause loss-composing points (including the reference points 4200 and 4210 and measurement points) to be recognized.

This case of loss outline 4230 (including a line segment joining the reference point 4200 to the reference point 4220 and a line segment joining the reference point 4210 to the loss apex 4220) is formed by twisted line segments obtained by joining the loss-composing points in an extracted order from the reference point 4200 to the reference point 4210. This is because the line segments constituting the loss outline 4230 cross in areas 4240 and 4250. The measurement screen of an result window 4260 displays a measurement result error as illustrated in FIG. 51C based on a twisted shape of the loss outline.

Figures 52A, 52B, 52C:
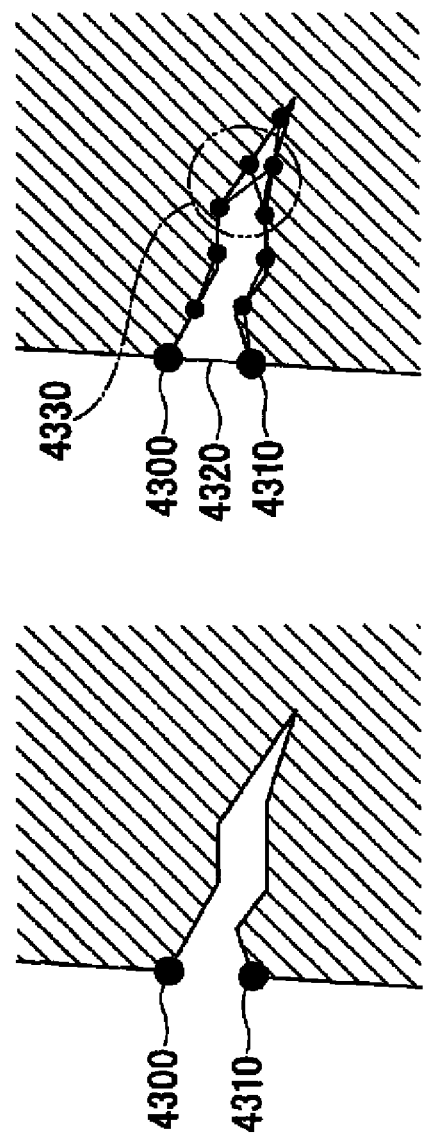
FIGS. 52A to 52C explain the problem in the second embodiment of the present invention for reference.

Sometimes, a complex and narrow shape of flow area as illustrated in FIG. 52A cannot be calculated even though the positions of the reference points designated by the user are not problematic. The loss-composing points (including reference points 4300 and 4310) as illustrated in FIG. 52 are acknowledged based on the reference points 4300 and 4310 designated by the user as illustrated in FIG. 52A.

This case of loss outline 4320 (including a line segment joining the reference point 4300 to the reference point 4310) is formed by twisted line segments obtained by joining the loss-composing points in an extracted order from the reference point 4300 to the reference point 4310. This is because the line segments constituting the loss outline 4320 cross in an area 4330. The measurement screen of an result window 4340 displays a measurement result error as illustrated in FIG. 52C based on a twisted shape of the loss outline.

Twisted shape of the loss outline 4320 is obtained since a plurality of edges detected in a measurement point area around a measurement point that previously underwent a searching of measurement point that would become a loss-composing point provide recognition that the edges are located in positions different from original edge positions. The reason will be explained as follows as to why a twisted shape of the loss outline is as illustrated FIG. 52A is obtained.

Figure 53D:
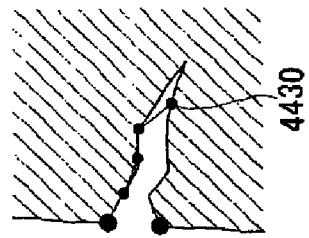
FIGS. 53A to 53I explain the problem in the second embodiment of the present invention for reference.
Figure 53C:
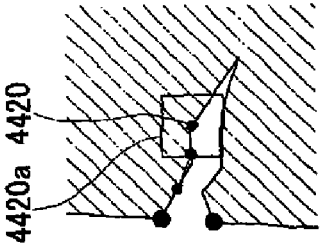
Figure 53B:
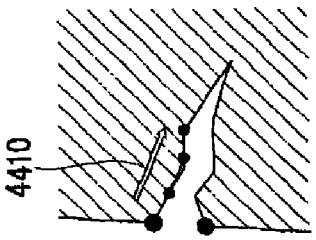
Figure 53H:
Figure 53G:
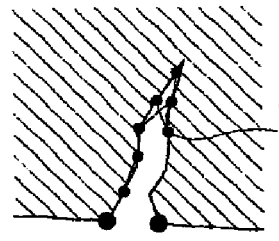
Figure 53F:
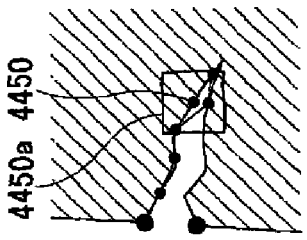
Figure 53A:
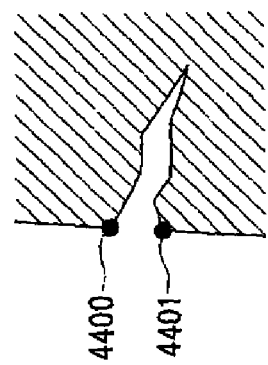

Reference points 4400 and 4401 designated by the user as illustrated in FIG. 53A cause measurement points to be searched along a direction of an arrow 4410 as illustrated in FIG. 53B. In a case as illustrated in FIG. 53C, searching a measurement point next to a measurement point 4420 provides an image to be extracted within a measurement point area 4420a around the measurement point 4420.

Figure 54:
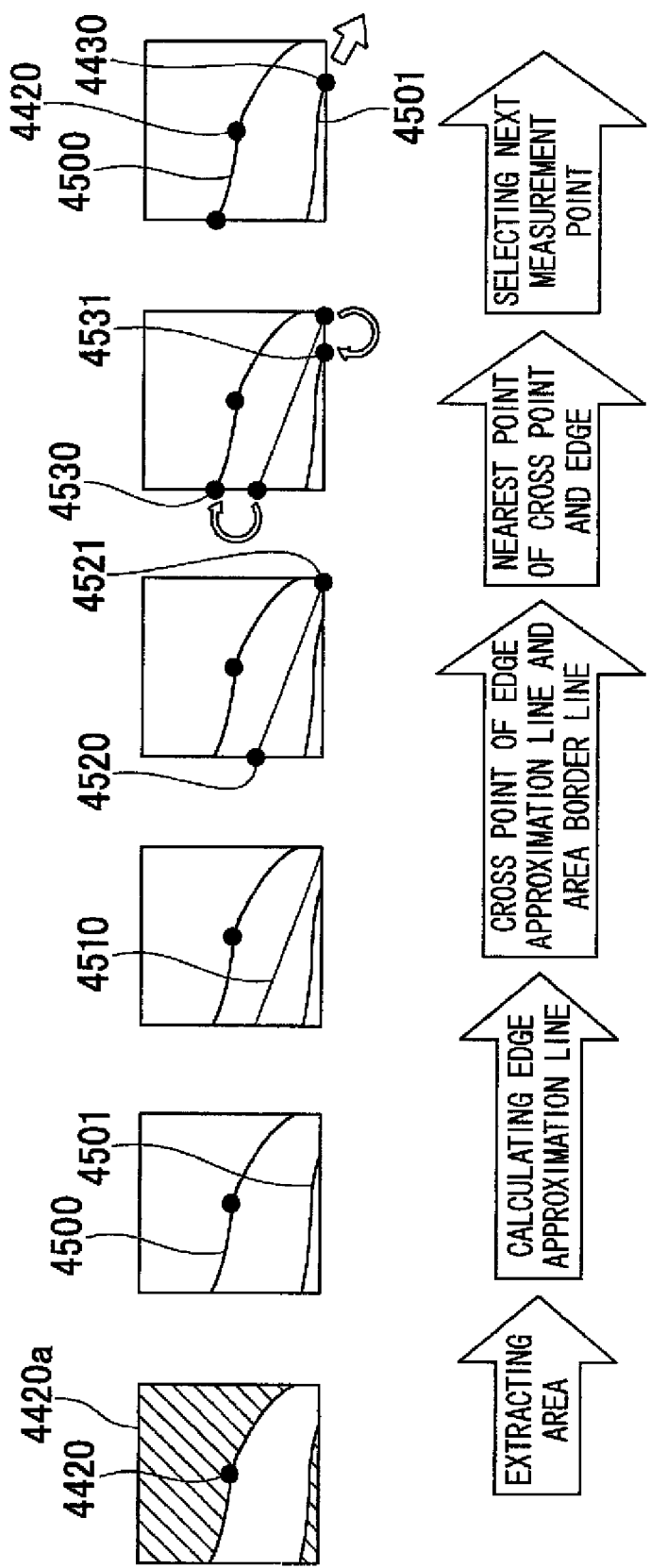
FIG. 54 explains the problem in the second embodiment of the present invention for reference.

FIG. 54 describes a procedure of searching a measurement point sequentially in the measurement point area 4420a. To start with, edges 4500 and 4501 are extracted based on an image obtained by undergoing a grayscale conversion in the measurement point area 4420a. Subsequently, an edge approximation line 4510 is calculated by approximating the extracted edges 4500 and 4501; and cross-points 4520 and 4521 located on the cross-points of the edge approximation line 4510 and an area border line are calculated. In addition, nearest points 4530 and 4531 are calculated with respect to the calculated cross-point and the edges 4500 and 4501.

The nearest point 4531, which is the farther one of the nearest points 4530 and 4531 relative to the previously obtained measurement point subsequent to the measurement point 4420, is a measurement point 4430 that undergoes a next measurement. The measurement point 4430 is positioned differently on the edge 4500, i.e., in contrast to the measurement point 4420 positioned on the edge 4500, Sometimes, any measurement points positioned on a same edge cannot be extracted desirably since two or more edges extracted in a single measurement area sometimes cause two continuously detected measurement points not to be positioned on the same edge.

Figure 53E:
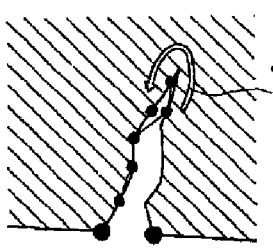
Figure 53I:
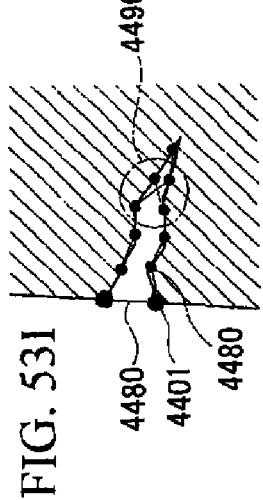

Searching of measurement points continues in a direction indicated by an arrow 4440 as illustrated in FIG. 53E subsequent to the extraction of measurement point 4430 as illustrated in FIG. 53D. In a case as illustrated in FIG. 53F, searching a measurement point next to a measurement point 4450 provides an image extracted within a measurement point area 4450a around the measurement point 4450.

Figure 55:
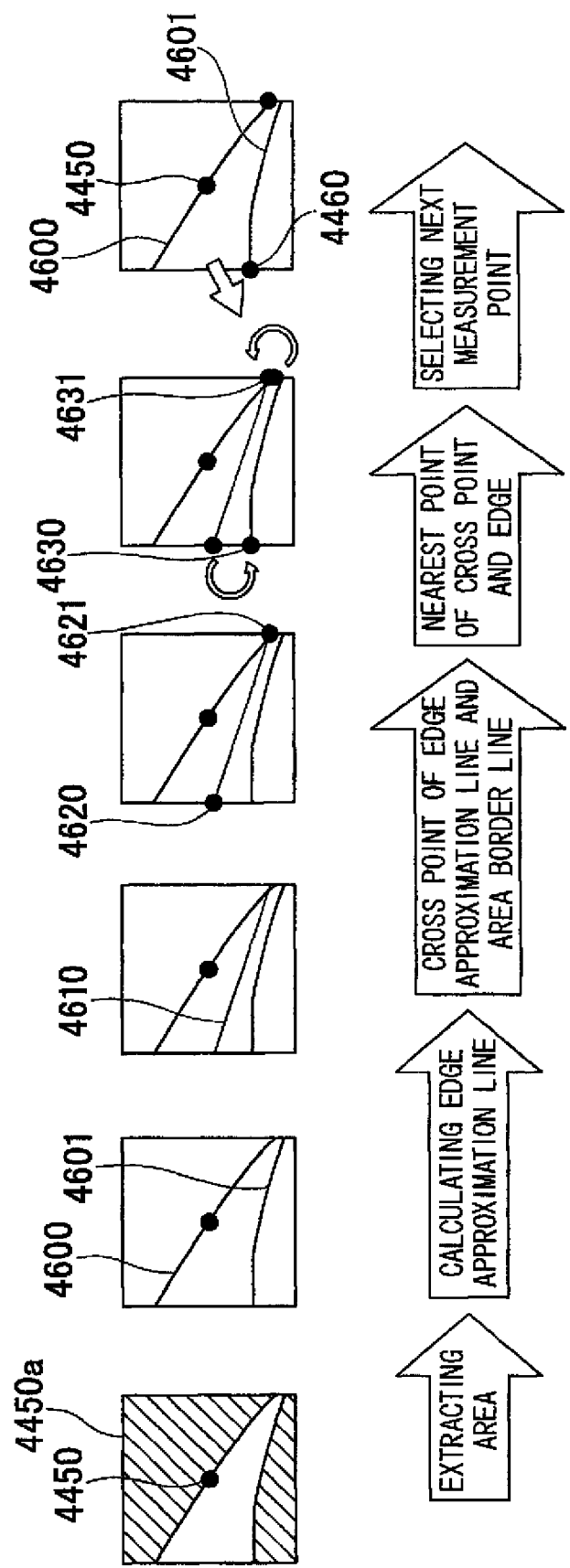
FIG. 55 explains the problem in the second embodiment of the present invention for reference.

FIG. 55 describes a procedure of sequential search conducted associated with a measurement point in the measurement point area 4450a. To start with, edges 4600 and 4601 are extracted based on an image having undergone grayscale conversion in the measurement point area 4450a. Subsequently, an edge approximation line 4610 is calculated by approximating the extracted edges 4600 and 4601; and cross-points 4620 and 4621 located on the cross-points of the edge approximation line 4610 and an area border line are calculated. In addition, nearest points 4630 and 4631 are calculated with respect to the calculated cross-point and the edges 4600 and 4601.

The nearest point 4630, which is the farther one of the nearest points 4630 and 4631 relative to the previously obtained measurement point prior to the measurement point 4450, is a measurement point 4460 that undergoes a next measurement. The measurement point 4450 is positioned differently on the edge 4600, i.e., in contrast to the measurement point 4460 positioned on the edge 4601.

Searching of measurement points continues in a direction indicated by an arrow 4470 as illustrated in FIG. 53H subsequent to the extraction of the measurement point 4460 as illustrated in FIG. 53G The searching of measurement point finishes upon extracting a measurement point 4480 having a predetermined two-dimensional distance or shorter from the reference point 4401; thus, the obtained measurement point undergoes a registration as a loss-composing point. The line segments, constituting the loss outline 4480 and obtained by joining the loss-composing points, crossing in an area 4490 provide a twisted shape to the loss outline 4480.

To address this, the endoscope apparatus according to the second embodiment is capable of detecting the twisted shape of a loss outline and adjusting the loss-composing points to disentangle the twisted shape.

Figure 56:
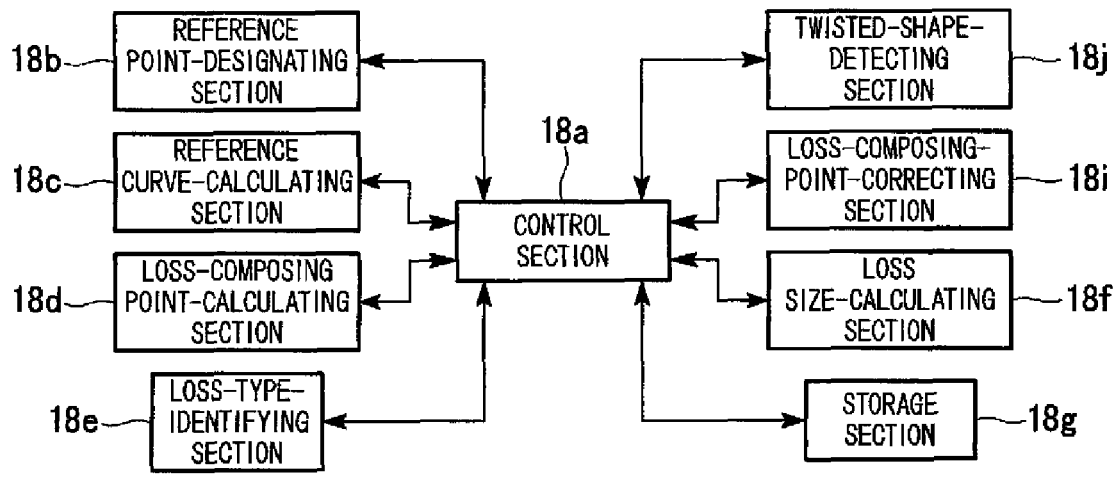
FIG. 56 is a block diagram showing a configuration of a measurement-processing section provided in an endoscope apparatus according to the second embodiment of the present invention.

FIG. 56 illustrates the configuration of the measurement-processing section 18 according to the present embodiment. New components provided to the measurement-processing section 18 as illustrated in FIG. 2 are a twisted-shape-detecting section 18j (twisted-detection unit) and a loss-composing-point-correcting section 18i (loss-composing-point-correcting unit). The twisted-shape-detecting section 18j conducts a detective processing of a twisted, i.e., specifies whether or not the loss outline is of a twisted shape. The loss-composing-point-correcting section 18i, upon detecting a twisted shape of the loss outline by using the twisted-shape-detecting section 18j, corrects the image coordinates of loss-composing points so as to disentangle the twisted shape. Other configurations are the same as the previously described in the first embodiment.

Figure 57:
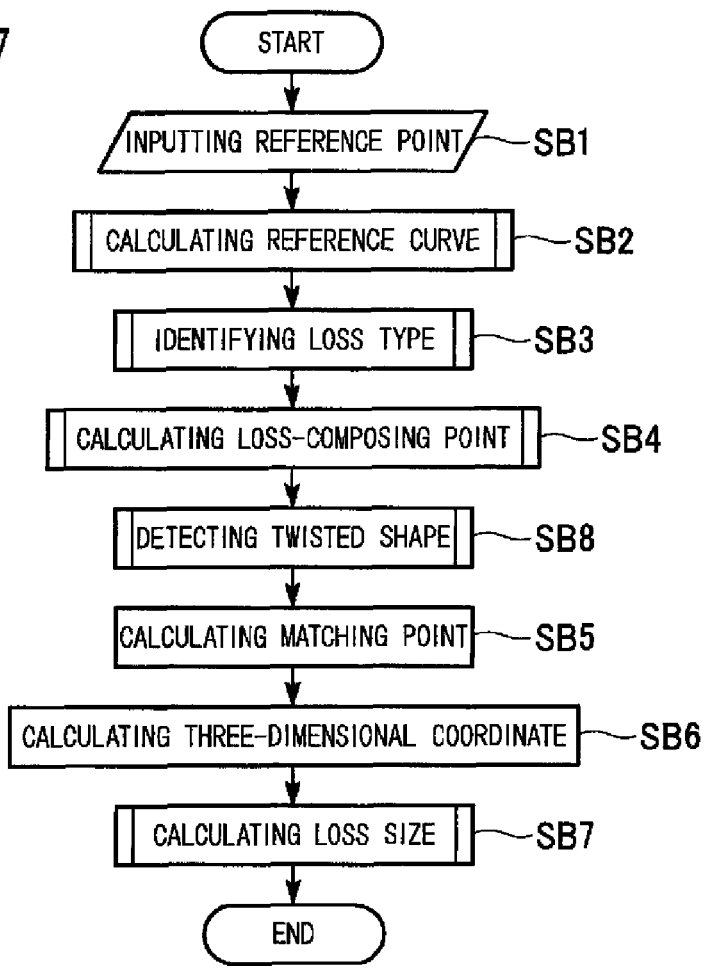
FIG. 57 is a flowchart showing the procedure of the loss measurement in the second embodiment of the present invention.

A procedure of loss measurement according to the present embodiment will be explained next. FIG. 57 illustrates a procedure of loss measurement. Processes conducted in steps SB1 to SB4 are the same as those conducted in the steps SB1 to SB4 shown in FIG. 13. Subsequent to the step SB4 having obtained the image coordinates of the loss-composing points calculated by the loss-composing point-calculating section 18*d*, the twisted-shape-detecting section 18*j* specifies whether or not the loss outline has a twisted shape. The loss-composing-point-correcting section 18*i*, upon detecting a twisted shape of the loss outline, corrects the image coordinates of loss-composing points so as to disentangle the twisted shape (step SB8). The processes of the aforementioned steps SB5 to SB7 subsequent to the step SB8 are the same as those of the steps SF5 to SF7 of FIG. 13.

FIRST OPERATIONAL EXAMPLE

Figure 58:
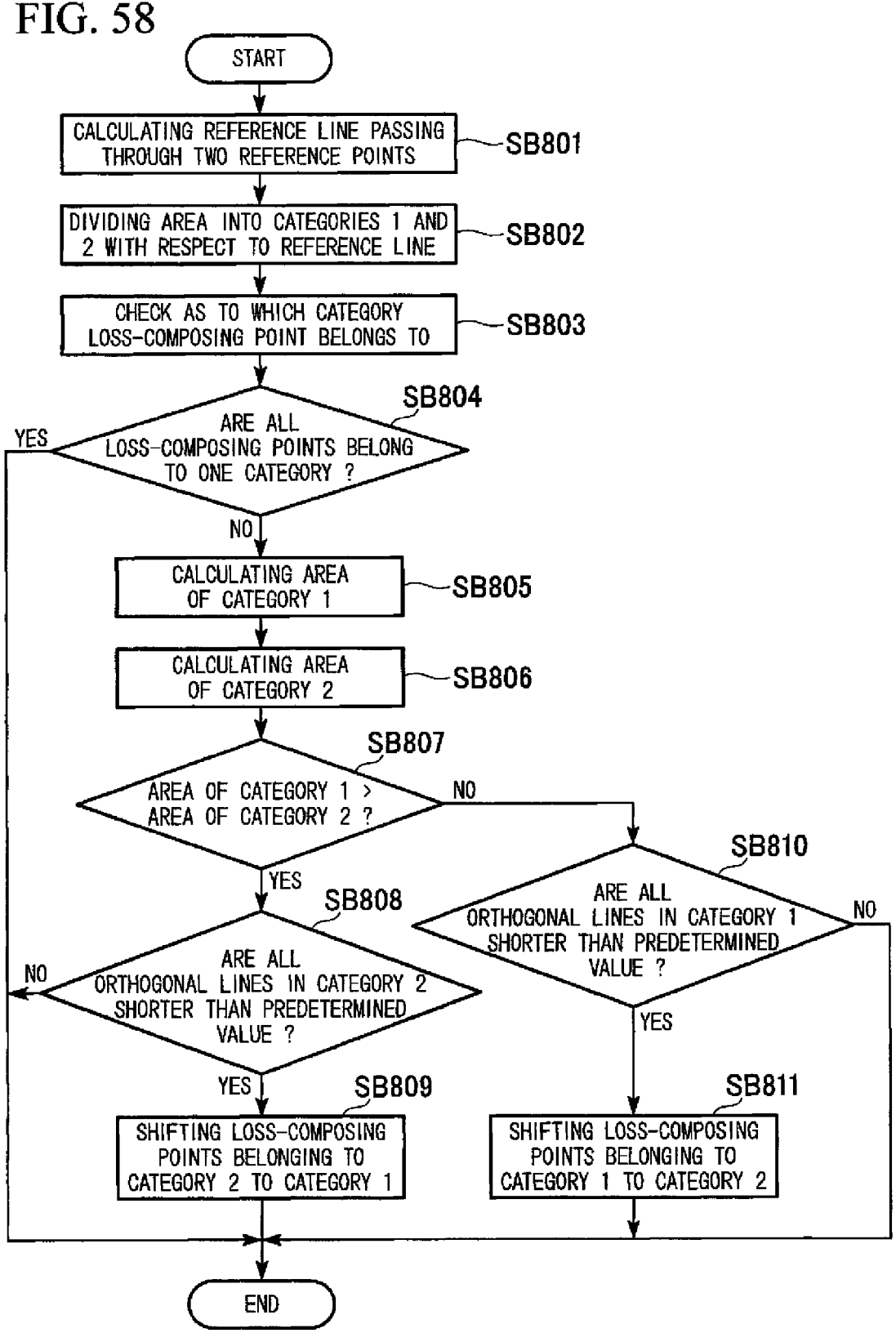
FIG. 58 is a flowchart showing a procedure of a twisted-shape detection process in the second embodiment (first operational example) of the present invention.

Details are explained as follows with respect to a process for detecting a twisted shape in the step SB8 as illustrated in FIG. 57. To start with, a first operational example will be explained with reference to FIG. 58. The first operational example relates to a side loss. FIGS. 59A to 59D illustrating the processes for detecting a twisted shape schematically are also referred to if necessary. Upon receiving details, e.g., image coordinates of loss-composing points (including two reference points) calculated in the step SB4 supplied by the control section 18*a*, the twisted-shape-detecting section 18*j* calculates a reference line passing through the two reference points (step SB801). For example, a reference line 5010 as illustrated in FIG. 59A passes through reference points 5000 and 5001.

Subsequently, the twisted-shape-detecting section 18*j* divides an image area into two pieces (two areas are categories 1 and 2) with respect to a border based on the calculated reference line (step SB802). As illustrated in FIG. 59E, for example, the category 1 indicates a right area relative to a reference line 5010; and the category 2 is a left area. Subsequently the twisted-shape-detecting section 18*j* examines which one of the categories 1 and 2 each loss-composing point belongs to, based on the image coordinate of each loss-composing point (step SB803); and determines as to whether or not all the loss-composing points (except the two reference points on the reference line) locate in one of the categories (step SB804).

All the loss-composing points belonging to one of the categories indicates the absence of a detected twisted shape. A detecting process for a twisted shape finishes in this case, and the procedure moves to a process of step SB5 as shown in FIG. 57. Alternatively, existence of the loss-composing points belonging to the category 1 and of the loss-composing points belonging to the category 2 indicates a detection of a twisted shape, thereby conducting the following process. FIG. 59B relates to detecting of a twisted shape and illustrates an example having loss-composing points existing in both the categories 1 and 2.

Details regarding coordinates of the loss-composing points and reference lines, etc. are input from the twisted-shape-detecting section 18*j* to the loss-composing-point-correcting section 18*i* via the control section 18*a* upon detecting the twisted shape. The loss-composing-point-correcting section 18*i* calculates an area defined by the loss-composing points and the reference line belonging to the category 1 (step SB805). Similarly, the loss-composing-point-correcting section 18*i* calculates an area defined by the loss-composing points and the reference line belonging to the category 2 (step SB806). As illustrated in FIG. 59C, an area 5020, defined by the loss-composing points and the reference line that locate in the category 1, is calculated in the step SB805; and a sum of areas 5021*a* and 5021*b*, defined by the loss-composing points and the reference line that locate in the category 2, is calculated in the step SB806.

Figure 60:
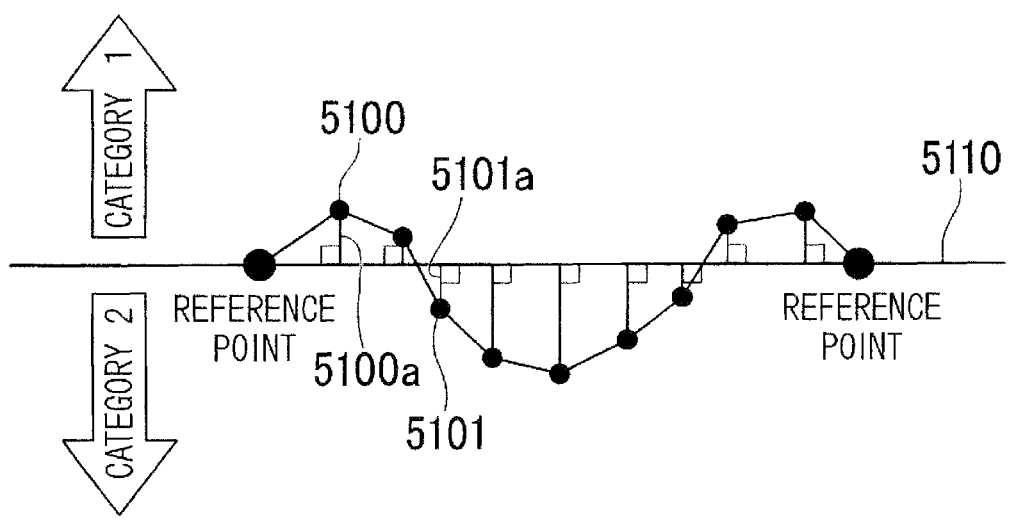
FIG. 60 explains for reference a method for calculating areas of categories 1 and 2 for use in a twisted-shape detection process in the second embodiment (first operational example) of the present invention.

The areas of categories 1 and 2 according to the present embodiment are defined as follows. As illustrated in FIG. 60, the area of the category 1 is indicated by a sum of a normal 5100*a* extending to a reference line 5110 orthogonally from a loss-composing point 5100 belonging to the category 1. Also, the area of the category 2 is indicated by a sum of a normal 5101*a* extending to a reference line 5110 orthogonally from a loss-composing point 5101 belonging to the category 2.

The loss-composing-point-correcting section 18*i* subsequent to the step SB806 compares the area of the category 1 with the area of the category 2 (step SB807). The loss-composing-point-correcting section 18*i* in a case of the area of the category 1>the area of the category 2 determines as to whether or not all the normals extending from the loss-composing points belonging to the category 2 to the reference line have a predetermined length or shorter (step SB808). If the length of a normal extending from any one of the loss-composing points belonging to the category 2 to the reference line exceeds the predetermined value, the process of detecting a twisted shape finishes without disentangling the twisted shape; and the procedure moves to the step SB5 shown in FIG. 57.

Alternatively, if all the normals have the predetermined length or shorter, the loss-composing-point-correcting section 18*i* shifts the loss-composing points belonging to the category 2 toward the category 1 (step SB809). This state of image coordinates of the loss-composing points is corrected so that the loss-composing points come onto the reference line, or in the vicinity of the category 1 relative to the reference line. For example, the positions of the loss-composing points 5030 and 5031 having belonged to the category 2 as illustrated in FIG. 59C are corrected to locate in the category 1 (see FIG. 59D). The detecting process for a twisted shape finishes up to this point, and the procedure moves to a process of step SB5 as shown in FIG. 57.

So the twisted shape can be disentangled by shifting the loss-composing points belonging to the category 2 to the category 1, comparison is made between the areas of the categories 1 and 2 in the step SB807 to determine as to which category of the loss-composing points should be shifted. The loss-composing points belonging to the smaller area category are shifted to minimize changes in loss shape or loss area. The twisted shape-detection process finishes without disentangling the twisted shape upon finding the length of the normal extending from any one of the loss-composing points belonging to the category 2 to the reference line based on decision made in the step SB808 because shifting this case of loss-composing points may change the loss shape or the loss area significantly, which may affect measurement accuracy.

Decision made in the step SB807 indicating the area of the category 1<the area of the category 2 causes the loss-composing-point-correcting section 18*i* to determine as to whether or not the all the normals extending from the loss-composing points belonging to the category 1 to the reference line have a predetermined length or shorter (step SB810). If the length of a normal extending from any one of the loss-composing points belonging to the category 1 to the reference line exceeds the predetermined value, the process of detecting a twisted shape finishes without disentangling the twisted shape; and the procedure moves to the step SB5 shown in FIG. 57.

Alternatively, if all the normals have the predetermined length or shorter, the loss-composing-point-correcting section 18*i* shifts the loss-composing points belonging to the category 1 toward the category 2 (step SB811). This state of image coordinates of the loss-composing points is corrected so that the loss-composing points come onto the reference line, or in the vicinity of the category 2 relative to the reference line. The detecting process for a twisted shape finishes up to this point, and the procedure moves to a process of step SB5 as shown in FIG. 57.

The previously explained twisted shape-detecting process disentangles the twisted shape in a side loss, thereby enabling calculation of loss area. The area of each category, i.e., the sum of normals associated with each loss-composing point belonging to each category may be determined based on an result obtained by making a comparison with a predetermined value instead of determining each length of normals extending from the loss-composing points belonging to the category 1 or 2 based on an result obtained by making comparison with the predetermined value in the steps SB808 and SB810 that carry out the previously explained twisted shape-detecting process. Alternatively, a ratio of the area of the category 1 to the area of the category 2 may be determined based on an result obtained by making a comparison with the predetermined value.

The following modification may be adaptable to the configuration based on the decision made in the steps SB808 and SB810 where the twisted shape-detecting process finishes without disentangling the twisted shape upon finding out that the normal extending from any one of the loss-composing points to the reference line has a predetermined length or longer. For example, details of the loss-composing points belonging to the category 2 may not be used as long as a calculated loss area tolerates an error in the loss measurement. Otherwise, three-dimensional areas of the categories 1 and 2 may be calculated separately based on the image coordinates of loss-composing points and the details of the reference line to obtain a loss area represented by the sum of the calculated three-dimensional areas.

SECOND OPERATIONAL EXAMPLE

Figure 61:
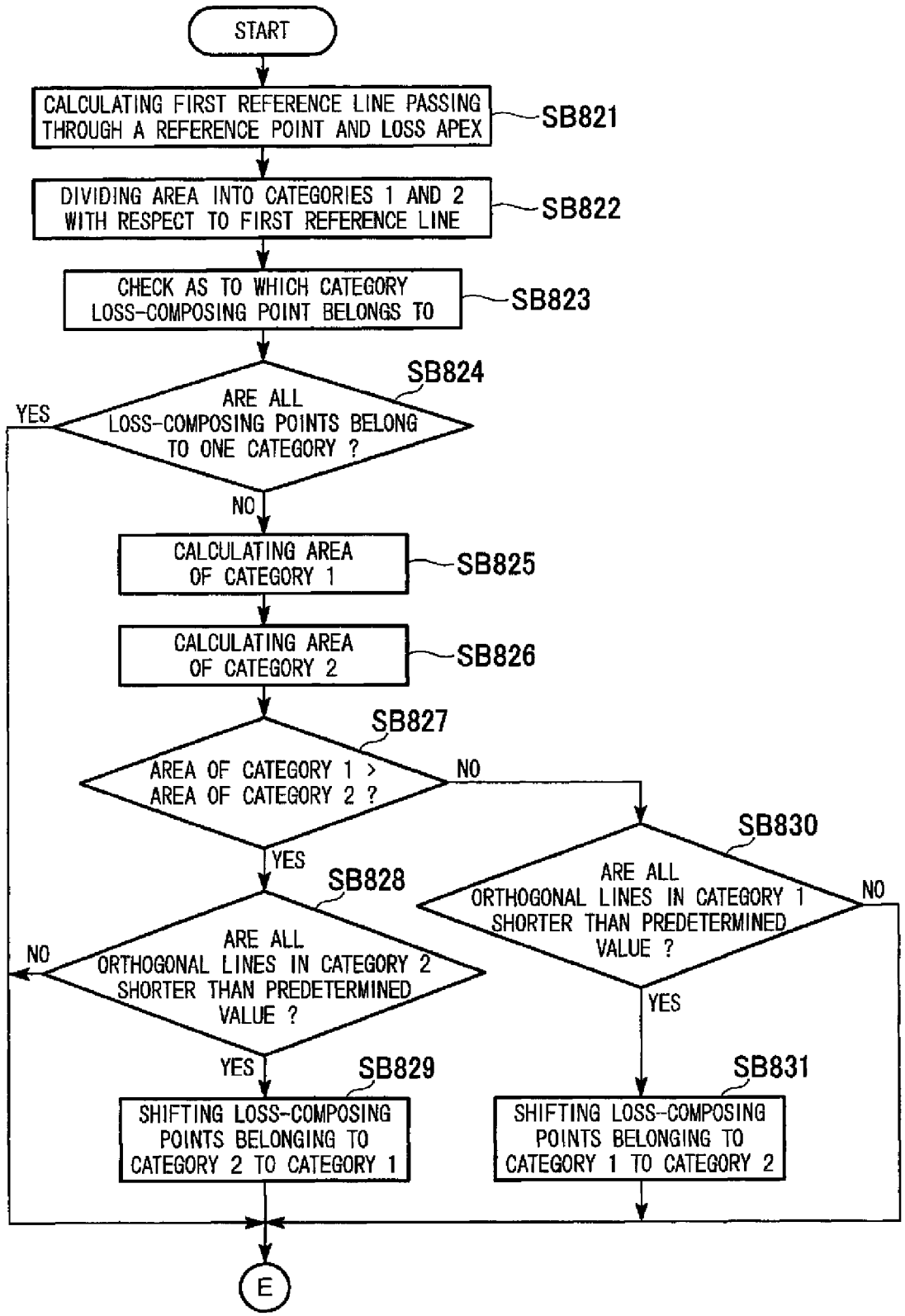
FIG. 61 is a flowchart showing a procedure of a twisted-shape detection process in the second embodiment (first operational example) of the present invention.
Figure 62:
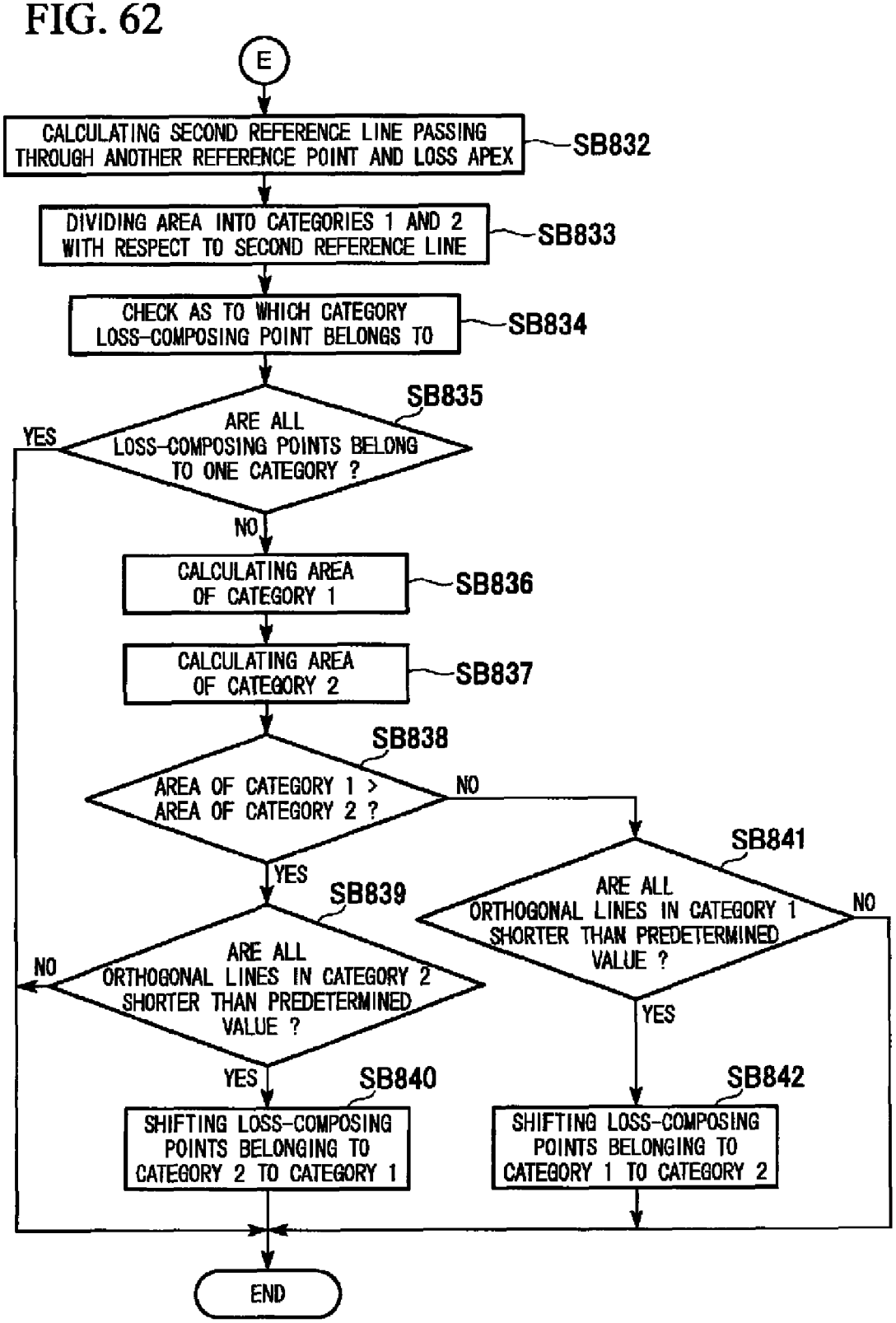
FIG. 62 is a flowchart showing the procedure of the twisted-shape detection process in the second embodiment (first operational example) of the present invention.
Figure 64:
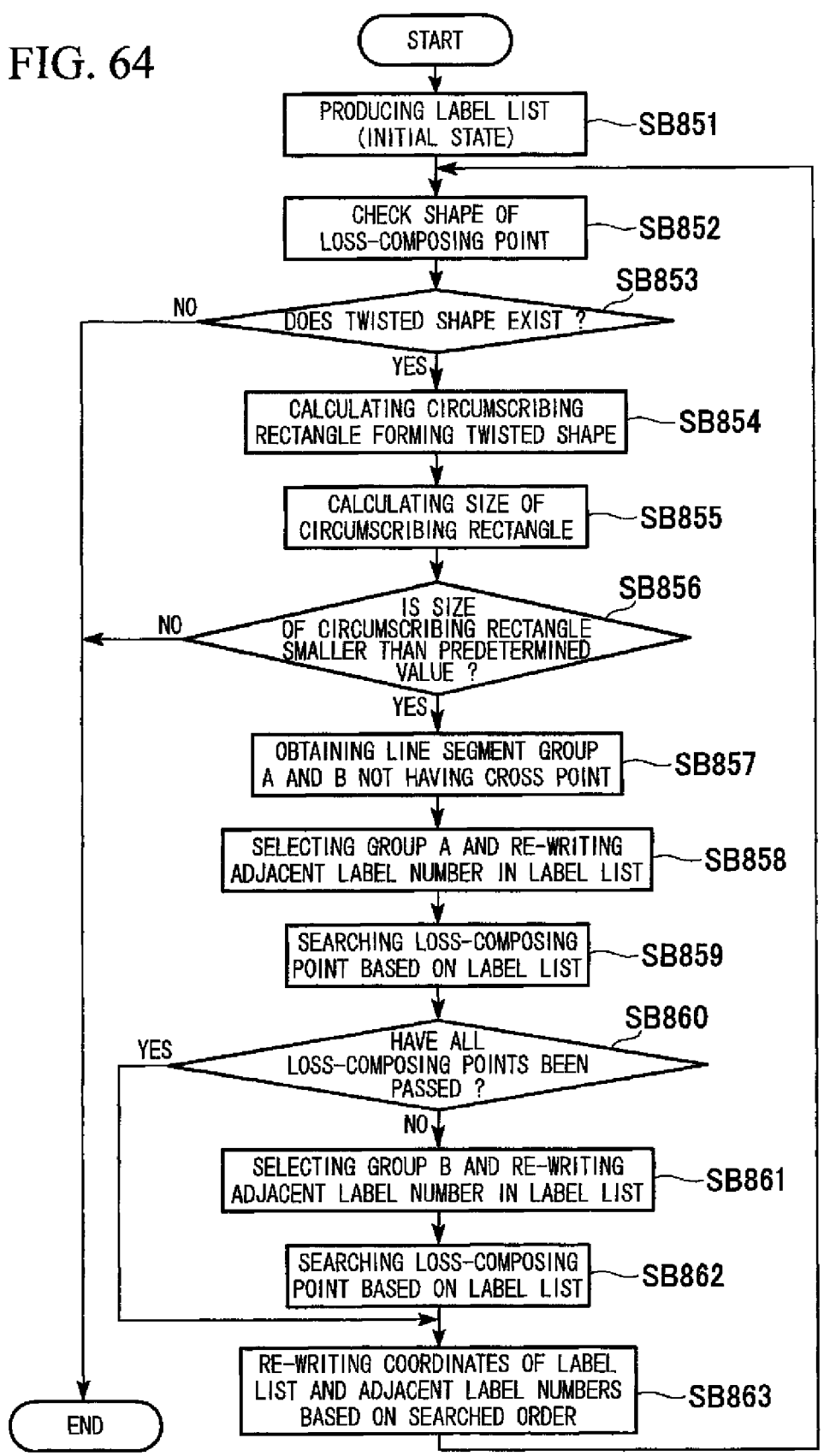
FIG. 64 is a flowchart showing the procedure of the twisted-shape detection process in the second embodiment (third operational example) of the present invention.

A second operational example will be explained with reference to FIGS. 61 and 62. The second operational example relates to an apex loss. FIGS. 63A to 63H illustrating the processes for detecting a twisted shape schematically are also referred to if necessary. A shifting of loss-composing points is based on two reference lines established in the second operational example in contrast to the first operational example establishing a reference line to shift loss-composing points to disentangle the twisted shape. Upon receiving the details of image coordinates of loss-composing points (including two reference points and loss apex) calculated in the step SB4 supplied by the control section 18a, the twisted-shape-detecting section 18j calculates a first reference line passing through one of the two reference points and the first reference line passing through the loss apex (step SB821). For example, a reference line 5410 as illustrated in FIG. 63A passing through a reference point 5400 and a loss apex 5402 is calculated.

Subsequently, the twisted-shape-detecting section 18j divides an image area into two pieces (two areas are the categories 1 and 2) with respect to a border based on the calculated first reference line (step SB822). As illustrated in FIG. 63E, for example, the category 1 indicates a right area relative to the first reference line 5410; and the category 2 is a left area. Subsequently, the twisted-shape-detecting section 18j examines which one of the categories 1 and 2 each loss-composing point belongs to based on the image coordinate of each loss-composing point (step SB823); and determines as to whether or not all the loss-composing points (except the reference point on the first reference line and the loss apex) locate in one of the categories (step SB824).

All the loss-composing points belonging to one of the categories indicates the absence of a detected twisted shape. This case of procedure moves to a step SB832 as shown in FIG. 62. Alternatively, existence of the loss-composing points belonging to the category 1 and of the loss-composing points belonging to the category 2 indicates a detection of a twisted shape, thereby conducting the following process. FIG. 63B relates to a detecting of twisted shape and illustrates an example having loss-composing points existing in both the categories 1 and 2.

Details regarding the coordinates of the loss-composing points and the first reference line, etc. are input from the twisted-shape-detecting section 18j to the loss-composing-point-correcting section 18i via the control section 18a upon detecting the twisted shape. The loss-composing-point-correcting section 18i calculates an area (i.e., the area of the category 1) defined by the loss-composing points belonging to the category 1, and the first reference line (step SB825). Similarly, the loss-composing-point-correcting section 18i calculates an area defined by the loss-composing points and the first reference line that locate in the category 2 (step SB826). The areas of the categories 1 and 2 are calculated similarly to the first operational example that obtains the sum of length of normals extending from the loss-composing points belonging to each category to the first reference line. As illustrated in FIG. 63C, the area 5420, defined by the loss-composing points and the first reference line that locate in the category 1, is calculated in the step SB825; and the area 5421 defined by the loss-composing points and the first reference line that locate in the category 2, is calculated in the step SB826.

Subsequently, the loss-composing-point-correcting section 18i compares the area of the category 1 with the area of the category 2 (step SB827). The loss-composing-point-correcting section 18i in a case of the area of the category 1>the area of the category 2 determines as to whether or not all the normals extending from the loss-composing points belonging to the category 2 to the first reference line have a predetermined length or shorter (step SB828). If the length of a normal extending from any one of the loss-composing points belonging to the category 2 to the reference line exceeds the predetermined length, the procedure moves to a step SB832 shown in FIG. 62 without disentangling the twisted shape.

Alternatively, if all the lengths of the normals have the predetermined length or shorter, the loss-composing-point-correcting section 18i shifts the loss-composing points belonging to the category 2 toward the category 1 (step SB829). This state of image coordinates of the loss-composing points is corrected so that the loss-composing points come onto the first reference line, or in the vicinity of the category 1 relative to the first reference line. For example, the position of the loss-composing point 5430 having belonged to the category 2 as illustrated in FIG. 51C is corrected to locate in the category 1 (see FIG. 63D). Subsequently, the procedure moves to the step SB832 as shown in FIG. 62.

Decision made in the step SB827 indicating the area of the category 1 □ the area of the category 2 causes the loss-composing-point-correcting section 18i to determine as to whether or not all the normals extending from the loss-composing points belonging to the category 1 to the first reference line have a predetermined length or shorter (step SB830). If the normal extending from any one of the loss-composing points belonging to the category 1 to the reference line exceeds the predetermined length, the procedure moves to a step SB832 shown in FIG. 62 without disentangling the twisted shape.

Alternatively, if all the normals have the predetermined length or shorter, the loss-composing-point-correcting section 18i shifts the loss-composing points belonging to the category 1 toward the category 2 (step SB831). This state of image coordinates of the loss-composing points is corrected so that the loss-composing points come onto the first reference line, or in the vicinity of the category 1 relative to the first reference line. Subsequently, the procedure moves to the step SB832 as shown in FIG. 62.

The twisted-shape-detecting section 18h upon finishing the process associated with the first reference line calculates a second reference line passing the other one of the two reference points and the loss apex (step SB832). For example, a reference line 5411 as illustrated in FIG. 63E passing through a reference point 5401 and the loss apex 5402 is calculated.

Subsequently, the twisted-shape-detecting section 18j divides an image area into two pieces (two areas are the categories 1 and 2) with respect to a border based on the calculated second reference line (step SB833). As illustrated in FIG. 63F, for example, the category 1 indicates a left area relative to the second reference line 5411; and the category 2 is a right area. Subsequently, the twisted-shape-detecting section 18j examines which one of the categories 1 and 2 each loss-composing point belongs to based on the image coordinate of each loss-composing point (step SB834); and determines as to whether or not all the loss-composing points (except the reference point on the second reference line and the loss apex) locate in one of the categories (step SB835).

All the loss-composing points belonging to one of the categories indicates the absence of a detected twisted shape. A detecting process for a twisted shape finishes in this case, and the procedure moves to a process of step SB5 as shown in FIG. 57. Alternatively, existence of the loss-composing points belonging to the category 1 and of the loss-composing points belonging to the category 2 indicates a detection of a twisted shape, thereby conducting the following process. FIG. 63F relates to a detecting of twisted shape and illustrates an example having loss-composing points existing in both the categories 1 and 2.

Details regarding the coordinates of the loss-composing points and the second reference line, etc. are input from the twisted-shape-detecting section 18j to the loss-composing-point-correcting section 18i via the control section 18a upon detecting the twisted shape. The loss-composing-point-correcting section 18i calculates an area (i.e., the area of the category 1) defined by the loss-composing points and the second reference line that locate in the category 1 (step SB836). Similarly, the loss-composing-point-correcting section 18i calculates an area defined by the loss-composing points and the second reference line that locate in the category 2 (step SB837). As illustrated in FIG. 63G, the area 5422, defined by the loss-composing points and the second reference line that locate in the category 1 is calculated in the step SB836; and the area 5423 defined by the loss-composing points and the second reference line that locate in the category 2, is calculated in the step SB837.

Subsequently, the loss-composing-point-correcting section 18i compares the area of the category 1 with the area of the category 2 (step SB838). The loss-composing-point-correcting section 18i in a case of the area of the category 1>the area of the category 2 determines as to whether or not all the normals extending from the loss-composing points belonging to the category 2 to the second reference line have a predetermined length or shorter (step SB839). If the normal extending from any one of the loss-composing points belonging to the category 2 to the second reference line has the predetermined length or longer, the process of detecting a twisted shape finishes without disentangling the twisted shape; and the procedure moves to the step SB5 shown in FIG. 48.

Alternatively, if all the normals have the predetermined length or shorter, the loss-composing-point-correcting section 18i shifts the loss-composing points belonging to the category 2 toward the category 1 (step SB840). This state of image coordinates of the loss-composing points is corrected so that the loss-composing points locate in the second reference line, or in the vicinity of the category 1 relative to the second reference line. For example, the position of a loss-composing point 5431 having belonged to the category 2 as illustrated in FIG. 51G is corrected to locate in the category 1 (see FIG. 63I). The detecting process for a twisted shape finishes up to this point, and the procedure moves to a process of step SB5 as shown in FIG. 48.

Decision made in the step SB838 indicating the area of the category 11 the area of the category 2 causes the loss-composing-point-correcting section 18i to decides as to whether or not all the normals extending from the loss-composing points belonging to the category 1 to the second reference line have a predetermined length or shorter (step SB841). If the a normal extending from any one of the loss-composing points belonging to the category 1 to the second reference line has the predetermined length or longer, the process of detecting a twisted shape finishes without disentangling the twisted shape; and the procedure moves to the step SB5 shown in FIG. 57.

Alternatively, if all the normals have the predetermined length or shorter, the loss-composing-point-correcting section 18i shifts the loss-composing points belonging to the category 1 toward the category 2 (step SB842). This state of image coordinates of the loss-composing points are corrected so that the loss-composing points come onto the second reference line, or in the vicinity of the category 2 relative to the second reference line. The detecting process for a twisted shape finishes up to this point, and the procedure moves to a process of step SB5 as shown in FIG. 57.

The previously explained twisted shape-detecting process disentangles the twisted shape in an apex loss, thereby enabling calculation of loss area. The previously explained twisted shape-detecting process may be subject to modification the same as that conducted to the first operational example.

THIRD OPERATIONAL EXAMPLE

A third modified example will be explained next. The third operational example relates to a narrow and complex shape of a loss as illustrated in FIGS. 52A to 52C. Details are explained as follows with respect to a process for detecting a twisted shape in the step SB8 as illustrated in FIG. 57. Upon receiving details, e.g. image coordinates of loss-composing points (including two reference points) calculated in the step SB4 supplied by the control section 18a, the twisted-shape-detecting section 18j produces a label list of loss-composing points (step SB851).

FIG. 65A describes an initial state of details of the label list. The label list includes a label number per loss-composing point; an image coordinate value of the loss-composing points; and two adjoining label numbers indicating which one of the loss-composing points adjoins to each loss-composing point. FIGS. 66A to 66D schematically describe the positions of the loss-composing points on the image corresponding to the label list shown in FIG. 65A. A loss outline is formed by line segments joining loss-composing points. The number found near each loss-composing point indicates a label number included in the label list.

Figure 66A:
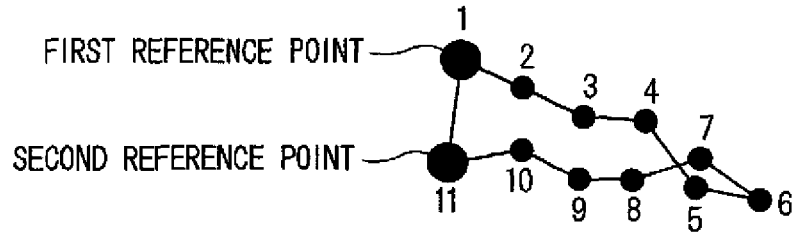
FIGS. 66A to 66D explain for reference loss-composing points for use in the twisted-shape detection process in the second embodiment (third operational example) of the present invention.
Figure 66B:
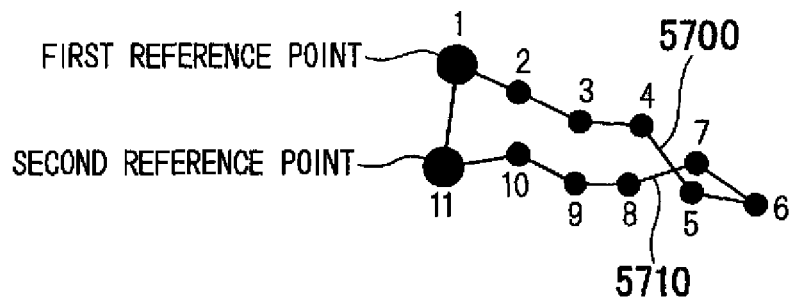

A primary label number and a final label number are numbered the two reference points. FIG. 66A illustrates an example having a label number 1 added to the first reference point; and a label number 11 added to the second reference point. Label numbers added to other loss-composing points are incremented in an extracted order. The loss-composing point adjoining each loss-composing point can be discovered based on two adjoining label numbers. For example, the loss-composing points adjoining the loss-composing point having the label number 1 (first reference point) are the loss-composing points having the label number 11 (second reference point) and the loss-composing points having the label number 2.

The twisted-shape-detecting section 18j subsequent to the step SB851 examines the shape of the loss outline based on the image coordinate of the loss-composing point (step SB852). Examination of the correlation of the line segment joining the adjoining loss-composing points based on the adjoining label numbers of the label list may provide the shape of the loss outline. Accordingly, it can be examined as whether or not the loss outline has a twisted shape. Examination as to whether or not the line segments, which joins the adjoining loss-composing points based on the adjoining label numbers of the label list, cross each other (i.e., as to whether or not there are two line segments crossing with each other exist) may provide the presence of the twisted shape. An example shown in FIG. 66B reveals that the loss outline has a twisted shape since a line segment 5700 joining the loss-composing points corresponding to label numbers 4 and 5 crosses with a line segment 5710 joining the loss-composing points corresponding to label numbers 7 and 8.

The twisted-shape-detecting section 18j determines based on an result obtained in a processing of the step SB852 as to whether the loss outline has a twisted shape (step SB853). The absence of a twisted shape in the loss outline finishes a detecting process for a twisted shape in this case, and the procedure moves to a process of step SB5 as shown in FIG. 57.

Figure 66C:
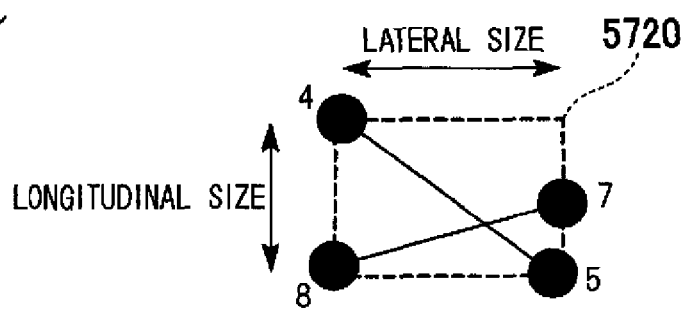

The twisted-shape-detecting section 18j upon detecting the twisted shape in the loss outline inputs details including the label list, etc. to the loss-composing-point-correcting section 18i via the control section 18a. The loss-composing-point-correcting section 18i calculates four circumscribed rectangle associated with the twisted shape (step SB854). An example calculated in the step SB854 is an circumscribed rectangle 5720 as illustrated in FIG. 66C. The circumscribed rectangle is a figure to determine as to whether or not the twisted shape should be disentangled. The guideline is not limited to an circumscribed rectangle.

Subsequently, the loss-composing-point-correcting section 18i calculates the size of the circumscribed rectangle based on a vertical size and a lateral size (step SB855). The vertical size indicates the length of the circumscribed rectangle 5720 in a vertical direction as illustrated in FIG. 66. The lateral size indicates the length of the circumscribed rectangle 5720 in a horizontal direction. In addition, the size of the circumscribed rectangle may be a product of the vertical size and the lateral size. The loss-composing-point-correcting section 18i specifies whether or not the size calculated in the step SB855 has the predetermined or smaller value (step SB856).

The circumscribed rectangle exceeding the predetermined value in size finishes a detecting process for a twisted shape without disentangling the twisted shape, and the procedure moves to a process of step SB5 as shown in FIG. 57. The circumscribed rectangle not greater than the predetermined value in size causes the loss-composing-point-correcting section 18i to obtain two line segments that do not cross each other among different combinations of two line segments each passing through two any points of four loss-composing points associated with the twisted shape (step SB857).

Four loss-composing points corresponding to label numbers 4, 5, 7, and 8 are associated with the twisted shape among the loss-composing points shown in FIGS. 66A to 66D. The two line segments do not cross in the two combinations illustrated in FIGS. 67A and 67B included in the combinations associated with two line segments that pass through two points among the four loss-composing points. Groups A and B represent the combinations. Examples shown in FIGS. 67A and 67B are the group A representing the combination of the line segment shown in FIG. 67A and the group B representing the combination of the line segments show in FIG. 67B.

Figure 67A:
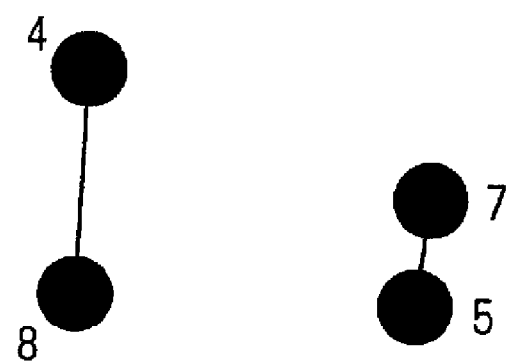
FIGS. 67A to 67B show for reference line segments of groups A and B for use in the twisted-shape detection process in the second embodiment (third operational example) of the present invention.
Figure 68A:
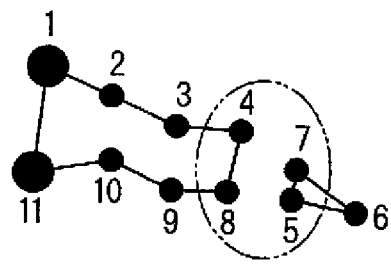
FIGS. 68A to 68D show for reference the loss-composing points for use in the twisted-shape detection process in the second embodiment (third operational example) of the present invention.

Subsequently, the loss-composing-point-correcting section 18i rewrites the adjoining label numbers of the label list based on the details of the line segments forming the group A (step SB858). The loss outline processed in this case includes the line segments that constitute the group A. FIG. 68A shows an example of the loss outline corrected to include the line segments constituting the group A shown in FIG. 67A. This case of label list in the initial state as shown in FIG. 65A must undergo changing of the adjoining label number 5 to 8 associated with the loss-composing point of label number 4; changing of the adjoining label number 4 to 7 associated with the loss-composing point of label number 5; changing of the adjoining label number 8 to 5 associated with the loss-composing point of label number 7; and changing of the adjoining label number 7 to 4 associated with the loss-composing point of label number 8. FIG. 65B describes details of the label list that has undergone the changes.

Subsequently, the loss-composing-point-correcting section 18i searches the loss-composing points based on the rewritten label list in order commencing from the loss-composing point having a first label number added thereto (step SB859); and determines as to whether or not all the loss-composing points have been passed (step SB860). Searching of the loss-composing points is conducted in order to specify as to whether or not the rewritten label list has caused the loss outline to be divided into two pieces.

The loss-composing points based on the label list as shown in FIG. 65B is searched as follows. To start with, loss-composing points corresponding to the label number 1 are selected, and the adjoining label numbers therefor are referred to. An adjoining label number 2 is assumed to be selected between the adjoining label numbers 11 and 2. Subsequently, loss-composing points corresponding to the label number 2 are selected, and the adjoining label numbers therefor are referred to. The adjoining label number that is different from a label number of the immediate and precedent searched loss-composing point is assumed to be selected between the adjoining label numbers 1 and 3. That is, 3 is selected.

Figure 68B:
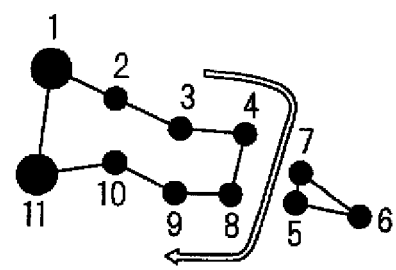

The loss-composing points corresponding to the label numbers 1, 2, 3, 4, 8, 9, 10, and 11 are searched sequentially in this order by repeating the same process (See FIG. 68B). In addition, the searching of loss-composing points finishes upon finding the adjoining label number that is the same as the label number of the loss-composing point that has undergone the searching first. The search having started from the loss-composing points corresponding to the label number 1 finishes upon searching the loss-composing point corresponding to the label number 11. Making comparison between the number of the loss-composing points, i.e., 11, recorded on the label list and the number of the loss-composing points that underwent the searching, i.e., 8, reveals that one is different from the other, thereby showing that some of the loss-composing points have not undergone the searching.

The result based on decision obtained in the step SB860 revealing that all the loss-composing points have undergone the searching indicates that a desirable loss outline has been obtained. This case of procedure moves to a step SB863. Also, the loss-composing-point-correcting section 18i conducts the aforementioned process with respect to line segments that constitute the group B if the result based on the decision obtained in the step SB860 reveals that some of the loss-composing points have not undergone the searching.

Figure 67B:
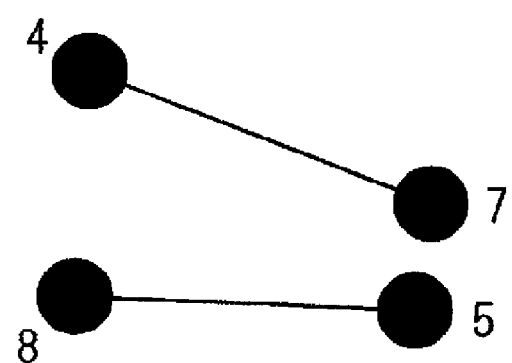
Figure 68C:
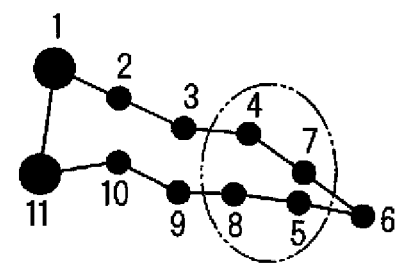

That is, the loss-composing-point-correcting section 18i rewrites the adjoining label numbers of the label list based on the details of the line segments constituting the group A (step SB861). FIG. 68C shows an example of the loss outline corrected to include the line segments constituting the group B shown in FIG. 67B. This case of a label list in the original state as shown in FIG. 65A must undergo changing of the adjoining label number 5 to 7 associated with the loss-composing point of label number 4; changing of the adjoining label number 4 to 8 associated with the loss-composing point of label number 5; changing of the adjoining label number 8 to 4 associated with the loss-composing point of label number 7; and changing of the adjoining label number 7 to 5 associated with the loss-composing point of label number 8. FIG. 65C describes details of the label list that has undergone the changes.

Subsequently, the loss-composing-point-correcting section 18i carries out sequential search of the loss-composing points starting from the loss-composing point having the first label number added thereto based on the rewritten label list (step SB862).

Figure 68D:
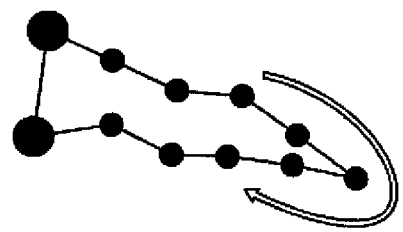

Sequential search shown in FIG. 68D conducted on the loss-composing points illustrated in FIG. 68C reveals that the search has been conducted with respect to all the loss-composing points. Thus, evidently the twisted shape of the loss outline shown in FIG. 68C has been disentangled.

The loss-composing-point-correcting section 18i subsequent to the step SB862 rewrites the image coordinate value of the label list so that an order of searching the loss-composing points conducted in the step SB862 coincides with the order of the label number; and rewrites the adjoining label number of the label list to have the same original state (step SB863). The loss-composing points have undergone the searching as shown in FIG. 68C in the order of label number 1, 2, 3, 4, 7, 6, 5, 8, 9, 10, and 11. The loss-composing points corresponding to the label number 5 and 7 have different label numbers and searching order. Therefore, the step SB863 conducts a process of switching between the image coordinate value corresponding to the loss-composing point having the label number 5 and the image coordinate value corresponding to the loss-composing point having the label number 7.

Figure 66D:
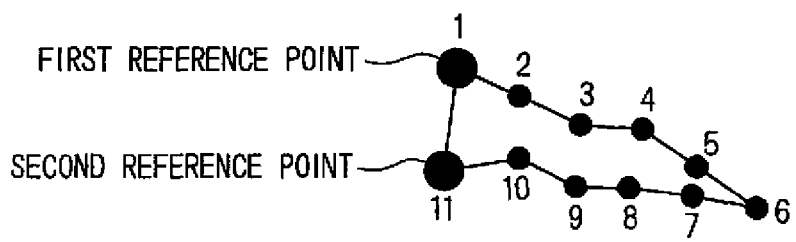

This causes the positions of the loss-composing points corresponding to the label number 5 and 7 to be switched as illustrated in FIG. 66D. In addition, the adjoining label number is rewritten to have the same status as shown in FIG. 65A. FIG. 65D describes details of the label list that has undergone the changes. The process in the step SB863 may be skipped unless required. The procedure subsequent to the step SB863 goes back to the step SB852.

The previously explained twisted shape-detecting process disentangles the twisted shape in a narrow and complex shape of loss, thereby enabling calculation of loss area. The twisted shape-detection process finishes without disentangling the twisted shape upon finding the size of the circumscribed rectangle that exceeds the predetermined value because disentangling this case of the twisted shape of the loss changes the loss shape and area significantly, thereby possibly affecting measurement accuracy.

Figure 69A:
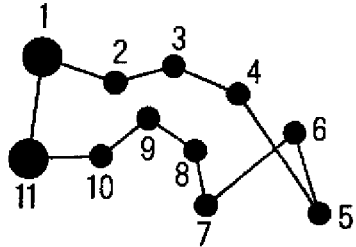
FIGS. 69A to 69D show for reference the loss-composing points for use in the twisted-shape detection process in the second embodiment (third operational example) of the present invention.
Figure 69B:
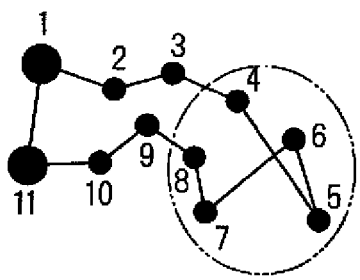
Figure 69C:
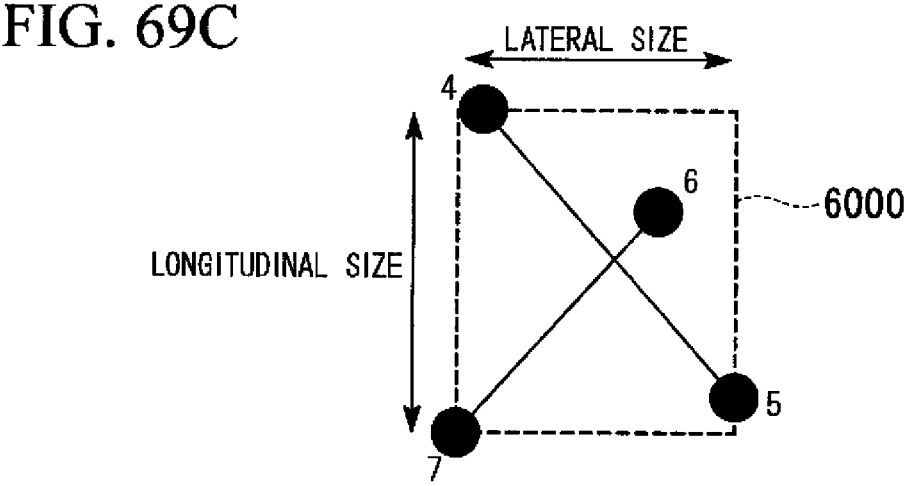
Figure 69D:
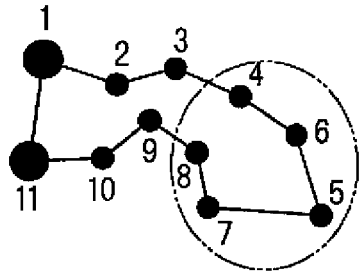

The shape of the loss outline as illustrated in FIG. 69A reveals that the loss-composing points corresponding to the label number 4, 5, 6, and 7 are associated with the twisted shape as illustrated in FIG. 69B. Significant size of the circumscribed rectangle 6000 adjoining the four loss-composing points causes the shape of the loss outline (See FIG. 69D) having undergone the disentangling of the twisted shape to vary significantly from the shape illustrated in FIG. 69. The twisted-shape-detecting process then finishes without disentangling the twisted shape in this case. It should be noted that the twisted shape may be disentangled as long as an error in the loss measurement is tolerable. The twisted-shape-detecting process conducted in the aforementioned fourth operational example may be adapted to a side loss or an apex loss.

FOURTH OPERATIONAL EXAMPLE

Next, a fourth modified example will be explained. Measurement objects in the fourth operational example are, burning (scorch) produced on a blade surface, peeling paint, or rust in a piping, etc., in contrast to the first to third operational examples having the primary object of specifying losses produced on a turbine blade edge or a compressor blade edge.

Figure 70C:
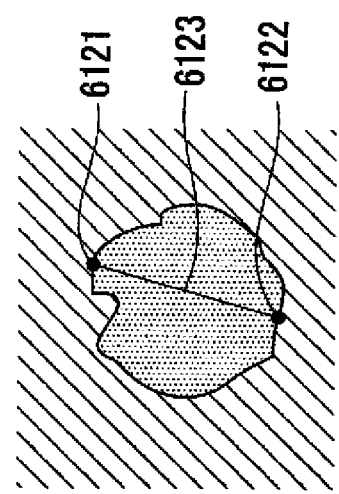
FIGS. 70A to 70C show for reference a measurement object in the second embodiment (fourth operational example) of the present invention.
Figure 70B:
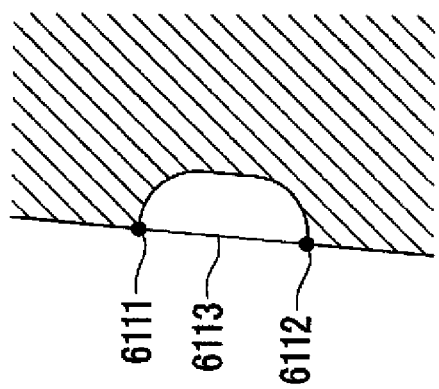
Figure 70A:
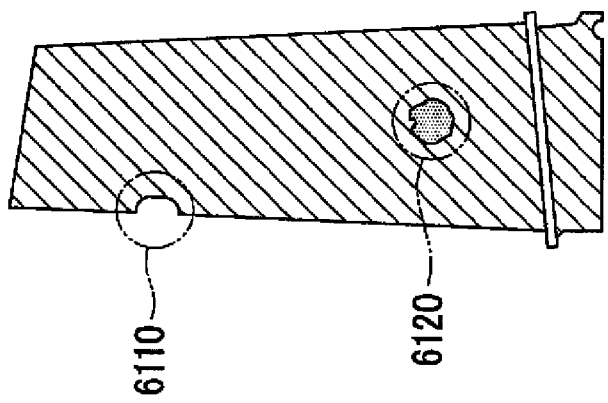

For example, a compressor blade 6100 shown in FIG. 70A has a loss 6110 formed on an edge and a burning 6120 on a surface. FIG. 70B shows an enlarged view of the loss 6110, and FIG. 70 shows an enlarged view of the burning 6120. The loss 611 has an edge on a single side relative to a line 6113 joining the end points 6111 and 6112. In contrast, the burning 6120 has two edges relative to a line 6123 connecting any points 6121, and 6122 on an outline (edge) around the burning 6120.

Figure 71A:
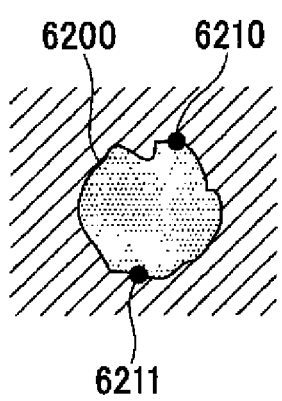
FIGS. 71A to 71E show for reference a procedure of loss measurement in the second embodiment (fourth operational example) of the present invention.
Figure 71B:
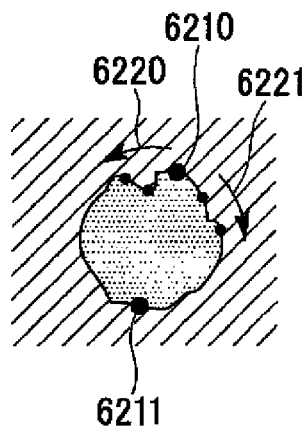

A method for conducting loss measurement will be explained with reference to FIGS. 70A to 70C as follows with respect to a measurement object that has edges on both sides of a line joining two any points on the measurement object. First, the user designates two any reference points 6210 and 6211 on a edge of the burning 6200 as illustrated in FIG. 71A. Sequential search subsequently conducted to the points between the two designated reference points positioned on the edge obtains loss-composing points (measurement points) as aforementioned in the first embodiment. Subsequently, the loss-composing points undergo the searching in two directions indicated by arrows 6220 and 6221 from the reference point 6210 to the reference point 6211 as illustrated in FIG. 71B. The reference points 4110 and 4111 instantly become a loss-starting point and a loss-ending point respectively in the fourth operational example which does not calculate a reference curve.

Figure 71C:
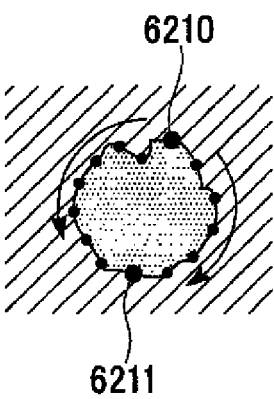
Figure 71D:
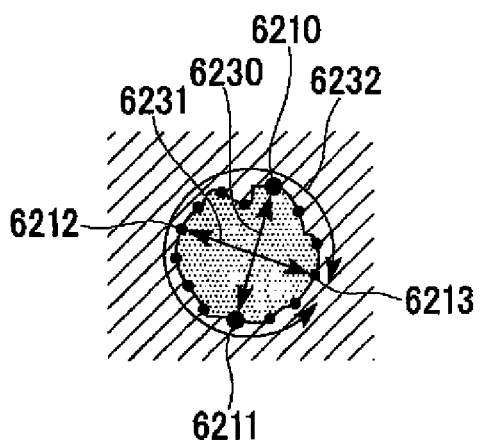

The searching of the loss-composing points finishes upon obtaining the predetermined or shorter two-dimensional distance between the loss-composing points and the reference point 6211 that have undergone the searching. FIG. 71C illustrates the loss-composing points subsequent to the searching. Subsequently, matching points corresponding to the extracted loss-composing points are calculated, and a spatial coordinate of each point is calculated. The size of the burning 6200 is calculated based on the spatial coordinate of each calculated point. The size of the calculated burning 6200 is indicated by an area based on a product of widths 6230 and 6231 and circumferential length 6232 of the burning 6200 as illustrated in FIG. 71D.

Figure 71E:
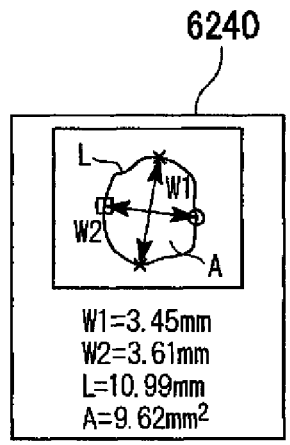

The width 6230 is a spatial distance between the reference points 6210 and 6211. The width 6231 is a spatial distance between the loss-composing points 6212 and 6213 that are the most distant in a side direction from a line that joins the reference points 6210 and 6211. The circumferential length 6232 is a sum of spatial distances between the two adjoining loss-composing points. The area indicates a spatial area of a space surrounded by all of the loss-composing points. The measurement screen, upon obtaining the calculated size of the burning 6200, displays the result window 6240 that indicates the measurement result as illustrated in FIG. 71E. Loss measurement is practicable to burn as explained previously.

Figure 72A:
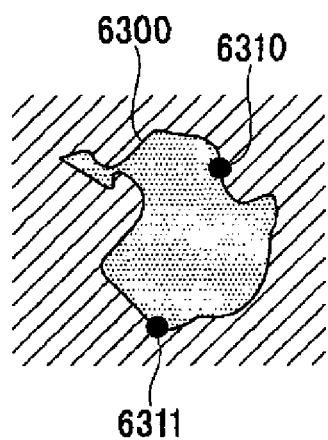
FIGS. 72A to 72F explain for reference the procedure of the twisted-shape detection process in the second embodiment (second operational example) of the present invention.
Figure 72B:
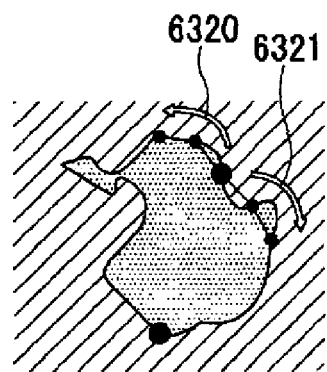
Figure 72C:
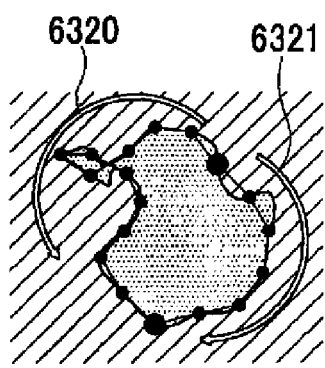

Sometimes, a loss outline may have a twisted shape associated with a measurement object described in the fourth operational example. For example, a burning 6300 as illustrated in FIG. 72A has a narrow and complex shape of edge. Sequential search conducted on the points between the two designated reference points positioned on the edge subsequent to designation of the reference points 6310 and 6311 obtains loss-composing points (measurement points) as illustrated in FIGS. 72*b* and 72C. Incidentally, the arrows 6320 and 6321 indicate two directions of searching the loss-composing points.

Figure 72D:
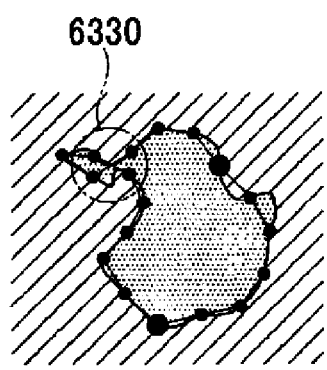
Figure 72E:
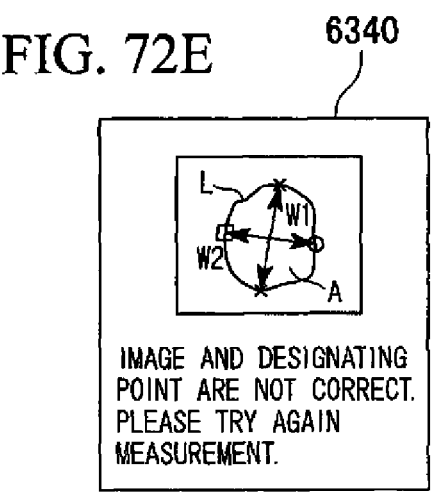

FIG. 72D illustrates the loss-composing points subsequent to the searching. The loss outline partly having a twisted shape is constituted by two line segments crossing in the area 6330. Accordingly, the measurement screen displays an result window 6340 that indicates an error in the measurement result as illustrated in FIG. 72E.

Figure 72F:
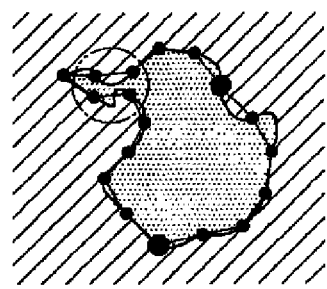

However, the twisted-shape-detecting process explained in the third operational example is still effective in this case. The twisted shape as illustrated in FIG. 72F can be disentangled by adapting the twisted-shape-detecting process as explained in the third operational example to the loss outline having a twisted shape as illustrated in FIG. 72D.

Detecting as to whether or not the loss outline has a twisted shape in accordance with the second embodiment can calculate a loss area. The first operational example and the second operational example upon detecting a twisted shape on a loss outline prompt the user to re-designate the reference points, and to prevent a twisted shape of the loss outline, thereby readily calculating the loss area. Also, the loss area can be calculated by correcting the loss-composing points in order to disentangle the twisted shape detected on the loss outline.

The embodiments of the present invention have been explained above in detail with reference to the drawings. However, it should be understood that the drawings and detailed description thereto are not intended to limit the invention to the particular form disclosed; thus, the invention disclosed herein is susceptible to various modifications and alternative forms, i.e., design changes.

What is claimed is:

1. A measurement method using an endoscope apparatus, the endoscope apparatus comprising an electronic endoscope that picks up a measurement object and produces a picked-up-image signal, an image-processing unit that produces an image signal based on the picked-up-image signal, and a measurement processing unit that measures the measurement object based on the image signal, the method being implemented by the endoscope apparatus to perform functions comprising:
   designating two reference points on the measurement object;
   calculating an approximate outline by approximating an outline of the measurement object based on the two reference points; and
   calculating loss-composing points that constitute the outline of a loss formed on the measurement object based on the two reference points and the approximate outline;
   wherein the two reference points are designated such that the loss formed on the measurement object is interposed between the two reference points.

2. The measurement method according to claim 1, further comprising measuring a size of the loss formed on the measurement object based on the loss-composing points.

3. The measurement method according to claim 1, wherein the approximate outline is calculated after having undergone distortion compensation to correct distortion associated with an image-pickup optical system provided to a distal end of the electronic endoscope.

4. The measurement method according to claim 1, further comprising:
   determining a loss type, the loss type indicating a type of the loss formed on the measurement object based on an angle defined by two approximate outlines corresponding to the two reference points; and
   calculating at least two characteristic points on the outline of the measurement object around the two reference points;
   wherein the two approximate outlines are calculated based on at least the two characteristic points.

5. The measurement method according to claim 4, further comprising calculating a parameter indicative of a loss size corresponding to the loss type.

6. The measurement method according to claim 5, further comprising calculating at least two parameters indicative of the loss size corresponding to the loss type.

7. The measurement method according to claim 1, further comprising:
   calculating one of the loss-composing points based on a cross-point of two approximate outlines corresponding to the two reference points; and
   calculating at least two characteristic points on the outline of the measurement object around a respective one of the two reference points;
   wherein the approximate outline is calculated based on at least the two characteristic points; and
   wherein the approximate outline includes the two approximate outlines.

8. The measurement method according to claim 1, further comprising designating at least one of the two reference points based on an end point positioned where the outline of the measurement object around the loss crosses with the outline of the loss.

9. The measurement method according to claim 1, further comprising reducing a contrast of an image based on the image signal to generate a contrast-reduced image.

10. The measurement method according to claim 9, further comprising switching a displaying status between a first state and a second state, wherein at least the contrast-reduced image is displayed in the first state, and the image before undergoing the contrast reduction is displayed in the second state without displaying the contrast-reduced image.

11. The measurement method according to claim 10, further comprising inputting a timing at which to switch the displaying status, wherein the displaying status is switched at a previously input timing.

12. The measurement method according to claim 11, further comprising:
   measuring a predetermined time length; and
   switching the displaying status after the predetermined time length has been measured.

13. The measurement method according to claim 9, wherein the contrast-reduced image in a previous contrast reduction is displayed in at least one of a first image-displaying area and a second image-displaying area.

14. The measurement method according to claim 1, further comprising converting an image based on the image signal into a binary image obtained by binarizing a signal level.

15. The measurement method according to claim 1, further comprising detecting whether or not a loss outline constituted by line segments joining the calculated loss-composing points has a twisted shape.

16. The measurement method according to claim 15, further comprising correcting the loss-composing points when the detecting detects that the loss outline has the twisted shape.

17. An endoscope apparatus comprising:
an electronic endoscope that picks up a measurement object and produces a picked-up-image signal;
an image-processing unit that produces an image signal based on the picked-up-image signal; and
a measurement processing unit that measures the measurement object based on the image signal;
wherein the measurement processing unit includes:
a reference point-designating unit that designates two reference points on the measurement object;
an approximate-outline calculating unit that calculates an approximate outline by approximating an outline of the measurement object based on the two reference points; and
a loss-composing points-calculating unit that calculates loss-composing points that constitute a loss outline formed on the measurement object based on the two reference points and the approximate outline; and
wherein the two reference points are designated such that the loss formed on the measurement object is interposed between the two reference points.

18. The endoscope apparatus according to claim 17, further comprising a loss-measurement unit that measures a size of the loss based on the loss-composing points.

19. The endoscope apparatus according to claim 17, further comprising a twisted-detection unit that detects whether or not the loss outline formed by line segments joining the calculated loss-composing points has a twisted shape.

20. The endoscope apparatus according to claim 19, further comprising a loss-composing-point-correcting unit that corrects the loss-composing points when the twisted-detection unit detects that the loss outline has the twisted shape.

21. A loss-displaying method using an endoscope apparatus, the endoscope apparatus comprising an electronic endoscope that picks up a measurement object and produces a picked-up-image signal, an image-processing unit that produces an image signal based on the picked-up-image signal, and a measurement processing unit that measures the measurement object based on the image signal, the method being implemented by the endoscope apparatus to perform functions comprising:
displaying two reference points on the designated measurement object;
displaying an approximate outline by approximating an outline of the measurement object; and
displaying a loss formed on the measurement object and calculated based on the two reference points and the approximate outline;
wherein the two reference points are designated such that the loss formed on the measurement object is interposed between the two reference points.

22. The loss-displaying method according to claim 21, further comprising displaying loss-composing points that constitute the loss outline.

23. The loss-displaying method according to claim 22, further comprising displaying the loss outline constituted by line segments joining the loss-composing points.

24. The loss-displaying method according to claim 23, further comprising displaying a size of the loss, the size of the loss being measured based on the loss-composing points.

25. The loss-displaying method according to claim 23, further comprising displaying a result of a determination as to whether or not the loss outline has a twisted shape.

26. The loss-displaying method according to claim 23, further comprising displaying corrected loss-composing points when it is determined that the loss outline has a twisted shape.

27. The loss-displaying method according to claim 21, further comprising displaying a type of the loss, the type of the loss being determined based on an angle defined by two approximate outlines corresponding to the two reference points.

28. The loss-displaying method according to claim 21, further comprising displaying cross-points of two approximate outlines, the cross-points corresponding to the two reference points.

29. The loss-displaying method according to claim 21, further comprising displaying at least one of the two reference points based on an end point positioned where the outline of the measurement object around the loss crosses with the loss outline.

30. The loss-displaying method according to claim 21, further comprising reducing image contrast based on the image signal to generate a contrast-reduced image.

31. The loss-displaying method according to claim 30, further comprising switching a displaying status between a first state and a second state, wherein the contrast-reduced image is displayed in the first state, and the image prior to undergoing the contrast reduction is displayed in the second state instead of displaying the contrast-reduced image.

32. The loss-displaying method according to claim 31, further comprising switching the displaying status at a timing input by a user.

33. The loss-displaying method according to claim 31, further comprising displaying the displaying status that has been switched at a second timing obtained after measuring a lapse of time from a point at which the displaying status was previously switched.

34. The loss-displaying method according to claim 30, further comprising displaying the contrast-reduced image in at least one of a first image-displaying area and a second image-displaying area.

35. The loss-displaying method according to claim 21, further comprising displaying a signal level obtained by binarizing the image based on the image signal.

* * * * *